US012644097B2

(12) United States Patent
Singec et al.

(10) Patent No.: US 12,644,097 B2
(45) Date of Patent: Jun. 2, 2026

(54) DIFFERENTIATION OF TROPHECTODERM LINEAGE CELLS FROM PLURIPOTENT STEM CELLS

(71) Applicant: The United States of America, as represented by the Secretary, Dept. of Health and Human Services, Rockville, MD (US)

(72) Inventors: Ilyas Singec, Gaithersburg, MD (US); Jaroslav Slamecka, Gaithersburg, MD (US); Anton Simeonov, Bethesda, MD (US); Tao Deng, Potomac, MD (US)

(73) Assignee: The United States of America as represented by the Secretary, Department of Health and Human Services, Bethesda, MD (US)

( * ) Notice: Subject to any disclaimer, the term of this patent is extended or adjusted under 35 U.S.C. 154(b) by 613 days.

(21) Appl. No.: 18/000,653

(22) PCT Filed: Jun. 2, 2021

(86) PCT No.: PCT/US2021/035527
§ 371 (c)(1),
(2) Date: Dec. 2, 2022

(87) PCT Pub. No.: WO2021/247760
PCT Pub. Date: Dec. 9, 2021

(65) Prior Publication Data
US 2023/0220334 A1 Jul. 13, 2023

Related U.S. Application Data

(60) Provisional application No. 63/033,536, filed on Jun. 2, 2020.

(51) Int. Cl.
*C12N 5/073* (2010.01)

(52) U.S. Cl.
CPC ........ *C12N 5/0605* (2013.01); *C12N 2500/02* (2013.01); *C12N 2501/11* (2013.01); *C12N 2501/115* (2013.01); *C12N 2501/12* (2013.01); *C12N 2501/13* (2013.01); *C12N 2501/15* (2013.01); *C12N 2501/155* (2013.01)

(58) Field of Classification Search
CPC ................................................ C12N 2501/155
See application file for complete search history.

(56) References Cited

U.S. PATENT DOCUMENTS

| | | | | |
|---|---|---|---|---|
| 2010/0273259 | A1* | 10/2010 | Saha .................. | G01N 23/2258 |
| | | | | 435/395 |
| 2018/0135022 | A1 | 5/2018 | Asano et al. | |
| 2020/0017827 | A1* | 1/2020 | Shusta ................. | C12N 5/0618 |

FOREIGN PATENT DOCUMENTS

| | | | | |
|---|---|---|---|---|
| NL | | 1036427 C2 | * | 7/2010 |
| WO | WO 2014011881 A | | * | 1/2014 |

OTHER PUBLICATIONS

Parast, Generation of cytotrophoblast-like cells from human embryonic stem cells in defined media. Pediatric Research, (Oct. 2013) vol. 74, No. 4, pp. 483. Abstract No. 2-12. (Year: 2013).*

Huang, Establishment of bovine trophoblast stem-like cells from in vitro-produced blastocyst-stage embryos using two inhibitors. Stem cells and development, (Jul. 1, 2014) vol. 23, No. 13, pp. 1501-1514 (Year: 2014).*

Dong Chen et al, "Derivation of trophoblast stem cells from naïve human pluripotent stem cells", ELIFE, Feb. 12, 2020 (Feb. 12, 2020), vol. 9.

M. Amita et al, "Complete and unidirectional conversion of human embryonic stem cells to trophoblast by BMP4", Proceedings of the National Academy of Sciences, vol. 110, No. 13, Mar. 14, 2013 (Mar. 14, 2013).

Transmittal, including International Search Report and Written Opinion, dated Aug. 25, 2021, and issued in connection with PCT International Application No. PCT/US2021/035527.

* cited by examiner

*Primary Examiner* — Qiuwen Mi
(74) *Attorney, Agent, or Firm* — Armstrong Teasdale LLP

(57) ABSTRACT

Methods for generating in culture of cells resembling mammalian trophectoderm-lineage cells from mammalian pluripotent stem cells are provided, along with the related compositions.

14 Claims, 33 Drawing Sheets

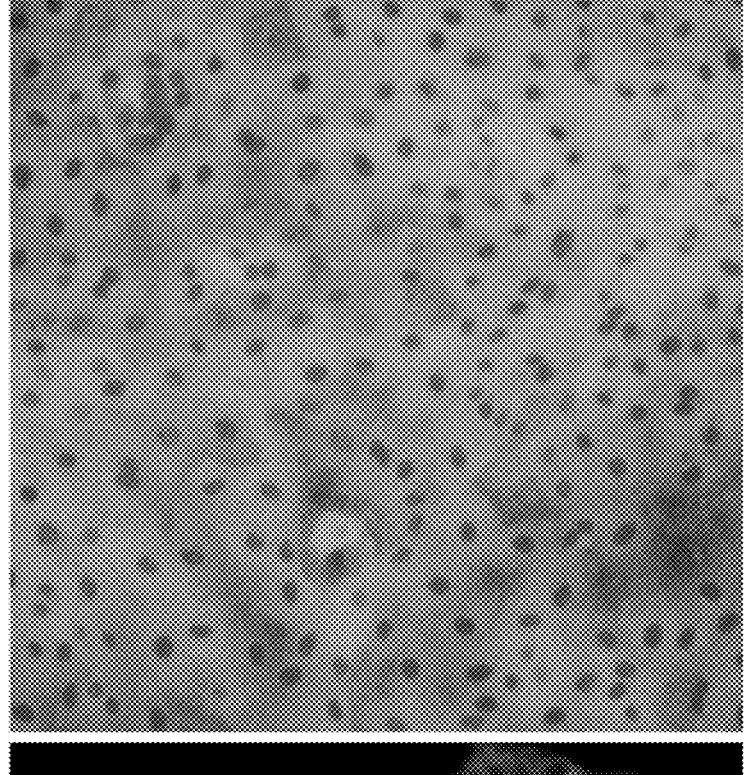
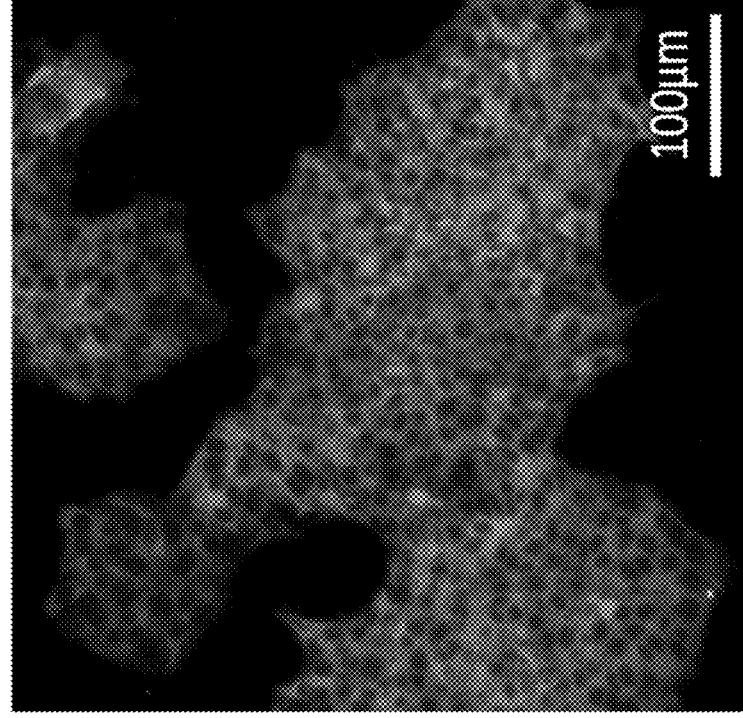
FIG. 3

Cytotrophoblast-like cells

Syncytiotrophoblast-like structure

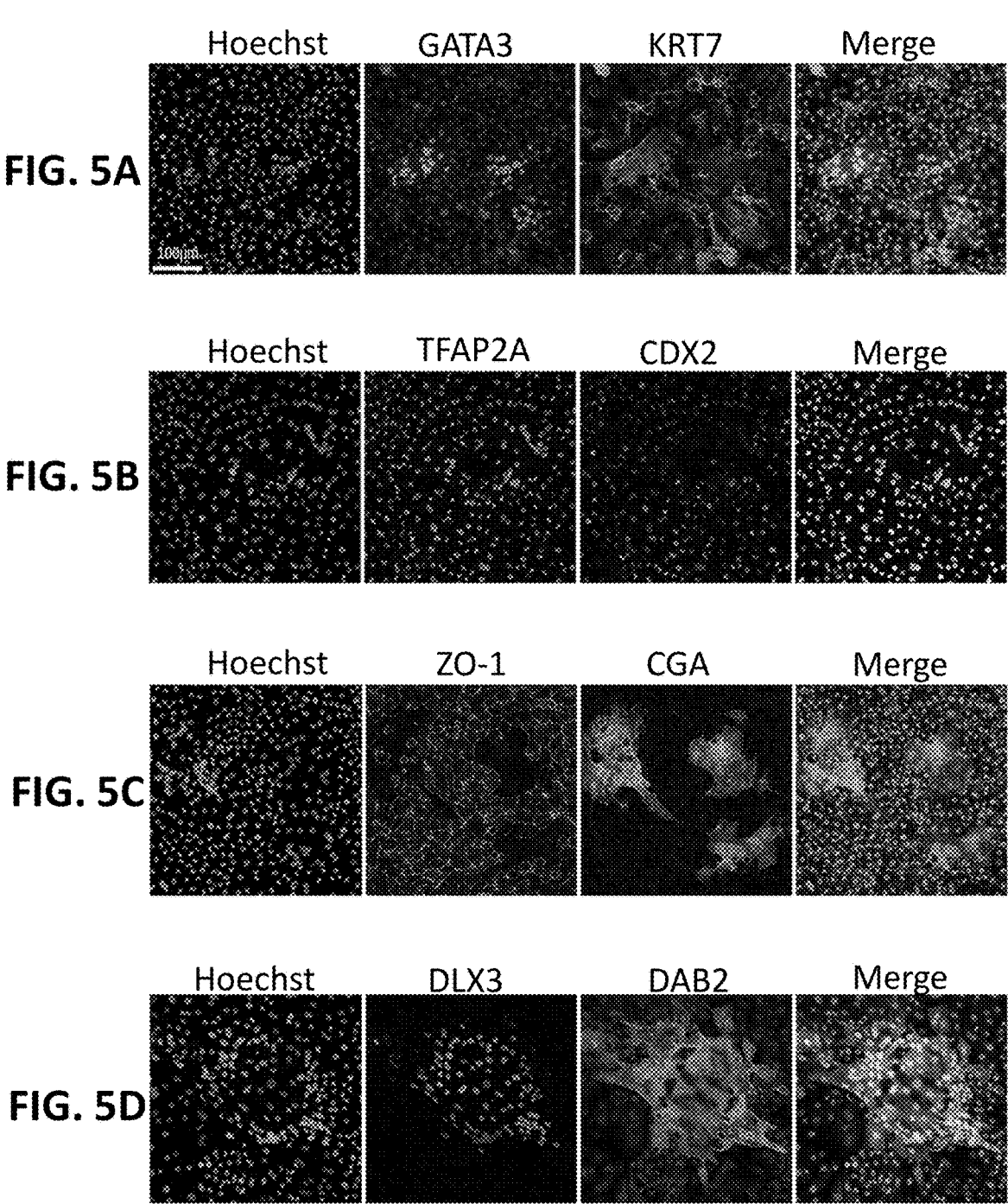

Day 10

DLX3/Hoechst/Phase

DLX3/Hoechst

Expansion of Trophoblast Stem-Like Cells (WA09; Passage 22)

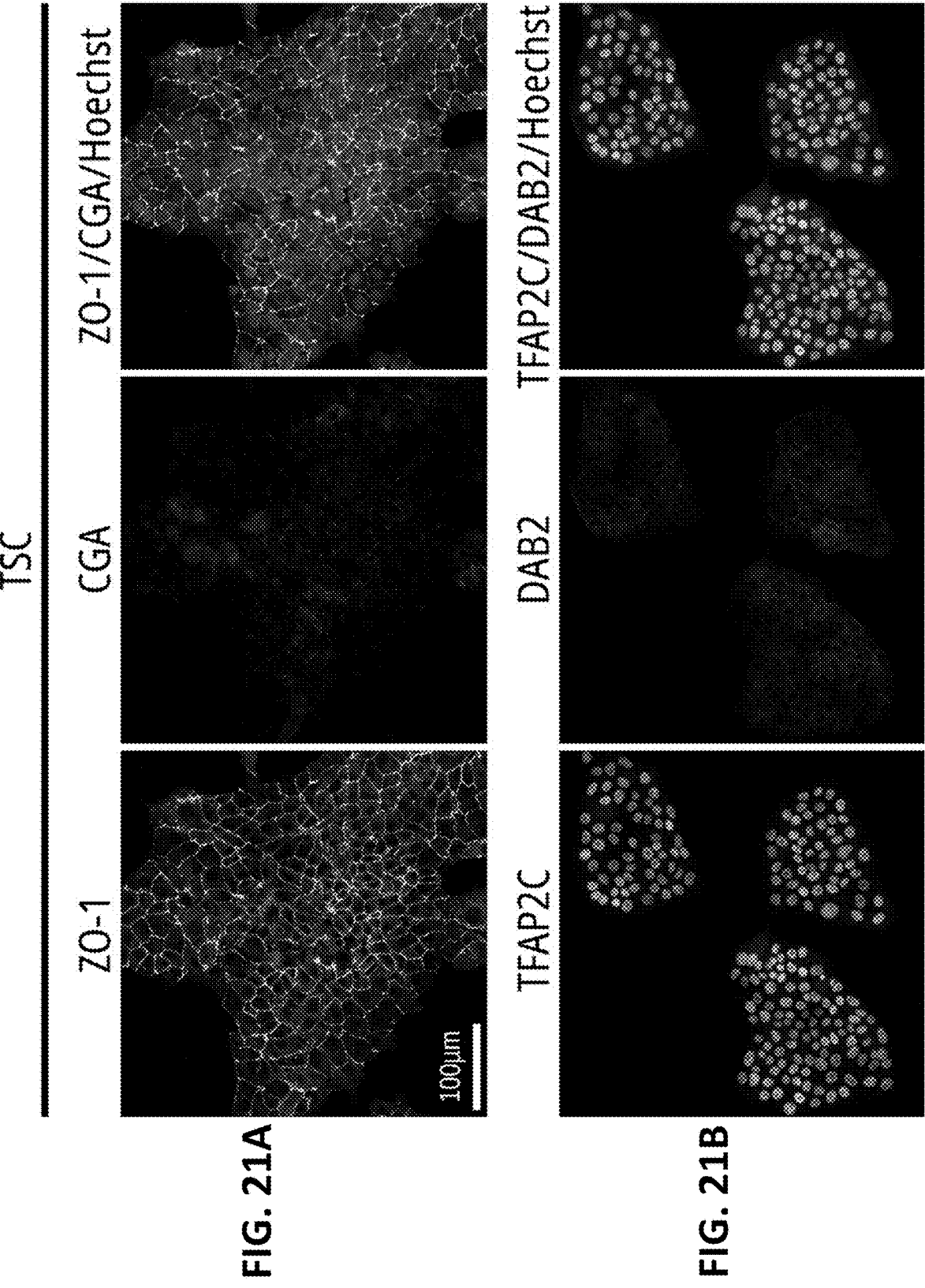

1

DIFFERENTIATION OF TROPHECTODERM LINEAGE CELLS FROM PLURIPOTENT STEM CELLS

CROSS-REFERENCE TO RELATED APPLICATIONS

This application is a § 371 national stage of PCT International Application No. PCT/US2021/035527, filed Jun. 2, 2021, which claims the benefit of priority to U.S. Provisional Application No. 63/033,536, filed Jun. 2, 2020, the contents of which is hereby expressly incorporated by reference in its entirety.

GOVERNMENT LICENSE RIGHTS

This invention was made with Government support awarded by NIH Regenerative Medicine Program of the National Institutes of Health (NIH Common Fund) and National Center for Advancing Translational Sciences (NCATS). The Government has certain rights in the invention.

FIELD

The present invention lies in the fields of biochemistry, cell biology, bioengineering, drug development and stem cell biology, as well as related fields, and concerns the compositions and methods useful for culturing and differentiating pluripotent stem cells.

BACKGROUND

Pluripotency is a remarkable cellular state that allows differentiation of stem cells into any cell type of the human body. Vertebrate pluripotent stem cells, including embryonic stem cells (ESCs) and induced pluripotent stem cells (iPSCs), undergo extensive self-renewal and have the potential to differentiate into all somatic cell types. Generating desired cell types from pluripotent stem cells hold enormous potential for drug discovery, disease modeling and regenerative medicine. For instance, research concerning early human development, diseases of affecting placenta, drug screening, and cell-based therapies would greatly benefit from directed differentiation of human pluripotent stem cells (hPSCs) into cells exhibiting characteristics of the cells of human trophectoderm lineage (which can also be referred to as "placental cells"). Unfortunately, existing procedures of producing trophectoderm-lineage cells from human pluripotent stem cells can be inefficient, undefined and lengthy. For example, current access to human placental cells for basic and translation research is very limited, largely depending on primary fetal tissues or cancer cell lines. Existing procedures also show poor reproducibility, require expensive supplements and often generate chaotic mixtures of different cell lineages. Therefore, a need exists for improved methods for generating from pluripotent stem cells of the cells exhibiting at least some characteristics of trophectoderm-lineage cells.

SUMMARY

Described and included among the embodiments of the present invention are methods useful for production from pluripotent stem cells of the cells exhibiting at least some characteristics of the cells of trophectoderm lineage of mammals, such as, but not limited to humans. For example, described and included among the embodiments of the present invention are methods useful for production from pluripotent stem cells of cytotrophoblast-like cells and syncytiotrophblast-like structures. Also described and included among the embodiments of the present invention are methods useful for production and maintenance in culture of self-renewing cells exhibiting at least some characteristics of trophoblast stem cells. Among other things, the methods described in this disclosure are highly efficient, cost-effective, reproducible, scalable and suitable for automation. The methods described in this disclosure are useful, among other things, for example, in drug discovery and development, high-throughput screening of compounds for various applications, including drug development and toxicity screening, in the research of pregnancy, infertility, and early development of mammals, including humans, in disease modeling and research, in cell-based therapies, and cell and tissue engineering. The advantages of the compositions, kits and methods of the present invention are discussed throughout this disclosure and illustrated in the accompanying figures.

The terms "invention," "the invention," "this invention" and "the present invention," as used in this disclosure, are intended to refer broadly to all of the subject matter of this patent application and the claims below. Statements containing these terms should be understood not to limit the subject matter described herein or to limit the meaning or scope of the patent claims below. Covered embodiments of the invention are defined by the claims, not this summary. This summary is a high-level overview of various aspects of the invention and introduces some of the concepts that are described and illustrated in the present disclosure and the accompanying figures. This summary is not intended to identify key or essential features of the claimed subject matter, nor is it intended to be used in isolation to determine the scope of the claimed subject matter. The subject matter should be understood by reference to appropriate portions of the entire specification, any or all figures and each claim. The present disclosure describes and refers to various embodiments of the invention. No particular embodiment is intended to define the scope of the invention. Rather, the embodiments merely provide non-limiting examples of various methods, compositions, kits, systems etc. that are at least included within the scope of the invention. Some embodiments of the present invention are summarized below, while others are described and shown elsewhere in the present disclosure.

Exemplary embodiments of the present invention include methods of producing cultured cells comprising cytotrophoblast-like cells. Such methods can comprise the steps of: plating mammalian pluripotent stem cells on a vitronectin-coated surface of a culture vessel; incubating the plated mammalian pluripotent stem cells for approximately 12-24 hours in a first culture medium until a confluence of approximately 25-50% is achieved; replacing the first culture medium with a second culture medium comprising an effective amount or concentration of first one or more inhibitors of transforming growth factor beta (TGF-beta) signaling, an effective amount or concentration of first one or more activators of Wnt signaling, an effective amount or concentration of one or more inhibitors of fibroblast growth factor (FGF) receptor signaling, an effective amount or concentration of bone morphogenic protein 4 (BMP4), and an effective amount or concentration of bone morphogenic protein 10 (BMP10); and, culturing the plated mammalian pluripotent stem cells in the second culture medium for approximately 24-96 hours, thereby generating the cultured cells comprising the cytotrophoblast-like cells. The mammalian pluripotent stem cells (for example, human pluripotent stem cells) used in the methods according to the embodiments of the present invention can be induced pluripotent stem cells or embryonic pluripotent stem cells.

The first culture medium can be a first defined culture medium, such as, but not limited to, E8, E8 Flex, StemFlex, mTeSR, StemFit, or mouse embryonic fibroblast (MEF)-conditioned medium. The first culture medium can comprise an effective concentration of Chroman 1 or a derivative thereof, an effective concentration of Emricasan or a derivative thereof, an effective concentration of trans-ISRIB and an effective concentration of polyamines comprising putrescine, spermine and spermidine. For example, the effective concentration of Chroman 1 or the derivative thereof can be about 4 nM to about 80 µM, the effective concentration of Emricasan or the derivative thereof can be about 100 nM to about 80 µM, the effective concentration of trans-ISRIB can be about 50 nM to about 80 µM, and wherein putrescine, spermine and spermidine each can be at a concentration of about 0.5 nM to 1 mM. The plated mammalian stem cells can be incubated in the first culture medium until a confluence of approximately 30-35% is achieved.

In the methods according to the embodiments of the present invention, the second culture medium can be a second defined culture medium, such as, but not limited to, DMEM-F12, E6, Neurobasal medium, or Minimum Essential Medium (MEM). The first one or more inhibitors of TGF-beta signaling can comprise one or both A83-01 or SB 431542. The first one or more activators of Wnt signaling can comprise one or both of CHIR99021 or CHIR98014. The first one or more inhibitors of FGF receptor signaling can comprise one or more of CH5183284, PD-166866, or PD 173074. The plated mammalian pluripotent stem cells can be incubated in the second culture medium for approximately 72 hours. During the culturing in the second culture medium, the cells being cultured can detectably downregulate expression of one or more of pluripotency transcription factors (which can comprise one or both of OCT4 or NANOG) at approximately 48 to 120 hours after start of the culturing in the second culture medium. During the culturing in the second culture medium, the cells being cultured detectably upregulate expression of one or more cytotrophoblast-associated markers (which can comprise one or more of CDX2, GATA3, KRT7, KRT18, TFAP2A, or IGFBP3) at approximately 48-120 hours after start of the culturing in the second culture medium. The cytotrophoblast-like cells generated by the methods according to the embodiments of the present invention can detectably store glycogen in cytoplasm.

Exemplary embodiments of the present invention include methods of producing a culture comprising the cytotrophoblast-like cells and syncytiotrophoblast-like structures. Such methods comprise the step of culturing, for approximately 168-312 hours, cytotrophoblast-like cells according to the embodiments of the present invention in a third culture medium comprising an effective amount or concentration of second one or more inhibitors of TGF-beta signaling, and an effective amount or concentration of second one or more activators of Wnt signaling, thereby generating the culture comprising the cytotrophoblast-like cells and the syncytiotrophoblast-like structures. Some embodiments of the above methods can comprise the steps of producing cultured cells comprising cytotrophoblast-like cells; replacing the second culture medium in a culture of the cells comprising the cytotrophoblast-like cells with the third culture medium; and, culturing the cells comprising the cytotrophoblast-like cells in the third culture medium for approximately 168-312 hours, thereby generating the culture comprising the cytotrophoblast-like cells and the syncytiotrophoblast-like structures. The third culture medium can be a second defined culture medium, such as, but not limited to, DMEM-F12, E6, Neurobasal medium, or Minimum Essential Medium (MEM). The second one or more inhibitors of TGF-beta signaling can comprise one or both of A83-01 or SB 431542. The second one or more activators of Wnt signaling can comprise one or both of CHIR99021 or CHIR98014. The syncytiotrophoblast-like structures generated according to the embodiments of the methods of the present invention can detectably express one or more of syncytiotrophoblast markers, which can comprise one or more of DLX3, CGA, GATA3, KRT7, DAB2, TEAD3, or TFAP2C. The syncytiotrophoblast-like structures generated according to the embodiments of the methods of the present invention can detectably upregulate expression of DAB2.

Exemplary embodiments of the present invention include methods of producing a culture comprising trophoblast stem-like cells. Such methods comprise a step of culturing a culture comprising cytotrophoblast-like cells and syncytiotrophoblast-like structures in the fourth culture medium comprising an effective amount or concentration of third one or more inhibitors TGF-beta signaling, an effective amount or concentration of third one or more activators of Wnt signaling, an effective amount or concentration of EGF, an effective amount or concentration of HGF, an effective amount or concentration of R-spondin 1, an effective amount or concentration of R-spondin 3, an effective amount or concentration of prostaglandin E$_2$, and effective amount or concentration of one or more ROCK inhibitors, or an effective amount or concentration of an inhibitor of myosin II ATPase, thereby generating the culture comprising trophoblast stem-like cells. Some embodiments of the above methods can comprise the steps of producing a culture comprising cytotrophoblast-like cells and syncytiotrophoblast-like structures, and replacing the third culture medium in the culture comprising the cytotrophoblast-like cells and the syncytiotrophoblast-like structures with the fourth culture medium; and, culturing the culture comprising the cytotrophoblast-like cells and the syncytiotrophoblast-like structures in the fourth culture medium, thereby generating the culture comprising trophoblast stem-like cells. The fourth culture medium can be a fourth defined culture medium, such as, but not limited to, DMEM-F12, E6, Neurobasal medium, or Minimum Essential Medium (MEM). The third one or more inhibitors of TGF-beta signaling can comprise one or both of A83-01 or SB 431542. The third one or more activators of Wnt signaling can comprise one or both of CHIR99021 or CHIR98014. The one or more ROCK inhibitors can comprise one or more of Chroman 1, Y-27632, or Thiazovivin. The inhibitor of myosin II ATPase can be blebbistatin. The trophoblast stem-like cells produced by the methods according to the embodiments of the present invention are self-renewing. The trophoblast stem-like cells can detectably express Ki-67. The trophoblast stem-like cells can detectably express one or more of ELF5, GATA3, CDX2, TFAP2C, KRT7, or YAP1.

Also included among the embodiments of the present invention are compositions comprising at least one cytotrophoblast-like cell detectably expressing one or more of CDX2, GATA3, KRT7, KRT18, TFAP2A, or IGFBP3. Such a composition can be cryopreserved, or has previously been subjected to cryopservation. Also included among the embodiments of the present invention are culture comprising a plurality of cytotrophoblast-like cells detectably expressing one or more of CDX2, GATA3, KRT7, KRT18, TFAP2A, or IGFBP3. Also included among the embodiments of the present invention are compositions comprising at least one syncytiotrophoblast-like structure detectably expressing one or more of DLX3, CGA, GATA3, KRT7, DAB2, TEAD3, or TFAP2C. Also included among the embodiments of the present invention are cell cultures comprising at least one syncytiotrophoblast-like structure detectably expressing one or more of DLX3, CGA, GATA3, KRT7, DAB2, TEAD3, or TFAP2C. Also included among the embodiments of the present invention are compositions comprising at least one trophoblast stem-like cell detectably expressing one or more of ELF5, GATA3, CDX2, TFAP2C, KRT7, or YAP1. Such a composition can be cryopreserved, or has been previously subjected to cryopreservation. Also included among the embodiments of the present invention comprising a plurality of trophoblast stem-like cells detectably expressing one or more of ELF5, GATA3, CDX2, TFAP2C, KRT7, or YAP1. One or more trophoblast stem-like cell included in the compositions and cultures according to the embodiments of the present invention can detectably expresses Ki-67.

Further exemplary embodiments of the present disclosure are directed to methods of producing a culture comprising syncytiotrophoblast-like structures, comprising: culturing a culture comprising trophoblast stem-like cells in a fifth culture medium comprising an effective concentration of at least one ROCK inhibitor, an effective concentration of forskolin; culturing the culture comprising trophoblast stem-like cells in the fifth culture medium under conditions of normoxia, thereby generating the culture comprising the syncytiotrophoblast-like structures. In some embodiments, the culture comprising the trophoblast stem-like cells was generated by performing methods disclosed herein, and wherein culturing the culture comprising the trophoblast stem-like cells in the fifth culture medium comprises replacing the fourth culture medium with the fifth culture medium.

Yet further exemplary embodiments of the present disclosure are directed to methods of producing a culture comprising extravillous trophoblast-like cells, comprising: culturing a culture comprising trophoblast stem-like cells in a sixth culture medium comprising an effective concentration of at least one ROCK inhibitor, an effective concentration of at least one epidermal growth factor (EGF), an effective concentration of human neuregulin (NRG), and an effective concentration of at least one inhibitor of transforming growth factor beta (TGF-beta); and culturing the culture comprising trophoblast stem-like cells in the sixth culture medium under conditions of hypoxia, thereby generating the culture comprising the extravillous trophoblast-like cells. In some embodiments, the culture comprising the trophoblast stem-like cells was generated by performing methods disclosed herein, and wherein culturing the culture comprising the trophoblast stem-like cells in the sixth culture medium comprises replacing the fourth culture medium with the sixth culture medium.

BRIEF DESCRIPTION OF THE FIGURES

FIG. 3 shows representative microscopic images illustrating glycogen accumulation in differentiating cytotrophoblast-like cells produced by an embodiment of a method described in the present disclosure. The cells were stained using periodic acid-Schiff staining. The image in the right panel is of the differentiating cytotrophoblast-like cells. The image in the left panel is of the pluripotent stem cells.

FIG. 5A shows a representative microscopic image illustrating immunocytochemical analysis of the differentiating cells at "Day 10" of an embodiment of a method described in the present disclosure. Hoechst 33342 dye was used to stain nuclei (the images labeled "Hoechst") and the merged images (labeled "Merge") illustrating the detection of two markers simultaneously. This figure illustrates expression of transcription factor GATA3 and cytokeratin KRT7 by the differentiating cells.

FIG. 5B shows a representative microscopic image illustrating immunocytochemical analysis of the differentiating cells at "Day 10" of an embodiment of a method described in the present disclosure. Hoechst 33342 dye was used to stain nuclei (the images labeled "Hoechst") and the merged images (labeled "Merge") illustrating the detection of two markers simultaneously. This figure illustrates expression of transcription factors TFAP2A and CDX2 by the differentiating cells.

FIG. 5C shows a representative microscopic image illustrating immunocytochemical analysis of the differentiating cells at "Day 10" of an embodiment of a method described in the present disclosure. Hoechst 33342 dye was used to stain nuclei (the images labeled "Hoechst") and the merged images (labeled "Merge") illustrating the detection of two markers simultaneously. This figure illustrates expression of tight junction protein ZO-1 and human chorionic gonadotropin (CGA) by the differentiating cells.

FIG. 5D shows representative microscopic images illustrating immunocytochemical analysis of the differentiating cells at "Day 10" of an embodiment of a method described in the present disclosure. Hoechst 33342 dye was used to stain nuclei (the images labeled "Hoechst") and the merged images (labeled "Merge") illustrating the detection of two markers simultaneously. This figure illustrates expression of transcription factor DLX3 and enrichment of mitogen-responsive phosphoprotein DAB2 in syncytiotrophoblast-like structures but not in the surrounding cytotrophoblast-like cells.

FIG. 8A illustrates expression of markers GATA3 and KRT7.

FIG. 21A is a photographic image illustrating immunocytochemical analysis of TSC before and after differentiation into STB as described in the present disclosure.

FIG. 21B is a photographic image illustrating immunocytochemical analysis of TSC before and after differentiation into STB as described in the present disclosure.

DESCRIPTION

Figure 1:
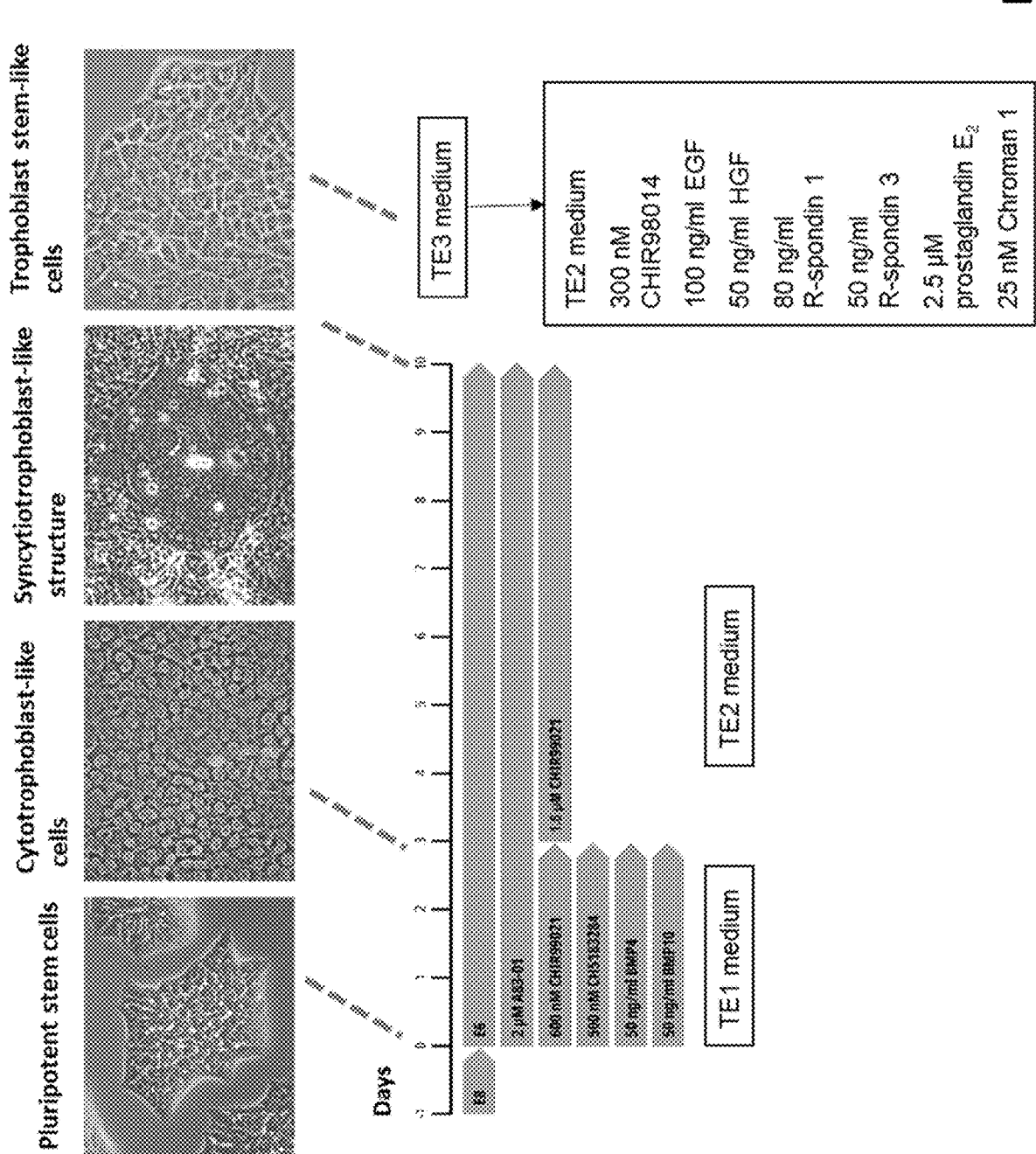
FIG. 1 shows a schematic illustration of embodiments of methods described in the present disclosure for producing trophectoderm lineage-like cells from human pluripotent stem cells, as well as the representative images of the cells and structures generated by the illustrated methods.

During pre-implantation development of mammals, a blastocyst-stage embryo is composed of embryonic and extra-embryonic tissues. The embryonic tissue is represented by the inner cell mass (ICM), which gives rise to the embryo proper (also referred to as "epiblast" after implantation into the uterus), while the surrounding extra-embryonic tissue represents the trophectoderm lineage, which will differentiate into placenta. Self-renewing stem cells featuring characteristics of the ICM can be cultured in vitro as embryonic stem cells (ESCs) or induced pluripotent stem cell (iPSCs) after successful reprogramming of somatic cells using defined transcription factors. It is currently held that the in vivo embryonic counterparts of cultured human pluripotent stem cells (hPSC) are presumably the cells of the post-implantation epiblast, with a capacity restricted to giving rise to the embryo proper and no longer able to develop into trophectoderm-lineage cells. Previous studies that reported differentiation of trophectoderm-lineage cells from pluripotent stem cells remain controversial, in part, due to incomplete differentiation of the cells, expression of mesodermal genes in the resulting cells, or the use of undefined culture conditions.

The embodiments of the present invention were envisioned at least in part based on the discoveries discussed below. By manipulating critical cell signaling pathways at defined time points by using various additives and their combinations, the inventors discovered procedures for converting human pluripotent stem cells in culture into various cell types resembling cells of human trophectoderm lineage (trophectoderm lineage-like cells). For example, using one type of a procedure and starting from human pluripotent stem cells, the inventors generated cell cultures that included cytotrophoblast-like cells. By subjecting the above cell cultures to another type of a procedure, the inventors generated cell cultures that included syncytiotrophoblast-like structures. By subjecting the above cell cultures including syncytiotrophoblast-like structures to yet another type of a procedure, the inventors generated cell cultures of self-renewing trophoblast-like cells (trophoblast stem cell-like cells), which are capable, under appropriate conditions, of differentiating, for example, into extravillous trophoblast-like cells and syncytiotrophoblast-like structures. Morphological, molecular and functional characterization experiments confirmed the properties of various cell types generated by the inventors. Accordingly, the inventors conceived various methods, as well as the related compositions and kits, for producing, starting from pluripotent stem cells (PSCs) of mammals, including humans, trophectoderm lineage-like cells, such as cytotrophoblast-like cells, multinucleated syncytiotrophoblast-like structures, trophoblast stem cell-like cells, and extravillous trophoblast-like cells.

The processes described in the present disclosure allow production of desired cell populations of trophectoderm lineage like-cells in culture (for example, cytotrophoblast-like cells (CTB), syncytiotrophoblast-like structures (STB), trophoblast stem cell-like cells (TSC), and extravillous trophoblast-like cells (EVT)) in culture in a highly efficient, controlled, and stepwise manner. The processes described in the present disclosure overcame the scientific and technical limitations of previously published methods, such as poor efficiency, extensive length, undefined conditions, such as the use of undefined culture media and supplements, poor reproducibility, and poorly defined products, such as mixtures of various types of cell lineages in the same culture and questionable identity of the cells declared to be similar to natural trophectoderm lineage cells. Various embodiments of the processes are envisioned and described in the present disclosure. Some embodiments of the processes described in the present disclosure produce cultures of cytotrophoblast-like cells from PSCs. Some other embodiments of the processes described in the present disclosure produce cultures containing syncytiotrophoblast-like structures from cytotrophoblast-like cells. The above processes can be combined into embodiments of the processes that produce cultures containing syncytiotrophoblast-like structures from PSCs. Yet other embodiments of the processes described in the present disclosure produce cultures of trophoblast stem-like cells from the cultures containing syncytiotrophoblast-like structures. In yet other embodiments of the present disclosure, processes are described for production of extravillous trophoblast-like cells from trophoblast stem-like cells. All of the above processes can be combined into embodiments of the processes that produce cultures of trophoblast stem-like cells from PSCs.

The processes described in the present disclosure are highly advantageous and superior to the previously known processes for various reasons. For example, in contrast to the previously known processes, the processes described in the present disclosure produce highly pure populations of various trophectoderm lineage-like cells using chemically defined conditions. Some embodiments of the processes described in the present disclosure do not require the use of undefined culture media components, such as animal serum. Such embodiments can be carried out under chemically defined conditions compatible with good manufacturing practice (GMP) approaches, clinical translation, and cell therapy. At least some of the processes described in the present disclosure produce trophectoderm lineage-like cells that have a capacity to proliferate while retaining their specific characteristics. Long-term proliferation of any trophoblast-like cells under defined conditions derived from human pluripotent stem cells was not previously achieved.

The inventors also conceived compositions and kits related to the processes described in the present disclosure, as well as various applications and uses of their processes (methods), compositions and kits, including high-throughput applications and uses requiring large numbers of standardized cells of high quality. Among other things, various embodiments of the invention described in the present disclosure can be used in drug discovery and development, toxicity screenings, research of pregnancy, infertility, and early development of mammals (including humans), disease modeling and research, cell and tissue engineering, and in cell replacement therapies. For example, for the purpose of disease modeling, induced pluripotent stem cells (iPSC) can be derived from patients with placental disorders (such as, but not limited to, pre-eclampsia or intra-uterine growth restriction), metabolic diseases (such as, but not limited to, diabetes mellitus), and other conditions. The iPSCs can then be expanded and differentiated into trophectoderm lineage-like cells described in this disclosure. Such trophectoderm lineage-like cells allow for detailed and controlled investigation of the mechanisms and factors (such as genetic or epigenetic factors) underlying the disease or condition of the source patient. In another example, trophectoderm lineage-like cells described in the present disclosure are useful in studies of the mechanisms that drive cellular proliferation of trophectoderm/trophoblast cells, which can lead to better understanding and treatment of choriocarcinoma arising by tumorigenic transformation of placental cells. Trophectoderm lineage-like cells according to the embodiments of the present invention are also useful in cell replacement therapies. For example, genetically corrected trophoblast stem-like cells can be administered to patient in need of such cells. The processes of differentiating human iPSCs into trophectoderm lineage-like cells described in the present disclosure showed that human PSCs cultured in vitro had a greater developmental potential that was previously known, and can generate cell types previously considered inaccessible in culture. Studying early developmental processes is not only technically difficult in humans, but also poses significant ethical challenges when human embryonic and fetal tissues are used as a starting material. Accordingly, various rules and regulations significantly restrict such studies. For example, U.S. federal law allows culturing human embryos in vitro only for up to 14 days after the point of fertilization. The processes, cells and cell cultures described in the present disclosure obviate ethical controversies and legal restrictions arising out of use of early embryonic and fetal human tissues.

Terms and Concepts

A number of terms and concepts are discussed below. They are intended to facilitate the understanding of various embodiments of the invention in conjunction with the rest of the present disclosure and the accompanying figures. These terms and concepts may be further clarified and understood based on the accepted conventions in the fields of the present invention and the description provided throughout the present disclosure and/or the accompanying figures. Some other terms can be explicitly or implicitly defined in other sections of this disclosure and in the accompanying figures and may be used and understood based on the accepted conventions in the fields of the present invention, the description provided throughout the present disclosure and/or the accompanying figures. The terms not explicitly defined can also be defined and understood based on the accepted conventions in the fields of the present invention and interpreted in the context of the present disclosure and/or the accompanying figures.

As used herein, the terms "a," "an," and "the" can refer to "one," "one or more" or "at least one," unless specifically noted otherwise.

The terms "about" or "approximately" are used herein to indicate that a value includes the inherent variation of error for the device, the method being employed to determine the value, or simply error-tolerance of a value. For example, the terms "about" or "approximately" may mean ±1%, ±5%, ±10%, ±15% or ±20% variation from a predetermined value.

As used herein, the terms "isolate," "separate" or "purify" and the related terms are not used necessarily to refer to the removal of all materials other than the components of interest from a sample. Instead, in some embodiments, the terms are used to refer to a procedure that enriches the amount of one or more components of interest relative to one or more other components present in the sample. In some embodiments, "isolation," "separation" or "purification" may be used to remove or decrease the amount of one or more components from a sample. For example, the expression "an isolated cell" can refer to a cell that has been substantially separated or purified away from other cells of a cell culture or an organism.

The term "derived" and the related expressions referring to cells or a biological sample indicate that the cell or sample was obtained from the stated source at some point in time. For example, a cell derived from an organism can represent a primary cell obtained directly from the individual (that is, unmodified), or it can be modified, for example, by introduction of a recombinant vector, by exposure to or culturing under particular conditions, or immortalization. In some cases, a cell derived from a given source will undergo cell division and/or differentiation such that the original cell no longer exists, but the continuing cells will be understood to derive from the same source. The term "derive," "derivation" and the related terms and expressions can also be used in this disclosure to refer to creation of a cell population, cell, or culture from a different starting or preceding cell population, cell, or culture. For example, in each of the cases of a population of trophectoderm lineage-like cells described in the present disclosure, the starting population may be pluripotent stem cells (PSCs), such as iPSCs or ESCs. For instance, a population of cytotrophoblast-like cells described in the present disclosure can be described as being derived from PSCs. In another example, for a culture comprising syncytiotrophoblast-like structures, also described in this disclosure, the preceding population may be cytotrophoblast-like cells, which, in turn, may have been derived from PSCs. Thus, syncytiotrophoblast-like structures or a culture containing syncytiotrophoblast-like structures can be described as being derived from a culture or population of cytotrophoblast-like cells, and/or PSCs. In one more example, a culture or population comprising trophoblast stem-like cells described in the present disclosure, the preceding cell culture may have been a culture comprising syncytiotrophoblast-like structures, the preceding cell population of which may be cytotrophoblast-like cells, which, in turn, may have been derived from PSCs. Thus, trophoblast stem-like cells, as well as their culture or population, can be described as derived from syncytiotrophoblast-like structures or a culture containing syncytiotrophoblast-like structures, from a culture or population cytotrophoblast-like cells, and/or PSCs. Furthermore, in some embodiments extravillous trophoblast-like cells (EVTs) are derived from trophoblast stem-like cells, and therefore may also have been derived from syncytiotrophoblast-like structures or a culture containing syncytiotrophoblast-like structures, from a culture or population cytotrophoblast-like cells, and/or PSCs.

The term "comprising" and the related terms ("comprise," "comprises," etc.), when used in this disclosure to describe various embodiments of the invention, are open-ended, meaning that they do not exclude additional elements and synonymous with terms "including," "containing" or "having." When an embodiment of the invention is described using the term "comprising," it is intended to include the embodiments, in which the term comprising is replaced with the terms "consisting of" or "consisting essentially of" In other words, the description of the embodiments of the invention described in this disclosure using the term "comprising" and the related terms also provides the description of the related embodiments that use "consisting of" or "consisting essentially of" instead of "comprising". The term "consisting of" excludes any elements (steps, ingredient etc.) not specified in the description. The term "consisting essentially of" is intended to exclude only those elements not specified in the description that do not materially affect the basic and novel characteristics of the embodiment.

The terms "culture," "cell culture," "cell population" and related terms can be used to refer to a cell or a population of cells residing outside of an organism. These cells can be stem cells, primary cells isolated from an organism or obtained from a cell bank, animal, or blood bank, or secondary cells that are derived from the above sources. A primary cell includes any cell of an adult or fetal organism apart from egg cells, sperm cells and stem cells. Examples of useful primary cells include, but are not limited to, skin cells, bone cells, blood cells, cells of internal organs and cells of connective tissue. A secondary cell is derived from a primary cell or a stem cell and can be, in some instances, immortalized for long-lived in vitro cell culture. The term "population" can refer to a group of (more than one) cells having the same identifying characteristics. A cell culture or population can be described as "pure" when it contains a sufficiently high proportion of cells of a desired types or type and sufficiently low proportion of other types of cells. It is to be understood that "pure," when used in the present disclosure in the context of cell culture and related processes, is a relative and not an absolute term. For example, a cell culture and/or cell population can be described as "pure" when it contains over 50%, over 55%, over 60%, over 65%, over 70%, over 75%, over 80%, over 85%, over 90%, over 95%, or approximately 100% (for example, at least 95%, at least 96%, at least 97%, at least 98%, at least 99%) of a desired cell type or types.

The term "lineage," when used in reference to cells, encompasses all of the stages of the development of a cell type, from the earliest precursor cell to a completely mature cell (a specialized cell).

The terms "culture," "culturing," "grow," "growing," "maintain," "maintaining," "expand," "expanding," etc., when referring to cell, tissue or organ culture or the process of culturing, can be used interchangeably to mean that a cell or a group of cells (the scope of which expression includes groups or pluralities of undifferentiated or differentiated cells, embryos, embryoid bodes, tissues or organs) is maintained outside the body (ex vivo and/or in vitro) under conditions suitable for survival, proliferation, differentiation and/or avoiding senescence. In other words, cultured cell or groups of cells are allowed to survive, and culturing can result in cell growth, differentiation, or division. In this context, the terms "growing" and "culturing" can be used interchangeably and can refer to maintaining living cells in culture under certain conditions. The terms above do not imply that all cells in the culture survive or grow or divide, as some may naturally senesce. Cells are typically cultured in media, which can be changed during the course of the culture. The so-called two-dimensional (2D) cell cultures grow on flat surfaces, typically in plastic vessels that can be coated with substrates (for example, vitronectin, laminin 521, Matrigel, Geltrex). Three-dimensional (3D) cultures are cultures in which biological cells are permitted to grow or interact with their surroundings in all three dimensions. 3D cultures can be grown in in a variety of artificial environments, such as, but not limited to, plates, flasks, bioreactors or small capsules in which the cells can grow into spheroids or spheres. 3D cultures include so-called scaffold-free and scaffold-based technologies. Scaffold-free methods employ, but are not limited to, the uses of low adhesion plates, hanging drop plates, micropatterned surfaces, and rotating bioreactors, magnetic levitation, and magnetic 3D bioprinting. Scaffolds are structures or materials that provide a structural support for cell attachment and, in some cases, differentiation. Scaffolds include solid scaffolds, sponges (such as cellulose sponges), protein-based scaffolds (such as collagen or gelatin-based scaffolds), hydrogels, nanofiber scaffolds, synthetic polymer scaffolds (for example, polycaprolactone or polystyrene scaffolds). In general, a culture environment includes consideration of such factors as the substrate for cell growth, cell density and cell contract, the gas phase, the medium, and temperature. Cells in culture are generally maintained under conditions known to be optimal for cell growth. Such conditions may include, for example, a temperature of approximately 37° C. and a humidified atmosphere containing approximately 5% $CO_2$. The duration of the incubation can vary widely, depending on the desired results.

The terms "medium," "culture medium," "culture solution," "growth medium" and the related terms and expression refer to a medium supporting the survival and/or growth of cells (including single cells and pluralities of cells), tissues, organoids, organs or parts thereof or embryonic structures (such as, but not limited to, morula, blastocoel, blastocyst or embryo). A medium is typically isotonic, and can be a liquid, a colloidal liquid, a gel, a solid and/or a semi-solid. A medium can be configured to provide a matrix for cell adhesion or support, or a separate support (such as a culture vessel surface or a scaffold) can be provided. A medium can include the components for nutritional, chemical, and structural support necessary for culturing a cell or cells. A chemically defined medium (or "defined medium") is a medium with known concentrations of all of its chemical components. In contrast, an undefined medium can contain complex biological components, such as serum albumin or serum, that do not have completely defined compositions. A conditioned medium is understood to be a previously used medium from cultured cells. It contains metabolites, growth factors, and extracellular matrix proteins secreted into the medium by the cultured cells, which can be beneficial for subsequent uses of such conditioned medium. Culture medium can be provided in a powdered form to be prepared prior to use, in a concentrated form to be diluted prior to use, or in a form to be used without further dilution. For example, a culture medium can be a sterile liquid, supplied as a "working solution" to be used without further dilution, in which case the culture medium. A working solution of culture medium can contain effective amounts or concentrations of one or more additives. In another example, a culture medium can be a gel containing effective amounts of one or more additives. When a culture medium is provided in a form requiring further preparation, such as a powder or a concentrate, one or more can be included in amounts or concentration intended to provide an effective amount or amounts after the medium is prepared. For example, a 2x concentrated medium may contain twice the effective amount or amounts of one or more additives intended to be included in the final "working" form of the medium. Culture medium typically contains one or more appropriate nutrient sources for growth and/or maintenance of cells it is intended to support, such as mammalian cells, including human cells. Culture medium maintains appropriate pH and osmolarity. Culture medium can contain natural ingredients, artificial ingredients and/or synthetic ingredients. Examples of natural ingredients are biological fluids (such as plasma, serum, lymph or amniotic fluid), tissue extracts (such as extracts of liver, spleen, tumors, leukocytes, bone marrow or animal embryos). Some examples of culture media composed of artificial ingredients ("artificial media") are MEM and DMEM. Artificial culture medium can be serum-containing culture medium, serum-free culture medium (which can contain defined qualities of purified growth factors, lipoproteins and other components provided by the serum), chemically defined culture medium or protein-free culture medium. Culture medium can comprise one or more of a buffer, one or more inorganic salt, essential amino acids, one or more carbohydrate, such as glucose, fatty acids, lipids, vitamins and trace elements. One example of a buffer is a so-called natural (bicarbonate) buffering system, in which gaseous $CO_2$ balances with the $CO_3^{2-}/HCO^{3-}$ content of the culture. Another example is a chemical buffering system, such as the one using 4-(2-hydroxyethyl)-1-piperazineethanesulfonic acid (HEPES), a zwitterionic buffering agent. Culture medium can contain a pH indicator, such as phenol red, which allows pH monitoring during cell growth. Inorganic salt or salts in the culture media supply sodium, potassium and calcium ions, provide osmotic balance and help regulate cell membrane potential. Essential amino acids, which cannot be synthesized by the cells, are included in the culture medium, but nonessential amino acids may also be included to improve cell growth and viability. Carbohydrates, such as glucose, galactose, maltose or fructose are included as a source of energy. Proteins and peptides, such as albumin, transferrin or fibronectin may also be included, as well as fatty acids and lipids, particularly in serum-free media. Vitamins essential for growth and proliferation of cells, such as B group vitamins, can also be included. Examples of trace elements added to culture media, particularly serum free media, are copper, zinc, and selenium. Some examples of the culture media are commercially available media, such as, but not limited to, Essential 8 Medium, CTS Essential 8 Medium, Essential 6 Medium, StemFlex Medium, CTS KnockOut SR Xeno-free Medium, KnockOut Serum Replacement, StemPro, mTeSR, mTeSR1, StemFit, Nutristem, L7 Medium, iPS-Brew, Neurobasal or BrainPhys.

In the context of cell culture, the term "dissociating" can refer to a process of isolating cells from other cells or from a surface, such as a culture plate surface. For example, cells can be dissociated from an organ or a tissue by mechanical or enzymatic methods. In another example, cells that aggregate in vitro can be dissociated from each other. In yet another example, adherent cells are dissociated from a culture plate or other surface. Dissociation can involve breaking cell interactions with extracellular matrix (ECM) and substrates (for example, culture surfaces) or breaking the ECM between cells.

A "stem cell" is a cell characterized by the ability of self-renewal through mitotic cell division and the potential to differentiate into a tissue or an organ. Among stem cells, two main categories may be distinguished—embryonic and somatic stem cells. For example, mammalian embryonic stem cells may reside in the blastocyst and give rise to embryonic tissues, whereas somatic stem cells may reside in adult tissues for the purpose of tissue expansion, regeneration, and/or repair.

The term "cell line" typically refers to a cell culture developed from a single cell of a multicellular organism. Cells of a cell line have a relatively uniform genetic makeup. Some cell lines originate from stem cells. Some cell lines originate from naturally occurring cancerous cells that underwent genetic modifications (such as one or more mutations or introductions of viral genes) leading to uncontrolled proliferation. Some cell lines originate from the cells that have been artificially immortalized by various methods.

The term "stem cell" and the related terms and expressions are used herein to refer to animal cells that are capable of dividing and renewing themselves for long periods, are unspecialized, and can give rise to specialized cell types. Stem cells are capable of dividing and renewing themselves for long periods. Unlike, for example, muscle cells, blood cells, or nerve cells—which do not normally replicate themselves—stem cells may replicate many times or proliferate. If the resulting cells continue to be unspecialized, like the parent stem cells, the cells are said to be capable of long-term self-renewal.

The term "self-renewal," when used in reference to cells, describes their ability to divide and generate at least one daughter cell with the self-renewing characteristics of the parent cell, although one or more of other daughter cells may commit to a particular differentiation pathway. For example, a self-renewing hematopoietic stem cell can divide and form one daughter stem cell and another daughter cell committed to differentiation in the myeloid or lymphoid pathway ("asymmetric division"). Non self-renewing cells can still undergo cell division to produce daughter cells, neither of which have the differentiation potential of the parent cell type, but instead generates differentiated daughter cells.

The terms "pluripotent," "pluripotency" and the related terms and expressions refer to animal cells or cell populations with the ability to give rise to progeny that can undergo differentiation, under appropriate conditions, into cell types that collectively demonstrate characteristics associated with cell lineages from all of the three germ layers (endoderm, mesoderm, and ectoderm). For example, the expression "pluripotent stem cell characteristics" refers to characteristics of a cell or a cell population that distinguish pluripotent stem cells or their populations from other cells. The ability to give rise to progeny that can undergo differentiation, under the appropriate conditions, into cell types that collectively demonstrate characteristics associated with cell lineages from all of the three germ layers (endoderm, mesoderm, and ectoderm) is a pluripotent stem cell characteristic. Cell morphologies as well as expression or non-expression of certain combinations of molecular markers are also pluripotent stem cell characteristics. Pluripotent stem cells (PSCs) include embryonic stem cells (ESCs) and induced pluripotent stem cells (iPSCs). Embryonic stem cells (ESCs) are derived from embryos and, under appropriate conditions, they can remain undifferentiated (unspecialized) in culture. An embryonic stem cell line is a line of ESCs cultured under the conditions that allow proliferation without differentiation for months to years. Under other conditions, for example, if the cells are allowed to clump together to form embryoid bodies instead of forming a monolayer, they begin to differentiate spontaneously.

An "adult stem cell," which can also be termed "somatic stem cell," is a stem cell found, in an organism, among differentiated cells in a tissue or organ and can differentiate to yield some or all of the specialized cell times in the tissue or organ. Somatic stem cells can be grown in culture. When differentiating into specialized cells, they typically generate intermediate cells called "precursor" or "progenitor" cells. Somatic stem cells and progenitor cells can be described as "multipotent" or "oligopotent," depending on their degree of potency. Some examples of somatic stem cells are: hematopoietic stem cells that give rise to all the types of blood cells (red blood cells, B lymphocytes, T lymphocytes, natural killer cells, neutrophils, basophils, eosinophils, monocytes and macrophages); mesenchymal stem cells that include bone marrow stromal stem cells and skeletal stem cells and can give rise to bone cells (osteoblasts and osteocytes), cartilage cells (chondrocytes), fat cells (adipocytes), and stromal cells that support blood formation; neural stem cells that can give rise to nerve cells (neurons), astrocytes and oligodendrocytes; epithelial stem cells in the lining of the digestive tract that can give rise to absorptive cells, goblet cells, Paneth cells, and enteroendocrine cells; skin stem cells that occur in the basal layer of the epidermis (and can give rise to keratinocytes) and at the base of hair follicles (and can give rise to both the hair follicle and to the epidermis). A tissue-specific progenitor cell is a cell devoid of self-renewal potential that is committed to differentiate into cells of a specific organ or tissue. Certain somatic stem cell types can differentiate into cell types seen in organs or tissues other than those expected from the somatic stem cell's origin. This phenomenon is called "transdifferentiation."

The term "placenta" and related terms refer to a temporary vascular organ in mammals, which connects the umbilical cord of the developing fetus to the wall of maternal uterus, and mediates its metabolic exchange between the fetus and the maternal blood supply through association of placental tissues with uterine mucosa.

The term "trophectoderm" and related terms refer to the outer layer of cells of the human embryo starting at the stage of the blastocyst and until primary villi of the placenta are formed.

The term "trophectoderm lineage cell" and related terms refer to a cell that underwent a fate decision to acquire trophectodermal genotype and phenotype while steering away from any of the somatic lineages—ectoderm, mesoderm, endoderm.

The terms "cytotrophoblast," "cytotrophoblast cell" and related terms refer to a population of mononucleated cells within placental villi with stem cell and epithelial properties localized just below the syncytiotrophoblast. These cells have the capacity to create either syncytiotrophoblast by fusion or extravillous trophoblast cells that invade the endometrium and remodel the maternal spiral arteries. In some contexts, the term is used interchangeably with "trophoblast stem cell".

The term "syncytiotrophoblast" and related terms refer to multi-nucleated cells (which can be also be described as multinucleated structures) covering the surface of placental villi. Syncytiotrophoblasts are created by fusion of the underlying cytotrophoblast cells and represent the fetal side of the maternal-fetal interface. A distinct, early form of syncytiotrophoblast forms by fusion of trophectodermal cells in the blastocyst and facilitates implantation of the embryo into the maternal endometrium.

The term "trophoblast" and related terms refer to all the cells of the trophoblast lineage, which is one of the extra-embryonic lineages (and hence does not contribute directly to the cells of the fetal body). Extraembryonic lineage includes the early trophectoderm cells and trophoblast cells, both stem cell types and differentiated cell types. In some contexts, the term "trophoblast" is also used to encompass trophectoderm.

The term "trophoblast stem cell" and related terms refer to a cell of a subpopulation of trophoblast cells with stem cell properties and the ability to differentiate into either syncytiotrophoblast cells by fusion or extravillous trophoblast cells.

The expression "induced pluripotent stem cell" (iPSC) refers to a pluripotent stem cell artificially derived from a non-pluripotent cell. For example, human iPSCs are artificially derived from a human non-pluripotent cell. iPSCs can be derived by introducing products of specific sets of pluripotency-associated genes, or "reprogramming factors," into a given cell type and/or exposing non-pluripotent cells to particular conditions. The reprogramming factors are usually active only transiently until the cells acquire pluripotent characteristics.

The term "non-pluripotent cells" refer to mammalian cells that are not pluripotent cells. Examples of such cells include differentiated cells, somatic stem cells, as well as progenitor cells. Some non-pluripotent cells maintain a degree of potency, some of the examples being somatic stem cells and progenitor cells.

"Cell potency" describes a cell's ability to differentiate into other cell types. A cell can be designated as a pluripotent cell, a multipotent cell (which can differentiate into several but not all cell types, for example, umbilical cord blood stem cells and mesenchymal stem cells) or an oligopotent cell (having the ability to differentiate into a few cell types, for example, lymphoid cells or vascular cells). Under current understanding, potency exists on a continuum. Thusly, the boundaries between the divisions of cells based on potency may be fluid and are not necessarily limiting.

The terms "progenitor cell" or "precursor cell," as used herein, refers to the cells that can typically differentiate to form one or more kinds of cells. A "precursor cell" or "progenitor cell" can be any cell in a cell differentiation pathway that is capable of differentiating into a more mature cell. Progenitor cells can be primary cells obtained from an organism, cells proliferated in culture or cells derived from stem cells.

"Differentiation" is the process by which a less specialized cell becomes a more specialized cell type. For example, early development of a multicellular animal is characterized by the rapid proliferation of embryonic cells, which then differentiate to produce the many specialized types of cells that make up the tissues and organs of the multicellular animal. As cells differentiate, their rate of proliferation usually decreases. Some types of differentiated cells never divide again, but many differentiated cells are able to resume proliferation as required to replace cells that have been lost as a result of injury or cell death. Some cells divide continuously throughout life to replace cells that have a high rate of turnover in adult multicellular animals. Examples of differentiated cells are fibroblasts, hepatocytes, cardiomyocytes, myoblasts, neurons, osteoclasts, and lymphocytes.

The expression "modified cells" and the related terms and expressions encompass all cells that have been or are derived from the cells that have been artificially modified, by any methods, as compared to the original or cells from which they are derived. Modified cells can be produced from primary cells, secondary cells, stem cells, cultured cells and/or other modified cells. Modifications include, but are not limited to, genetic modification or engineering, in which case modified cells can be referred to as "genetically modified" or "genetically engineered." Genetic modification can be accomplished by various methods that result in incorporation of foreign or heterologous nucleic acids into the cells being modified. Some examples of such methods are transduction by a virus or a viral vector, or transfection of isolated nucleic acids into cells through transient pores in the cell membrane. Other modifications include exposing the source cells to biological and non-biological molecules or factors or culture conditions. Some examples of modified cells are iPSCs, genetically modified cells, including those used for gene therapies, one example being gene-edited cells, such as those modified using CRISPR/Cas9, TALENs or ZFNs.

The term "vessel" refers to a container, dish, plate, flask, bottle, cell culture tube, a bioreactor and the like, which can be used to culture, maintain or grow a cell, group of cells, tissue or organ ex vivo or in vitro. Suitable vessels include, for example, multi-well plates, wells of multi-well plates, dishes, tubes, flasks, bottles and reactors.

The terms "stabilize" and the related terms and expressions used in reference to cells (for example, "stabilizing a cell" or "stabilizing a cell population") refer to reduction of negative cell responses, such as cell death or senescence or unwanted differentiation (of stem cells). For example, stem cells and other cells can die in response to cell passaging, dissociation, isolation, freezing and/or thawing. In other words, the above conditions can reduce cell viability. Embodiments of the compositions, methods and kits described therein can mitigate the reduction of cell viability and improve cell survival, which can be described as cell stabilization.

The term "passage," "passaging" and the related terms and expressions used in the context of cell culture refer to subculturing, which typically involves transfer of cells from a previous culture into a fresh growth medium. Passaging is performed to ensure propagation of cells in culture. Cell proliferation in culture reduced or ceases when the cells reduce the capacity of the culture vessels and/or media to support further cell growth. For example, cells in adherent cultures may occupy all the available substrate and have no room left for expansion, while cells in suspension cultures exceed the capacity of the medium to support further growth. To keep cells in a culture at an optimal density for continued growth and to stimulate further proliferation, the culture must be expanded and fresh medium supplied. To divide the culture of adherent cells, for example, a monolayer culture of cells, such as cultures of differentiating PSCs described on the present disclosure, the cells are first dissociated, for example, by enzymatic dissociation. Enzymatic dissociation can be performed by removing the incubation medium from the plates, adding to the plates a buffer, such as PBS and an enzymatic dissociation reagent, such as Accutase, TrypLE or Trypsin (available, for example, from Thermo Fisher Scientific), incubating the cells with the buffer and dissociation reagent under appropriate conditions, and harvesting the resulting dissociated cells by centrifugation, sedimentation, filtering or other appropriate methods. The dissociated cells are transferred into similar or equivalent reaction vessels, such as flasks, with fresh media, to result in a lower cell density.

As used herein, "marker" refers to any molecule that can be observed or detected. For example, a marker can include, but is not limited to, a nucleic acid, such as a transcript of a specific gene, a polypeptide product of a gene, a non-gene product polypeptide, a glycoprotein, a carbohydrate, a glycolipid, a lipid, a lipoprotein or a small molecule (for example, molecules having a molecular weight of less than 10,000 AMU). When a presence, absence of amount of a marker can be experimentally observed or detected, such a marker or its amount can be described as "observable" or "detectable." The presence or absence of the markers, as applied to the embodiments of the preset invention, means detectable presence or absence of the markers as detected by applicable methods for detecting such markers, and may mean certain detectable or undetectable levels of such markers. In other words, the presence may mean the presence above a certain detectable level, while the absence may mean the absence below a certain detectable level and not necessarily zero detectable level. For most markers described herein, the symbols provided are those developed and/or recognized by HUGO Gene Nomenclature Committee of European Bioinformatics Institute.

In the context of observable or detectable markers, such as markers of cell development or differentiation, "expression" refers to the production of a gene product (which can be a nucleic acid, such as RNA, or a protein) as well as the level or amount of production of a gene product. Thus, determining the expression of a specific marker refers to detecting either the relative or absolute amount of the marker (which can mean detecting expression of RNA or protein) that is expressed or simply detecting (which can mean detecting expression of RNA or protein) the presence or absence of the marker. If expression of RNA or protein corresponding to the marker is detected, the marker can be said to be "detectably expressed." Expression of certain markers can be determined by detecting the presence or absence of the marker in cells, cell culture or cell population. Expression of certain markers can also be determined by measuring the level at which the marker is present in cells, cell culture or cell population. Quantitative, qualitative or semi-quantitative techniques can be used to measure marker expression. For example, marker expression can be detected and/or quantitated through the use of techniques detecting nucleic acids, such as PCR-based detection or RNA (for example, real-time reverse-transcriptase PCR), RNA sequencing (RNA-seq), or RNA detection by nucleic acid array-based techniques. In another example, immunochemistry can be used to detect and/or quantitate marker proteins.

For example, the expression of a marker gene product can be detected by using antibodies specific for the marker gene product of interest using Western blotting, immunocytochemical characterization, flow cytometry analysis, etc. Various techniques of marker detection can be used in in conjunction to effectively and accurately characterize and identify cell types and determine both the amount and relative proportions of such markers in a subject cell type. The expression of certain markers can be determined by measuring the level at which the marker is present in the cells of the cell culture or cell population as compared to a standardized or normalized control marker. Identification and characterization of cells, cell cultures or cell population can be based on expression of a certain marker or different expression levels and patterns of more than one marker (including the presence or absence, the high or low expression, of one or more the markers). Also, certain markers can have transient expression, when the marker exhibits higher expression during one or more stages of the processes described in this disclosure and lower expression during other stage or stages.

The term "cryopreservation," as well as related terms and expression, are used to refer to is a process or processes, as well as the results of such process or processes, by which cells, groups of cells or cell cultures are preserved by cooling to sub-zero temperatures.

Methods

Various methods (processes) are envisioned and included among the embodiments of the present invention. Among the methods according to embodiments of the present invention are methods of producing in culture of cells or cell cultures containing cells with at least some defined characteristics. Such methods can also be referred to "methods of cell production," "method of cell culture production," "methods of generating," "methods of culturing," "methods of differentiating," "differentiation method," "differentiation process" and by other related terms and phrases, which can be used in reference to methods of producing trophectoderm-lineage cells or cell cultures described in the present disclosure. The methods described in the present disclosure are conducted in culture, and can be referred to as "methods of producing cells (or cell populations) in culture" or "culturing methods." Some embodiments of the methods described in the present disclosure proceed from, as starting materials or intermediate products, less differentiated cells possessing higher potency (such as pluripotent cells, progenitor cells, multipotent cells or oligopotent cells) and proceed to, as intermediate and/or end products, more differentiated cells with lower potency (such as multipotent cells, progenitor cells, oligopotent cells or differentiated cells). Accordingly, some embodiments of the methods described in the present disclosure can be referred to as "methods of differentiating cells," even if the end product is or contains the cells that are not completely differentiated.

One example of a method according to embodiments of the present invention is a method of producing or generating cytotrophoblast-like cells, cultures including cytotrophoblast-like cells, or populations including cytotrophoblast-like cells. Cytotrophoblast-like cells produced by the methods according to the embodiments of the present invention exhibit at least some characteristics of naturally occurring cytotrophoblasts, such as the ability to store glycogen in cytoplasm, and/or expression of one or more of cytotrophoblast-associated markers, for example, Caudal Type Homeobox Protein 2 (CDX2; Ensembl Gene ID: ENSG00000165556), GATA Binding Protein 3 (GATA3; Ensembl Gene ID: ENSG00000179348), Keratin 7 (KRT7;

Ensembl Gene ID: ENSG00000148773), Keratin 18 (KRT18; Ensembl Gene ID: ENSG00000111057), Transcription Factor AP-2 Alpha (TFAP2A; Ensembl Gene ID: ENSG00000137203), or Insulin Like Growth Factor Binding Protein 3 (IGFBP3; Ensembl Gene ID: ENSG00000146674). Cytotrophoblast-like cells can be referred to as "cells exhibiting at least some characteristics of cytotrophoblast cells," "cells exhibiting at least some characteristics of cytotrophoblasts," "cells resembling cytotrophoblasts" and by other related terms and expressions. Cytotrophoblast-like cells and their cultures are also discussed elsewhere in this disclosure.

One more example of a method according to embodiments of the present invention is a method of producing or generating syncytiotrophoblast-like structures, cultures including syncytiotrophoblast-like structures, or cell populations including syncytiotrophoblast-like structures. Syncytiotrophoblast-like structures produced by the methods according to the embodiments of the present invention exhibit at least some characteristics of naturally occurring syncytiotrophoblasts, such as being a muti-nucleated syncytium (meaning a multinucleated cell or structure), and/or expression of one or more of syncytiotrophoblast-associated markers, such as Distal-Less Homeobox 3 (DLX3; Ensembl Gene ID: ENSG00000064195), Glycoprotein Hormones, Alpha Polypeptide (CGA; Ensembl Gene ID: ENSG00000135346); GATA3, KRT7, DAB Adaptor Protein 2 (DAB2; Ensembl Gene ID: ENSG00000153071), TEA Domain Transcription Factor 3 (TEAD3; Ensembl Gene ID: ENSG00000007866), or Transcription Factor AP-2 Gamma (TFAP2C; Ensembl Gene ID: ENSG00000087510). Syncytiotrophoblast-like structures produced according to the embodiments of the methods of the present invention can also be referred to as "syncytiotrophoblast-like cells," "cells resembling syncytiotrophoblasts," "structures resembling syncytiotrophoblasts" and by other related terms and expressions. Syncytiotrophoblast-like structures are also discussed elsewhere in this disclosure.

One more example of a method according to embodiments of the present invention is a method of producing or generating trophoblast stem cell-like cells, populations including trophoblast stem cell-like cells, or cultures including trophoblast stem cell-like cells. Trophoblast stem cell-like cells produced by the methods according to the embodiments of the present invention exhibit at least some characteristics of naturally occurring trophoblast stem cells, such as a capacity for self-renewal, expression of the proliferation marker Ki-67 (also known as MKI67 protein), and/or expression of one or more of trophoblast-associated markers, such as E74 Like ETS Transcription Factor 5 (ELF5; Ensembl Gene ID: ENSG00000135374), GATA3, CDX2, TFAP2C, KRT7, and Yes Associated Protein 1 (YAP1; ENSG00000137693). Trophoblast stem cell-like cells structures produced according to the embodiments of the methods of the present invention can also be referred to as "cells resembling trophoblast stem cells." Trophoblast stem cell-like cells are discussed further in this disclosure.

Yet another example of a method according to embodiments of the present invention is a method of producing or generating extravillous trophoblast-like cells (EVT), populations including extravillous trophoblast-like cells, or cultures including extravillous trophoblast-like cells. Extravillous trophoblast-like cells produced by the methods according to the embodiments of the present invention exhibit at least some characteristics of naturally occurring extravillous trophoblast cells, such as acquisition of morphology associated with epithelial-to-mesenchymal transition as indicated by epithelial TSCs differentiating into elongated, spindle-shaped EVT, and/or expression of one or more of extravillous trophoblast-associated markers, such as HLA-G (Ensembl Gene ID: ENSG00000204632), MMP2 (ENSG00000087245) and MFAP5 (ENSG00000197614). Extravillous trophoblast-like cells produced according to the embodiments of the methods of the present invention can also be referred to as "cells resembling extravillous tropho-blast cells." Extravillous trophoblast-like cells are discussed further in this disclosure.

In some exemplary embodiments, the methods described in the present disclosure use pluripotent stem cells (PSCs) as a starting material. Such PSCs can be mammalian PSCs, including non-human mammalian PSCs or human PSCs (hPSCs). PSCs used in the methods according to the embodiments of the present invention can be isolated from natural sources or artificially derived PSCs, such as induced PSCs (iPSCs). Accordingly, the methods can be referred to as "methods of differentiating PSCs," for example, methods of differentiating hPSCs, methods of differentiating PSCs, etc. PSCs can be maintained and expanded in culture, such as monolayer culture or appropriate 3D culture systems (for example, those using microcarriers) in a defined medium, such as, but not limited to, E8, E8 Flex, StemFlex, StemPro, mTeSR, mTeSR1, StemFit, Nutristem, L7 Medium or iPS-Brew. The above maintenance and/or expansion of PSCs can be conducted as a part of the methods according to the embodiments of the present invention, or outside of such methods. In other words, cell production methods according to the embodiments of the present invention are not limited by the steps or processes employed to provide PSCs used for further steps, unless such limitations are explicitly stated. For example, if PSCs are simply listed as a starting material or "provided" without further limitations, then the processes used to obtain, culture, expand or grow PSCs are not intended to be incorporated into the method. PSCs can be provided in the form of monolayer cultures exhibiting, for example, typical PSC morphology, which may include prominent nucleoli and/or high nuclear-to-cytoplasmic ratio, cell growth in colonies, and expression of pluripotency-associated markers such as, but not limited to, POU Class 5 Homeobox 1 protein (POU5F1 or OCT4; Ensembl Gene ID: ENSG00000204531), Nanog homeobox protein (NANOG; Ensembl Gene ID: ENSG00000111704), SSEA-4 (A4GALT, Ensembl Gene ID: ENSG00000128274), Podo-calyxin (PODXL; Ensembl Gene ID: ENSG00000128567), and/or Alkaline Phosphatase (ALPL; Ensembl Gene ID: ENSG00000162551; SSEA-4—official gene symbol: A4GALT, Ensembl Gene ID: ENSG00000128274). In another example, PSCs can be provided in the form of 3D cultures or attached to microcarriers.

Cell production methods according to the embodiments of the present invention can include a step of plating mamma-lian PSCs (which can be ESCs or iPSCs), such as human PSCs, for example, human iPSCs, on a coated surface of a culture vessel (for example, a vitronectin-coated or laminin-coated surface) at a density needed to achieve a confluence of approximately 25-50% after approximately 12-24 hours of incubating PSCs in a first culture medium, which can also be referred to as "PSC incubation medium" or "incubation medium," and is discussed elsewhere in the present disclo-sure. Some embodiments of the cell production methods may not include the plating step. In such embodiments, the PSCs may be provided at the start of a method as an adherent monolayer culture of a density needed to achieve a conflu-ence of approximately 25-50% after approximately 12-24 hours of incubating PSCs in the first culture medium. Some embodiments of the cell production methods may include a step of dissociating PSCs prior to plating. Dissociation of PSCs can be accomplished by various methods, such as, but not limited to, association by incubating PSCs in ethylene-diaminetetraacetic acid (EDTA), or dissociation by incubat-ing PSC in a solution of proteolytic enzymes.

Cell production methods according to the embodiments of the present invention can include a step of incubating plated mammalian PSCs (which can be ESCs or iPSCs), such as human PSCs, for example, human iPSCs, in a first culture medium. The first culture medium can be a defined culture medium (in which case it can be referred to as "first defined culture medium" or "defined incubation medium"), although using other types of media is also envisioned. Some non-limiting examples of the defined media suitable for incubat-ing PSCs are E8, E8 Flex, StemFlex, mTeSR, StemFit, or mouse embryonic fibroblast (MEF)-conditioned medium. The first culture medium can contain optional additives. In an exemplary embodiment, the medium contains Chroman 1 or a derivative thereof at about 4 nM to about 80 μM, Emricasan or a derivative thereof at about 100 nM to about 80 μM, trans-ISRIB at about 50 nM to about 80 μM, and putrescine, spermine and spermidine (collective referred to as "polyamines" is each at a concentration of about 0.5 nM to 1 mM. The above combination of Chroman 1 or derivative thereof, Emricasan or a derivative thereof, trans-ISRIB and polyamines can be referred to as "CEPT." In an exemplary embodiment, the medium is E8. A period of time for incubating the plated PSCs is approximately 12 to approxi-mately 24 hours, for example, from 12 hours±1.2 hours to 24 hours±2.4 hours, such as 12, 13, 14, 15, 16, 17, 18, 19, 20, 21, 22, 23 or 24 hours.

In the embodiments of cell production methods including a step of incubating PSCs in a first culture medium, after the above incubation step is completed, the first culture medium in the PSC culture is replaced with a culture medium (which can be referred to as "second culture medium" or "first differentiation medium") containing an effective amount or concentration of: one or more inhibitors of transforming growth factor beta (TGF-beta) signaling, an effective amount or concentration of first one or more activators of Wnt signaling, an effective amount or concentration of one or more inhibitors of fibroblast growth factor (FGF) receptor signaling, an effective amount or concentration of bone morphogenic protein 4 (BMP4), and an effective amount or concentration of bone morphogenic protein 10 (BMP10). Some examples of suitable inhibitors of TGF-beta signaling that may be included in the second culture medium are 10 nM-100 μM A83-01 or 10 nM-100 μM SB 431542. Some examples of suitable activators of Wnt signaling that may be included in the second culture medium are 10 nM-100 μM CHIR99021 or 5 nM-100 μM CHIR98014. Some examples of suitable inhibitors of FGF receptor signaling that may be included in the second culture medium are 10 nM-50 μM CH5183284, 10 nM-100 μM PD-166866, or 10 nM-100 μM PD-173074. In one embodiment, the second culture medium comprises 10 nM-100 μM A83-01, 10 nM-100 μM CHIR99021, 10 nM-50 μM CH5183284, 5 to 200 ng/ml of BMP4, and 5 to 200 ng/ml of BMP10. For example, the second culture medium can comprise approximately 2 μM A83-01, approximately 600 nM CHIR99021, approximately 500 nM CH5183284, approximately 50 ng/ml of BMP4, and approximately 50 ng/ml of BMP10. The second culture medium can be a defined culture medium (in which case it can be referred to as "second defined culture medium" or "first defined differentiation medium"), although using other types of media is also envisioned. Some non-limiting examples of the suitable defined media are DMEM-F12, E6, Neurobasal medium, or Minimum Essential Medium (MEM).

Mammalian PSCs (which can be ESCs or iPSCs), such as human PSCs, for example, human iPSCs, are cultured in the second culture medium for approximately 24-96 hours, for example, from 30 hours±6 hours to 90 hours±6 hours, such as 36-90 hours, 48-84 hours, 60-78 hours, or 72 hours±7 hours. During the culturing in the second culture medium, the medium can be changed approximately every 20-28 hours, for example, from every 20±2 hours to every 28±3 hours, such as approximately every 20, 21, 22, 23, 24, 25, 26, 27 or 28 hours. In some embodiments of the cell production methods, the cells are not passaged during the culturing in the second culture medium. The culturing of mammalian PSCs (which can be ESCs or iPSCs), such as human PSCs, for example, human iPSCs, in the second culture medium induces or initiates differentiation of the PSCs. Accordingly, the cells exhibit donwnregulation of pluripotency-associated markers, such as OCT4. For example, at the end of the step of culturing in the second culture medium, expression of OCT4 in the cells can be detectably silenced, thereby indicating their exit from pluripotency. During the culturing in the second culture medium, it is appropriate to refer to the cells as differentiating, such as differentiating mammalian (for example, human) PSCs. Cytorophoblast-like cells, which can be characterized by detectable expression of one or more cytoro-phoblast-associated markers arise (appear) in the culture being cultured in the second culture medium at various time points after the start of the culturing. For example, cytotro-phoblast-like arise (appear) in cell cultured according to some embodiments of the methods described in the present disclosure at approximately 48-120 hours after the start of culturing of pluripotent cells in the second culture medium, as indicated by upregulated expression of one or more cytotrophoblast-associated markers. At the end of culturing in the second culture medium, the cell culture contains approximately 50%-100% of cytotrophoblast-like cells. For example, at the end of culturing in the second culture medium, the culture can contain approximately 50%, approximately 60%, approximately 70%, approximately 80%, approximately 90% or over 90% (such as approximately 91%, 92%, 93%, 94%, 95%, 96%, 97%, 98%, 99%, or 100%) of cytotrophoblast-like cells. At the end of culturing in the second culture medium, the cell culture can be referred to as a culture or population of cytotrophoblast-like cells, even if not all of the cells in the culture or population are cytotrophoblast-like cells. During subsequent step or steps (discussed elsewhere in this disclosure) of the cell production methods according to the embodiments of the present invention, cytotrophoblast-like cells are capable of producing syncytiotrophoblast-like structures and tropho-blast stem cell-like cells.

Cytotrophoblast-like cells or their cultures, or populations can be the end product of some, but not all, of the methods of cell production according to the embodiments of the present invention. Cytotrophoblast-like cells or their cultures, or populations can be an intermediate of some of the methods according to embodiments of the present invention, and can also be a starting material according to some other methods according to the embodiments of the present invention. For example, cytotrophoblast-like cells produced by culturing mammalian PSCs in the second culture medium, are capable of producing syncytiotrophoblast-like structures and trophoblast stem cell-like cells, when subjected to the method steps described further in this disclosure. In these situations, cytotrophoblast-like cells can be described as intermediates of embodiments of cell production methods. In another example, cytotrophoblast-like cells can be prepared for cryopreservation and cryopreserved. The method steps related to cryopreservation can be incorporated into the methods of cell production according to the embodiments of the present invention. Some of the methods and compositions relevant to cryopreservation are described further in this application in the section "Cryopreservation," although it is to be understood that the description provided in that section is not limiting, and that other compositions and methods can be employed for cryopreservation.

A population of cytotrophoblast-like cells is capable of generating, under appropriate conditions, structures exhibiting at least some characteristics of syncytiotrophoblasts. Methods of producing, in culture, of syncytiotrophoblast-like structures are included among the embodiments of the present invention. In some embodiments, mammalian PSCs can be a starting materials of such methods, which may then include a step of culturing PSCs in the second culture medium discussed elsewhere in the present disclosure. Cyto-trophoblast-like cells, or cultures including such cells can be a starting material or intermediate of producing syncytio-trophoblast-like structures in culture. In one example, PSCs are cultured under conditions inducing their differentiation into cytotrophoblast-like cells, cytotrophoblast-like cells are cultured under conditions inducing their conversion into syncytiotrophoblast-like structures. In this situation, cyto-trophoblast-like cells, or cultures including such cells can be described as an intermediate of producing syncytiotropho-blast-like structures in culture. Accordingly, embodiments of methods of producing syncytiotrophoblast-like structures can include one or more steps of producing cytotrophoblast-like cells in culture according to the embodiments of the present invention. In some other examples, embodiments of methods of producing syncytiotrophoblast-like structures or cultures including syncytiotrophoblast-like structures do not need to include steps of producing cytotrophoblast cells, which can simply be provided at the start of the method of producing syncytiotrophoblast-like structures. In such situation, cytotrophoblast-like cells, or cultures including such cells can be described as a starting material for producing syncytiotrophoblast-like structures in culture.

In an embodiment of a method of producing syncytiotro-phoblast-like structures that includes one or more steps of producing cytotrophoblast-like cells in culture according to the embodiments of the present invention, after the step of culturing in the second culture medium, the second culture medium in the culture is replaced with a culture medium (which can be referred to as "third culture medium" or "second differentiation medium"). An embodiment of a method of producing syncytiotrophoblast-like structures can also start with a step of culturing cytotrophoblast-like cells in a third culture medium. The third culture medium contains an effective amount or concentration of: one or more inhibitors of TGF-beta signaling, and an effective amount or concentration of one or more activators of Wnt signaling. One or more inhibitors of TGF-beta signaling including in the third culture medium can be same or different than the one or more inhibitors of TGF-beta signaling included in the second culture medium. One or more activators of Wnt signaling included in the third culture medium can be same or different than the one or more activators of Wnt signaling included in the second culture medium. Some examples of suitable inhibitors of TGF-beta signaling that may be included in the third culture medium are 10 nM-100 μM A83-01 or 10 nM-100 μM SB 431542. Some examples of suitable activators of Wnt signaling that may be included in the third culture medium are 10 nM-100 μM CHIR99021 or 5 nM-100 μM CHIR98014. In one embodiment, the third culture medium comprises 10 nM-100 μM A83-01 and 10 nM-100 μM CHIR99021. For example, the third culture medium can comprise approximately 2 μM A83-01 and approximately 600 nM CHIR99021. The third culture medium can be a defined culture medium (in which case it can be referred to as "third defined culture medium" or "second defined differentiation medium"), although using other types of media is also envisioned. Some non-limiting examples of the suitable defined media are DMEM-F12, E6, Neurobasal medium, Minimum Essential Medium (MEM), or BrainPhys neuronal medium. The cells are cultured in the third culture medium for approximately 168-312 hours, for example, from 180 hours±12 hours to 300 hours±12 hours, such as 180-300 hours, 192-288 hours, 204-276 hours or 216-264 hours, for example, approximately 168, 180, 192, 204, 216, 228, 240, 252, 264, 276, 288, 300, or 312 hours. During the culturing in the third culture medium, the cells being cultured are not passaged. During the culturing in the third culture medium, syncytiotrophoblast-like structures are formed in the culture, meaning multinucleated structures expressing syncytiotrophoblast-associated markers. In some cases, after approximately 168 hours of culturing in the third culture medium, at least approximately 5% of the total detectable nuclei in the culture appear to be embedded syncytiotrophoblast-associated markers. At the end of culturing in the second culture medium, the culture can contain a mixture of cytotrophoblast-like cells and syncytiotrophoblast-like structures.

A population of cells including syncytiotrophoblast-like structures is capable of generating, under appropriate conditions, a cell population containing trophoblast stem-like cells. Methods of producing, in culture, of trophoblast stem-like cells, cultures including trophoblast stem-like cells, or cell populations including trophoblast stem-like cells are included among the embodiments of the present invention. In some embodiments, mammalian PSCs can be a starting materials of such methods, which may then include a step of culturing PSCs in the second culture medium discussed elsewhere in the present disclosure. Cytotrophoblast-like cells, or cultures including such cells can be a starting material or intermediate of producing, in culture, trophoblast stem-like cells, cultures including trophoblast stem-like cells, or cell populations including trophoblast stem-like cells. Syncytiotrophoblast-like structures, or cultures including syncytiotrophoblast-like structures can be a starting material or intermediate of producing, in culture, trophoblast stem-like cells, cultures including trophoblast stem-like cells, or including populations trophoblast stem-like cells. In one example, PSCs are cultured under conditions inducing their differentiation into cytotrophoblast-like cells, cytotrophoblast-like cells are cultured under conditions inducing their conversion into syncytiotrophoblast-like structures, and a cell culture including syncytiotrophoblast-like structures is then cultured under conditions leading to appearance of trophoblast stem-like cells. In this situation, cytotrophoblast-like cells, or cultures including such cells, as well as syncytiotrophoblast-like structures, or cultures including syncytiotrophoblast-like structures can be described as intermediates of producing trophoblast stem cell-like cells in culture. Accordingly, embodiments of methods of producing trophoblast stem cell-like cells can include one or more steps of producing cytotrophoblast-like cells in culture, and/or one or more steps of producing syncytiotrophoblast-like structures. In some other examples, embodiments of methods of producing trophoblast stem cell-like cells or cultures including trophoblast stem cell-like cells do not need to include steps of producing cytotrophoblast cells, which can simply be provided at the start of the method of producing trophoblast stem cell-like cells structures. In such situation, cytotrophoblast-like cells, or cultures including such cells can be described as a starting material for producing trophoblast stem cell-like cells in culture. In yet some other examples, embodiments of methods of producing trophoblast stem cell-like cells or cultures including trophoblast stem cell-like cells do not need to include steps of producing syncytiotrophoblast-like structures or cultures including syncytiotrophoblast-like structures, which can simply be provided at the start of the method of producing trophoblast stem cell-like cells structures. In such situation, syncytiotrophoblast-like structures, or cultures including syncytiotrophoblast-like structures can be described as a starting material for producing trophoblast stem cell-like cells in culture. Trophoblast stem-like cells or populations including trophoblast stem-like cells generated according to embodiments of the methods described in the present disclosure can be prepared for cryopreservation and cryopreserved. The method steps related to cryopreservation can be incorporated into the methods of producing trophoblast stem-like cells or populations including trophoblast stem-like cells according to the embodiments of the present invention. Some of the methods and compositions relevant to cryopreservation are described further in this application in the section "Cryopreservation," although is to be understood that the description provided that section is not limiting, and that other compositions and methods can be employed for cryopreservation.

In an embodiment of a method of producing trophoblast stem-like cells that includes one or more steps of producing syncytiotrophoblast-like structures in culture according to the embodiments of the present invention, after the step of culturing in the third culture medium, the third culture medium in the culture is replaced with a culture medium (which can be referred to as "fourth culture medium" or "proliferation medium." Alternatively, an embodiment of a method of producing trophoblast stem-like cells or cultures containing trophoblast stem-like cells can start with a step of culturing cytotrophoblast-like cells in a fourth culture medium. The fourth culture medium contains an effective amount or concentration of: one or more inhibitors of TGF-beta signaling, an effective amount or concentration of one or more activators of Wnt signaling, an effective amount or concentration of Hepatocyte Growth Factor (HGF) (for example, 5-500 ng/ml of HGF), an effective amount or concentration of Epidermal Growth Factor (EGF) (for example, 5-500 ng/ml of EGF), an effective amount or concentration of Roof Plate-Specific Spondin 1 (R-spondin 1) (for example, 50-500 ng/ml of R-spondin 1), an effective amount of concentration of Roof Plate-Specific Spondin 3 (R-spondin 3) (for example, 5-500 ng/ml of R-spondin 3), an effective amount of concentration of Prostaglandin $E_2$ (for example, 5 nM-100 μM Prostaglandin $E_2$), and an effective amount or concentration of one or more ROCK inhibitors or one or more inhibitors of myosin II ATPase. In some embodiments, in addition to the above-listed additives, the fourth culture medium included an effective amount or concentration of CEPT (meaning that CEPT is an optional additive). One or more inhibitors of TGF-beta signaling including in the fourth culture medium can be same or different than the one or more inhibitors of TGF-beta signaling included in the second and/or the third culture media. One or more activators of Wnt signaling included in the fourth culture medium can be same or different than the one or more activators of Wnt signaling included in the second and/or the third culture media. Some examples of suitable inhibitors of TGF-beta signaling that may be included in the fourth culture medium are 10 nM-100 μM A83-01 or 10 nM-100 μM SB 431542. Some examples of suitable activators of Wnt signaling that may be included in the fourth culture medium are 10 nM-100 μM CHIR99021 or 5 nM-50 μM CHIR98014. Some examples of suitable ROCK inhibitors that may be included in the fourth culture medium are 4 nM-80 Chroman 1, 5 nM-100 μM Thiazovivin, or 5 nM-100 μM GSL 269962. An example of a suitable inhibitor of myosin II ATPase that may be included in the fourth culture medium is 10 nM-100 μM blebbistatin. In one embodiment, the fourth culture medium comprises 10 nM-100 μM CHIR99021, 5 nM-50 μM CHIR98014, 10 nM-100 μM A83-01 or 10 nM-100 μM SB 431542, 5-500 ng/ml of HGF, 5-500 ng/ml of EGF, 50-500 ng/ml of R-spondin 1, 5-500 ng/ml of R-spondin 3, 5 nM-100 μM Prostaglandin E$_2$, and 4 nM-80 μM Chroman 1. For example, the second culture medium can comprise approximately 2 μM A83-01, approximately 600 nM CHIR99021, approximately 300 nM CHIR98014, approximately 100 ng/ml of HGF, approximately 100 ng/ml of EGF, approximately 80 ng/ml of R-spondin 1, approximately 50 ng/ml of R-spondin 3, approximately 2.5 μM Prostaglandin E$_2$, and approximately 25 nM Chroman 1 The fourth culture medium can be a defined culture medium (in which case it can be referred to as "third defined culture medium" or "second defined differentiation medium"), although using other types of media is also envisioned. Some non-limiting examples of the suitable defined media are DMEM-F12, E6, Neurobasal medium, Minimum Essential Medium (MEM), or BrainPhys neuronal medium. During the culturing in the fourth culture medium, trophoblast stem-like cells emerge in the culture very soon after the replacement of the third culture medium with the fourth culture medium. Trophoblast stem-like cells form colonies and show a distinct morphology, with prominent nucleoli and dark cytoplasm. Due to the self-renewing properties of trophoblast stem-like cells, they can be cultured in the fourth culture medium indefinitely, provided they are passaged when they become confluent. The passaging can be performed at 1:3 to 1:5 ratio (such as 1:3, 1:3.5, 1:4, 1:4.5, or 1:5 ratio) of confluent cell culture to fresh medium. For example, the cells can be passaged approximately every 3-6 days.

Automation

Automated methods of cell culture are included among the embodiments of the present invention. Also included among the embodiments of the present invention are systems for performing or partially performing embodiments of the automated methods of the present invention. The systems according to the embodiments of the present invention may include various stations and/or components, some examples of which are described below. As used herein, the term "station" is broadly defined and includes any suitable apparatus or assemblies, conglomerations or collections of apparatuses or components suitable for carrying out a method according to the embodiments of the present invention. The stations need not be integrally connected or situated with respect to each other in any particular way. Systems according to the embodiments of the present invention may include any suitable arrangements of the stations with respect to each other. For example, the stations need not even be in the same room. But in some embodiments, the stations are connected to each other in an integral unit.

Automated cell culture methods and system for performing various methods according to embodiments of the present invention may be used to optimize conditions of various method steps and/or and to scale up production of cells produced by the methods, such us trophectoderm-like cells and/or trophoblast stem-like cells. In general, automated methods and systems according to the embodiments of the present invention minimize human intervention needed during cell culture procedures such as feeding, passing or harvesting of cells. In addition to freeing up laboratory personnel, the disclosed automated methods and systems allow for these techniques to be carried out in a reliable and reproducible manner. For example, a system for performing various methods according to embodiments of the present invention may include a station for robotic or automated cell culture, one example of which is CompacT SelecT® (Sartorius, Wilmington, DE) system. An automated cell culture system can grow, expand, and differentiate cells by performing methods according to the embodiments of the present invention. An automated cell culture system may be able to perform one or more steps required for cryopreservation of cells. An automated cell culture system can perform one or more cell culture processes, such as, but not limited to, seeding cell culture flasks or plates, maintaining cell cultures, for example, in cell culture flasks or plates, harvesting cells, pooling cells from harvesting flasks or plates, diluting cells for sub-culturing an plating, conducting cell counts, conducting cell viability assays, etc. An automated cell culture systems can include various stations, such as, but not limited to: a station for incubating cells, which is exemplified by an automated flask incubator maintaining a controlled environment (including controlled temperature, controlled gas composition and/or aseptic environment maintenance); a station for handling of flasks and other cell culture instruments, such as pipettes, which can be exemplified by a robotic arm or other type of robotic handler); a station for reagent dispensing, such as a robotic low volume dispenser; etc.

An automated cell culture system can include various computer components. An automated cell culture system embodiment, or parts of the system, may be controlled by a computer. For example, an automated cell culture system may include a computer-based station for generating reports. An automated cell culture system may include a computer-based station or components for data analysis. An automated cell culture system may include a computer, a processor, electronic memory, software instructions etc. An automated cell culture system may include software instructions for one or more of: system operation, workflow optimization, auditing and/or tracking of cell culture flasks or plates, etc. For example, an automated cell culture system may include an application software program to run programmed protocols on the robotic liquid handling system. The software program may run on an external device (for example, a portable computer, such as a tablet computer or a smartphone) which is in communication with a controller built into the robotic liquid handling system; the software program in some embodiments may coordinate control of the robotic liquid handling system and, when present, the external robotic system as well, to implement at least some steps of the methods according to the embodiments of the present invention. The software program may be programmed to alert users, for example, using sound, light, vibration, email alerts, text alerts, when intervention is needed, either due to a fault/error or due to a procedure being completed.

Computer-Based Calculations and Tools

The methods described in this disclosure can involve computer-based calculations and tools. Tools can be advantageously provided in the form of computer programs that are executable by a general-purpose computer system (which can be called "host computer") of conventional design. The host computer may be configured with many different hardware components and can be made in many dimensions and styles (for example, desktop PC, laptop, tablet PC, handheld computer, server, workstation, mainframe). Standard components, such as monitors, keyboards, disk drives, CD and/or DVD drives, and the like, may be included. Where the host computer is attached to a network, the connections may be provided via any suitable transport media (e.g., wired, optical, and/or wireless media) and any suitable communication protocol (e.g., TCP/IP); the host computer may include suitable networking hardware (e.g., modem, Ethernet card, WiFi card). The host computer may implement any of a variety of operating systems, including UNIX, Linux, Microsoft Windows, MacOS, or any other operating system.

Computer code for implementing aspects of the present invention may be written in a variety of languages, including PERL, C, C++, Java, JavaScript, VBScript, AWK, or any other scripting or programming language that can be executed on the host computer or that can be compiled to execute on the host computer. Code may also be written or distributed in low level languages such as assembler languages or machine languages.

The host computer system advantageously provides an interface via which the user controls operation of the tools. In the examples described herein, software tools are implemented as scripts (for example, using PERL), execution of which can be initiated by a user from a standard command line interface of an operating system such as Linux or UNIX. Commands can be adapted to the operating system as appropriate. In other embodiments, a graphical user interface may be provided, allowing the user to control operations using a pointing device. Thus, the present invention is not limited to any particular user interface.

Scripts or programs incorporating various features of the present invention may be encoded on various computer readable media for storage and/or transmission. Examples of suitable media include magnetic disk or tape, optical storage media such as compact disk (CD) or DVD (digital versatile disk), flash memory, and carrier signals adapted for transmission via wired, optical, and/or wireless networks conforming to a variety of protocols, including the Internet.

Additives

Various additives can be used in the methods of cell production according to the embodiments of the present invention and in the related compositions and kits. Some additives and/or additive components are discussed below for clarity. It is understood that other additive and/or additive components may be used, even if they are not discussed below. In the context of the embodiments of the present invention, each of the components separately or a combination of components, can be referred to as "additive," "supplement," "active agent" or by other related terms, in singular or plural. Various formulations of the additives are envisioned. For example, additives can be formulated to contain amounts of one or more active agents sufficient to provide effective concentrations or effective amounts of the respective active agent or agents upon addition to culture media. In the context of the embodiment of the present invention, effective concentrations or effective amounts are those concentrations or amounts, respectively, of the one or more active agents that elicit desired effects on the cells exposed to the compositions, such as, but not limited to, improved survival (viability), cell stabilization, improved growth, reduced cell death, reduced senescence, improved growth, improved differentiation, etc. Additives are typically formulated so that they can be readily incorporated into culture media. For example, culture media additives can be provided in powdered form, as a tablet or as a capsule readily dissolvable in aqueous culture media. In another examples, additives can be provided as concentrated solutions or as suspensions to be added to culture media.

The term "Chroman 1" refers to (3S)—N-{2-[2-(Dimethylamino)ethoxy]-4-(1H-pyrazol-4-yl)phenyl}-6-methoxy-3, 4-dihydro-2H-1-benzopyran-3-carboxamide, with the structure shown in FIG. 1. Chroman-related compounds or derivatives are structurally-related compounds (Chroman moiety-containing ROCK inhibitors), some of which are described in Chen et al. "Chroman-3-amides as potent Rho kinase inhibitors" *Bioorganic and Medicinal Chemistry Letters* 18:6406-6409 (2008) and LoGrasso et al. "Rho Kinase (ROCK) Inhibitors and Their Application to Inflammatory Disorders" *Current Topics in Medicinal Chemistry* 9:704-723 (2009). Chroman 1, its derivatives or related compounds can be supplied as a salt or in solution. An effective concentration of Chroman 1 (or its active derivative or a related compound) can be about 4 nM to about 80 µM, about 10 nM to about 20 µM, about 20 nM to about 10 µM or about 30 nM to about 500 nM, such as about 4 nM, 5 nM, 30 nM, 55 nM, 80 nM, 105 nM, 130 nM, 155 nM, 180 nM, 205 nM, 230 nM, 255 nM, 280 nM, 305 nM, 330 nM, 355 nM, 380 nM, 405 nM, 430 nM, 455 nM, 480 nM, 500 nM. 525 nM, 550 nM, 575 nM, 600 nM, 625 nM, 650 nM, 675 nM, 700 nM, 725 nM, 750 nM, 775 nM, 800 nM, 825 nM, 850 nM, 875 nM, 900 nM, 925 nM, 950 nM, 975 nM, 1 µM, 2 µM, 3 µM, 4 µM, 5 µM, 6 µM, 7 µM, 8 µM, 9 µM, 10 µM, 11 µM, 12 µM, 13 µM, 14 µM, 15 µM, 16 µM, 17 µM, 18 µM, 19 µM, 20 µM, 21 µM, 22 µM, 23 µM, 24 µM, 25 µM, 26 µM, 27 µM, 28 µM, 29 µM, 30 µM, 31 µM, 32 µM, 33 µM, 34 µM, 35 µM, 36 µM, 37 µM, 38 µM, 39 µM, 40 µM, 45 µM, 45 µM, 50 µM, 55 µM, 60 µM, 65 µM, 70 µM, 75 µM or 80 µM.

The term "Emricasan" refers to 3-(2-(2-tert-butylphenylaminooxalyl) aminopropionylamino)-4-oxo-5-(2,3,5,6-tetrafluorophenoxy)pentanoic acid, with the structure shown in FIG. 1. Emricasan-related compounds or derivatives are structurally-related compounds (such as Q-VD-OPh hydrate), some of which are described in Linton et al. "First-in-Class Pan Caspase Inhibitor Developed for the Treatment of Liver Disease" *J. Med. Chem.* 48:6779-6782, (2005). Emricasan, its derivatives or related compounds can be supplied as a salt or in solution. An effective concentration of Emricasan (or its active derivative or a related compound) can be about 5 nM to about 100 µM, about 5 nM to about 80 µM, about 200 nM to about 30 µM, about 300 nM to about 20 µM, for example, about 100 nM, 150 nM, 200 nM, 250 nM, 300 nM, 350 nM, 400 nM, 450 nM, 500 nM, 550 nM, 600 nM, 650 nM, 700 nM, 750 nM, 800 nM, 850 nM, 1 µM, 1.5 µM, 2 µM, 2.5 µM, 3 µM, 3.5 µM, 4 µM, 4.5 µM, 5 µM, 5.5 µM, 6 µM, 6.5 µM, 7 µM, 7.5 µM, 8 µM, 8.5 µM, 9 µM, 9.5 µM, 10 µM, 10.5 µM, 11 µM, 11.5 µM, 12 µM, 12.5 µM, 13 µM, 13.5 µM, 14 µM, 14.5 µM, 15 µM, 15.5 µM, 16 µM, 16.5 µM, 17 µM, 17.5 µM, 18 µM, 18.5 µM, 19 µM, 19.5 µM, 20 µM, 21 µM, 22 µM, 23 µM, 24 µM, 25 µM, 26 µM, 27 µM, 28 µM, 29 µM, 30 µM, 31 µM, 32 µM, 33 µM, 34 µM, 35 µM, 36 µM, 37 µM, 38 µM, 39 µM, 40 µM, 45 µM, 45 µM, 50 µM, 55 µM, 60 µM, 65 µM, 70 µM, 75 µM, 80 µM, 85 µM, 90 µM, 95 µM or 100 µM.

Figure 2:
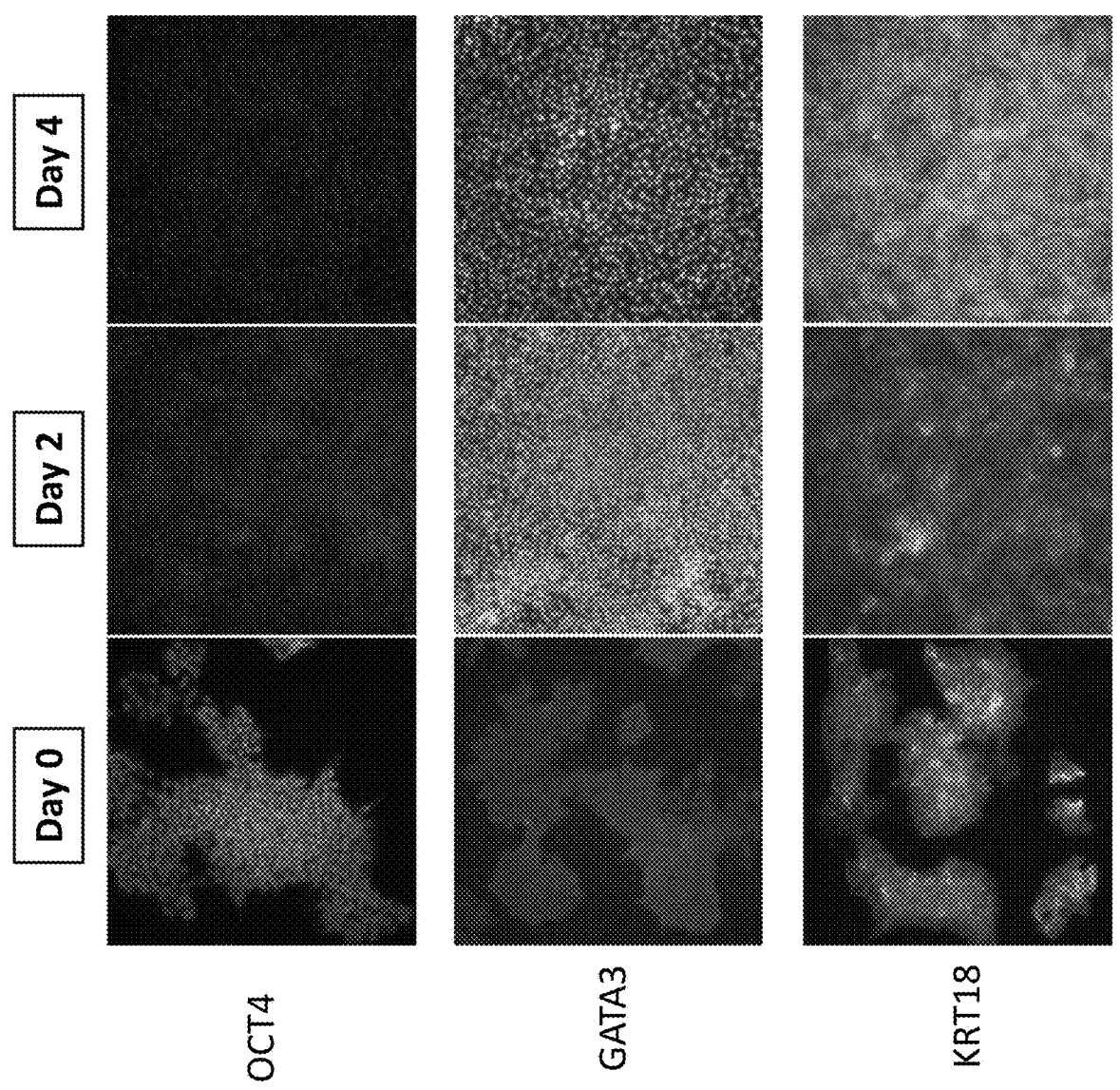
FIG. 2 shows representative microscopic images of the cells from different time points (indicated by the labels at the top of the images) of an embodiment of a method described in the present disclosure. The images of the cells that were immunocytochemically stained with the antibodies specific for OCT4, GATA3, or KRT18 proteins (indicated by the labels to the left of the images).

The term "trans-ISRIB," which can be used interchangeably with the terms "ISRIB" or "ISRIB (trans-isomer)" refers to N,N'-((1r,4r)-cyclohexane-1,4-diyl)bis(2-(4-chlorophenoxy)acetamide) with the structure shown in FIG. 2. As described in Sidrauski et al. "Pharmacological brake-release of mRNA translation enhances cognitive memory" *eLIFE* 2:e00498 (2013), trans-ISRIB is 100-fold more potent ($IC_{50}$=5 nM) than cis-ISRIB ($IC_{50}$=600 nM) suggesting a stereospecific interaction with the cellular target. Trans-ISRIB can be supplied as a salt or in solution. An effective concentration of trans-ISRIB can be about 5 nM to about 80 μM, about 5 nM to about 50 μM, about 100 nM to about 6.25 μM, or about 200 nM to about 6.25 μM, for example, about 50 nM, 100 nM, 150 nM, 200 nM, 250 nM, 300 nM, 350 nM, 400 nM, 450 nM, 500 nM, 550 nM, 600 nM, 650 nM, 700 nM, 750 nM, 800 nM, 850 nM, 1 μM, 1.25 μM, 1.5 μM, 1.75 μM, 2 μM, 2.25 μM, 2.5 μM, 2.75 μM, 3 μM, 3.25 μM, 3.5 μM, 3.75 μM, 4 μM, 4.25 μM, 4.5 μM, 4.75 μM, 5 μM, 5.25 μM, 5.5 μM, 5.75 μM, 6 μM, 6.25 μM, 6.5 μM, 7 μM, 7.5 μM, 8 μM, 8.5 μM, 9 μM, 9.5 μM, 10 μM, 10.5 μM, 11 μM, 11.5 μM, 12 μM, 12.5 μM, 13 μM, 13.5 μM, 14 μM, 14.5 μM, 15 μM, 15.5 μM, 16 μM, 16.5 μM, 17 μM, 17.5 μM, 18 μM, 18.5 μM, 19 μM, 19.5 μM, 20 μM, 21 μM, 22 μM, 23 μM, 24 μM, 25 μM, 26 μM, 27 μM, 28 μM, 29 μM, 30 μM, 31 μM, 32 μM, 33 μM, 34 μM, 35 μM, 36 μM, 37 μM, 38 μM, 39 μM, 40 μM, 45 μM, 45 μM, 50 μM, 55 μM, 60 μM, 65 μM, 70 μM, 75 μM or 80 μM.

The term "polyamines," as used herein, refers to one or more of the polycations putrescine, spermidine and spermine, which are known to interact with negatively charged macromolecules, such as DNA, RNA and proteins. An effective concentration of spermine can be about 0.5 nM to 1 mM, for example, about 0.5 nM, 20.5 nM, 40.5 nM, 60.5 nM, 80.5 nM, 100.5 nM, 120.5 nM, 140.5 nM, 160.5 nM, 180.5 nM, 200.5 nM, 220.5 nM, 240.5 nM, 260.5 nM, 280.5 nM, 300.5 nM, 320.5 nM, 340.5 nM, 360.5 nM, 380.5 nM, 400.5 nM, 420.5 nM, 440.5 nM, 460.5 nM, 480.5 nM, 0.5 μM, 20.5 μM, 40.5 μM, 60.5 μM, 80.5 μM, 100.5 μM, 120.5 μM, 140.5 μM, 160.5 μM, 180.5 μM, 200.5 μM, 220.5 μM, 240.5 μM, 260.5 μM, 280.5 μM, 300.5 μM, 320.5 μM, 340.5 μM, 360.5 μM, 380.5 μM, 400.5 μM, 420.5 μM, 440.5 μM, 460.5 μM, 480.5 μM, 500.5 μM, 520.5 μM, 540.5 μM, 560.5 μM, 580.5 μM, 600.5 μM, 620.5 μM, 640.5 μM, 660.5 μM, 680.5 μM, 700.5 μM, 720.5 μM, 740.5 μM, 760.5 μM, 780.5 μM, 800.5 μM, 820.5 μM, 840.5 μM, 860.5 μM, 880.5 μM, 900.5 μM, 920.5 μM, 940.5 μM, 960.5 μM, 980.5 μM or 1 mM. An effective concentration of spermidine can be about 0.5 μM to 1 mM, for example, approximately 0.5 nM, 20.5 nM, 40.5 nM, 60.5 nM, 80.5 nM, 100.5 nM, 120.5 nM, 140.5 nM, 160.5 nM, 180.5 nM, 200.5 nM, 220.5 nM, 240.5 nM, 260.5 nM, 280.5 nM, 300.5 nM, 320.5 nM, 340.5 nM, 360.5 nM, 380.5 nM, 400.5 nM, 420.5 nM, 440.5 nM, 460.5 nM, 480.5 nM, 0.5 μM, 20.5 μM, 40.5 μM, 60.5 μM, 80.5 μM, 100.5 μM, 120.5 μM, 140.5 μM, 160.5 μM, 180.5 μM, 200.5 μM, 220.5 μM, 240.5 μM, 260.5 μM, 280.5 μM, 300.5 μM, 320.5 μM, 340.5 μM, 360.5 μM, 380.5 μM, 400.5 μM, 420.5 μM, 440.5 μM, 460.5 μM, 480.5 μM, 500.5 μM, 520.5 μM, 540.5 μM, 560.5 μM, 580.5 μM, 600.5 μM, 620.5 μM, 640.5 μM, 660.5 μM, 680.5 μM, 700.5 μM, 720.5 μM, 740.5 μM, 760.5 μM, 780.5 μM, 800.5 μM, 820.5 μM, 840.5 μM, 860.5 μM, 880.5 μM, 900.5 μM, 920.5 μM, 940.5 μM, 960.5 μM, 980.5 μM or 1 mM. An effective concentration of putrescine can be about 0.5 μM to 1 mM, for example, approximately 0.5 nM, 20.5 nM, 40.5 nM, 60.5 nM, 80.5 nM, 100.5 nM, 120.5 nM, 140.5 nM, 160.5 nM, 180.5 nM, 200.5 nM, 220.5 nM, 240.5 nM, 260.5 nM, 280.5 nM, 300.5 nM, 320.5 nM, 340.5 nM, 360.5 nM, 380.5 nM, 400.5 nM, 420.5 nM, 440.5 nM, 460.5 nM, 480.5 nM, 0.5 μM, 20.5 μM, 40.5 μM, 60.5 μM, 80.5 μM, 100.5 μM, 120.5 μM, 140.5 μM, 160.5 μM, 180.5 μM, 200.5 μM, 220.5 μM, 240.5 μM, 260.5 μM, 280.5 μM, 300.5 μM, 320.5 μM, 340.5 μM, 360.5 μM, 380.5 μM, 400.5 μM, 420.5 μM, 440.5 μM, 460.5 μM, 480.5 μM, 500.5 μM, 520.5 μM, 540.5 μM, 560.5 μM, 580.5 μM, 600.5 μM, 620.5 μM, 640.5 μM, 660.5 μM, 680.5 μM, 700.5 μM, 720.5 μM, 740.5 μM, 760.5 μM, 780.5 μM, 800.5 μM, 820.5 μM, 840.5 μM, 860.5 μM, 880.5 μM, 900.5 μM, 920.5 μM, 940.5 μM, 960.5 μM, 980.5 μM or 1 mM.

The terms "CEPT," "CEPT cocktail" or "CEPT small molecule cocktail" refer to a combination of effective amounts or concentrations of Chroman 1 or a derivative thereof, Emricasan or a derivative thereof, trans-ISRIB and polyamines.

The term "Y27632" refers to trans-4-[(1R)-1-Amino-ethyl]-N-4-pyridinylcyclohexanecarboxamide dihydrochloride. An effective concentration of Y27632 can be 100 nM-100 μM.

The term "blebbistatin" refers to (±)-1,2,3,3a-Tetrahydro-3a-hydroxy-6-methyl-1-phenyl-4H-pyrrolo[2,3-b]quinolin-4-one. An effective concentration of blebbistatin can be 10 nM-100 μM.

The term "thiazovivin" refers to N-Benzyl-[2-(pyrimidin-4-yl)amino]thiazole-4-carboxamide. An effective concentration of thiazovivin can be 5 nM-100 μM.

The term "A83-01" refers to 3-(6-Methyl-2-pyridinyl)-N-phenyl-4-(4-quinolinyl)-1H-pyrazole-1-carbothioamide. An effective concentration of A83-01 can be 10 nM to 100 μM.

The term "SB 431542" refers to 4-[4-(1,3-benzodioxol-5-yl)-5-(2-pyridinyl)-1H-imidazol-2-yl]benzamide. An effective concentration of SB 431542 can be 10 nM to 100 μM.

The term "CHIR99021" refers to 6-[[2-[[4-(2,4-Dichlorophenyl)-5-(5-methyl-1H-imidazol-2-yl)-2-pyrimidinyl] amino]ethyl]amino]-3-pyridinecarbonitrile. An effective concentration of CHIR99021 can be 10 nM to 100 μM.

The term "CH5183284" refers to (5-amino-1-(2-methyl-3H-benzo[d]imidazol-5-yl)-1H-pyrazol-4-yl)(1H-indol-2-yl)methanone. An effective concentration of CH5183284 can be 10 nM to 50 μM.

The term "PD-166866" refers to 1-[2-amino-6-(3,5-dimethoxyphenyl)-pyrido[2,3-d]pyrimidin-7-yl]-3-tert-butyl urea. An effective concentration of PD-166866 can be 10 nM to 100 μM.

The term "CHIR98014" refers to N2-(2-(4-(2,4-dichlorophenyl)-5-(1H-imidazol yl)pyrimidin-2-ylamino)ethyl)-5-nitropyridine-2,6-diamine. An effective concentration of CHIR98014 can be 10 nM to 100 μM.

Bone Morphogenetic Protein 4 (BMP4) is a protein that can be recombinantly produced. Recombinantly produced BMP4 is available, for example, from R&D Systems. An effective concentration of BMP4 can be 5 to 200 ng/ml.

Bone Morphogenetic Protein 10 (BMP 10), is a protein that can be recombinantly produced. Recombinantly produced BMP10 is available, for example, from R&D Systems. An effective concentration of BMP10 can be 5 to 200 ng/ml.

Epidermal Growth Factor (EGF) is a protein that can be recombinantly produced. Recombinantly produced EGF is available, for example, from R&D Systems. An effective concentration of EGF can be 5 to 500 ng/ml.

Hepatocyte Growth Factor (HGF) is a protein that can be recombinantly produced. Recombinantly produced HGF is available, for example, from R&D Systems. An effective concentration of HGF can be 5 to 500 ng/ml.

Roof Plate-Specific Spondin 1 (R-spondin 1) is a protein that can be recombinantly produced. Recombinantly produced R-spondin 1 is available, for example, from R&D Systems. An effective concentration of R-spondin 1 can be 50 to 500 ng/ml.

Roof Plate-Specific Spondin 3 (R-spondin 3) is a protein that can be recombinantly produced. Recombinantly produced R-spondin 3 is available, for example, from R&D Systems. An effective concentration of R-spondin 3 can be 5 to 500 ng/ml.

Prostaglandin $E_2$ is a lipid compound, which can be also referred to as (5Z,11α,13E,15S)-11,15-Dihydroxy-9-oxo-prosta-5,13-dien-loic acid. Prostaglandin $E_2$ is widely available as a pharmaceutical compound or a reagent. An effective concentration of prostaglandin $E_2$ can be 5 nM to 100 μM.

Cells, Compositions and Kits

Some embodiments of the methods of cell production described in this disclosure involve, as a starting material or an intermediate, pluripotent or precursor cells or population of pluripotent or precursor cells or that are capable of selectively (and sometimes reversibly) developing into specified cellular lineages when cultured under appropriate conditions. One example of a precursor cell population that can be involved in the methods of cell production described in this disclosure is a culture of pluripotent stem cells (PSCs), which may be a culture embryonic stem cells (ESCs) and induced pluripotent stem cells (iPSCs). Some embodiments of the methods of cell production described in this disclosure involve human PSCs (hPSCs) or their populations as a starting material for deriving cytotrophoblast-like cells, syncytiotrophoblast-like structures, or trophoblast stem cell-like cells. It is to be understood that embodiments of the methods of cell production described in this disclosure can involve modified PSCs, including hPSCs. Some examples of PSCs that can be used in the methods according to the embodiments of the present invention are various ESCs (WA07, WA09, WA14, WA17, JHU191i, JHU198i, or MCW032i, all available from WiCell) and iPSC lines (LiPSC-GR1.1, NCRM-1, NCRM-2, NCRM-5, all available from National Institutes of Health (USA)).

As discussed throughout the present disclosure, some embodiments of the methods of the present invention produce various cells, cell populations, or cell cultures, which are produced ex vivo (in culture) and exhibit at least some characteristics of naturally occurring cells or populations of cells of trophectodermal lineage, such as detectable presence or absence of certain markers, and/or other properties. It is also to be understood that a cell population may include a variety of cells on a continuum, with varying levels of presence or absence of certain detectable markers. Cells, cell populations and cell cultures produced by the embodiments of the methods of the present invention described in the present disclosure are included among the embodiments of the present invention. For example, cytotrophoblast-like cells, their populations and cultures are included among the embodiments of the present invention. Cytotrophoblast-like cells are cells that exhibit at least some characteristics of naturally occurring cytotrophoblasts, such as the ability to store glycogen in cytoplasm, and/or expression of one or more of cytotrophoblast-associated markers, for example, CDX2, GATA3, KRT7, KRT18, TFAP2A, or IGFBP3. In another example, syncytiotrophoblast-like structures, as well as cell populations and cultures including syncytiotrophoblast-like structures are included among the embodiments of the present invention. Syncytiotrophoblast-like structures produced by the methods according to the embodiments of the present invention exhibit at least some characteristics of naturally occurring syncytiotrophoblasts, such as being multinucleated structures, and/or expressing of one or more of syncytiotrophoblast-associated markers, such as DLX3, CGA; GATA3, KRT7, DAB2, TEAD3, or TFAP2C. In one more example, trophoblast stem cell-like cells, as well as cell populations and cultures including trophoblast stem cell-like cells are included among the embodiments of the present invention. Trophoblast stem cell-like cells produced by the methods according to the embodiments of the present invention exhibit at least some characteristics of naturally occurring trophoblast stem cells, such as a capacity for self-renewal, expression of the proliferation marker Ki-67 (also known as MKI67 protein), and/or expression of one or more of trophoblast-associated markers, such as ELF5, GATA3, CDX2, TFAP2C, KRT7, and YAP1.

Compositions according to the embodiments of the present invention include in vitro or ex vivo compositions comprising at least one cell according to embodiments for the present invention. For example, compositions including at least one cytotrophoblast-like cell, at least one syncytiotrophoblast-like structure, or at least one trophoblast stem cell-like cell are included among the embodiments of the present invention. The cells included in such compositions can be mammalian cells (meaning the cells generated from mammalian PSCs), including human cells (meaning the cells generated from human PSCs). The cells included in such compositions can be modified cells. The compositions can include pluralities of cells of the same or different type. For example, a plurality of cells can include one or more of a pluripotent stem cell, a multipotent stem cell, a progenitor cell, a differentiated cell, and a modified cell. A plurality of mammalian cells can be multiple cells, a cell culture, a cell aggregate, a spheroid or a tissue. At least one cell or a plurality of cells can be cryopreserved or thawed after cryopreservation. It is understood that some of the compositions according to embodiments of the present invention can further comprise a culture medium, one or more additives, a vessel containing the culture medium, such as a culture flask, a culture dish, a tube or a reactor, and can also comprise a support or a scaffold for cells.

Using the described methods, compositions comprising various mixtures of PSCs and other multipotent or differentiated cells can be produced. Such compositions are included among the embodiments of the present invention. In some embodiments, compositions comprising at least about 5 multipotent or differentiated cells for about every 95 pluripotent cells can be produced. In other embodiments, compositions comprising at least about 95 multipotent or differentiated cells for about every 5 pluripotent cells can be produced. Additionally, compositions comprising other ratios of multipotent or differentiated cells to pluripotent cells are contemplated. For example, compositions comprising at least about 1 multipotent or differentiated cell for about every 1,000,000 pluripotent cells, at least about 1 multipotent or differentiated cell for about every 100,000 pluripotent cells, at least about 1 multipotent or differentiated cell for about every 10,000 pluripotent cells, at least about 1 multipotent or differentiated cell for about every 1000 pluripotent cells, at least about 1 multipotent or differentiated cell for about every 500 pluripotent cells, at least about 1 multipotent or differentiated cell for about every 100 pluripotent cells, at least about 1 multipotent or differentiated cell for about every 10 pluripotent cells, at least about 1 multipotent or differentiated cell for about every 5 pluripotent cells, and up to about every 1 pluripotent cell and at least about 1,000,000 multipotent or differentiated cell for about every 1 pluripotent cell are contemplated. Some embodiments of the compositions can be cell cultures or cell populations comprising from at least about 5% multipotent or differentiated cell to at least about 99% multipotent or differentiated cells. In some embodiments the cell cultures or cell populations comprise mammalian cells. In some embodiments, the cell cultures or cell populations comprise human cells. For example, certain specific embodiments relate to cell cultures comprising human cells, wherein from at least about 5% to at least about 99% of the human cells are multipotent or differentiated cell. Other embodiments relate to cell cultures comprising human cells, wherein at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or greater than 99% of the human cells are multipotent or differentiated cells.

Kits for cell, tissue or organ culture are included among embodiments of the present invention. A kit is a set of components, comprising at least some components for culturing cells, which can include single cells and groups of cells. A kit can contain one or more additives discussed in the corresponding section of this disclosure. A kit may further contain one or more of the following: culture media configured to support at least one cell in vitro or ex vivo or one or more of culture media components; a vessel for holding the culture medium; a culture vessel, such as a flask, a dish, a plate (including a multi-well plate) or a reactor; or a support or scaffold for cell or tissue culture. A kit may contain one or more mammalian cells, such as human cells. Cells included in the kit can be one or more of: mammalian PSCs (including embryonic stem cells and/or induced pluripotent stem cells), cytotrophoblast-like cells, syncytiotrophoblast-like structures, or trophoblast stem cell-like cells. One or more cells can be provided in a frozen or non-frozen form (which can be a thawed form).

Cryopreservation

Methods, compositions and kits that involve cryopreservation, including processes, tools and/or compositions related to cryopreservation, thawing and culturing of previously cryopreserved cells, cell populations or cell cultures are included among the embodiments of the present invention. Some compositions related to the preservation can include a cryopreservation medium used for the cryopreservation of cells or cell populations described in this disclosure, such as cytotrophoblast-like cells, syncytiotrophoblast-like structures, or trophoblast stem cell-like cells. Some compositions can include a cryopreservation medium and one or more cells described in this disclosure. For example, an embodiment of a composition can include one or more cytotrophoblast-like cells and a cryopreservation medium. In another example, a composition can include one or more syncytiotrophoblast-like structures and a cryopreservation medium. In one more example, a composition can include one or more trophoblast stem cell-like cells and a cryopreservation medium. The cryopreservation medium can be a liquid medium in which the cells are found prior to freezing and/or while in frozen state. Some examples of cryopreservation media are PSC Cryopreservation Kit (Thermo Fisher Scientific), FreezIS (Irving Scientific), NutriFreez (Biological Industries USA), CryoStor, Hypo-Thermosol, mFreSR, mFreSR-S, STEMdiff Neural Progenitor Freezing Medium (all from Stem Cell Technologies). Cryopreservation medium can contain one or more cryoprotectants, meaning compounds protecting cells from freezing damage. Cryoprotectants can be permeating or non-permeating. An example of a suitable permeating cryoprotectant, which is able to permeate cell membranes, is dimethyl sulfoxide (DMSO). Some examples of suitable non-permeating cryoprotectants are sucrose, glycerol, dextran, trehalose, percoll, polyethylene glycol, polyvinyl pyrrolidone, serum albumin, ficol, maltose and polyvinylalcohol (PVA). The cryopreservation medium can further contain one or more additives described in the section "Additives" of this disclosure. For example, the cryopreservation medium can comprise one or more of Chroman-1 or its derivatives, Emricasan or its derivatives, trans-ISRIB or polyamines, at their respective effective combination. A combination of all four of the above additives can be referred to as "CEPT."

Methods involving cryopreservation of cells, cell populations or cell cultures are included among the embodiments of the present invention. Such methods may include a step of contacting one or more cells, such as cytotrophoblast-like cells, syncytiotrophoblast-like structures, or trophoblast stem cell-like cells with a cryopreservation medium. This may involve adding the cryopreservation medium to the one or more cells, or vice versa, and mixing the cells with the medium. In some embodiments, between 0.5 mL and 5 mL of cryopreservation medium may be added per one million cells, for example about 1 mL per million cells. However, it is envisaged that in certain embodiments, higher or lower amounts of cryopreservation medium can be used. In some embodiments, the cryopreservation medium may be added to the cells in stepwise increments of increasing concentration, which may reduce the risk of cellular osmotic shock associated with single-step addition. The temperature of the cryopreservation medium when added to the cells may range from about 15° C. to about 40° C. For example, the temperature of the cryopreservation medium added to the cells can be about 37° C. The contacting step of the present method may result in suspension of the cells in the cryopreservation medium, which can be referred to as "mixture." The cells before the contacting step or the cell suspension after the contacting step may be provided in a container or a vessel. A container may have a volume between 1 mL and 50 mL, for example, it may be a tube of 15 mL.

Methods involving cryopreservation of cells may include a step of freezing a composition comprising one or more cells, such as cytotrophoblast-like cells, syncytiotrophoblast-like structures, or trophoblast stem cell-like cells, and a cryopreservation medium, thereby obtaining a frozen or cryopreserved composition. A mixture of the cells and the cryopreservation medium can be equilibrated prior to freezing the mixture. During equilibration, water can be removed from the cells and replaced by the medium comprising the cryoprotectant, which enters into the cells after incubation of the cells with the cryopreservation medium. The equilibration time is limited to avoid damage to the cells. For example, the mixture can be equilibrated for a time period of between 10 seconds and 5 minutes, between 20 seconds and 1.5 minutes, or between 30 seconds to 1 minute. Before freezing, the mixture can be transferred to a freezing container or vessel, or remain in the same container in which the mixture already resided. Water can be removed from the cells and replaced by the medium comprising the cryoprotectant, which enters into the cells after incubation of the cells with the cryopreservation medium. The containers used for freezing typically provide for the stacking of tubes and can ensure that, by placing the container in a freezer, a fixed rate of cooling is achieved.

The freezing results in the cells in a cryogenic or cryopreserved state (which may simply be described as "frozen"), in which they can remain for periods of days, weeks, months or years, for retrieval when the cells are required. When needed, the cryopreserved cells are retrieved and thawed. Accordingly, methods involving cryopreservation can include a step of thawing a cryopreserved composition, more particularly under conditions that maintain cell viability. For example, a container containing the cryopreserved cells can be thawed in a bath of water, at a temperature of 42° C. or less, such as between 10° C. and 40° C., for example, at about 37° C. To improve the post-thaw cell viability, a thawing rate between about 10° C. and about 40° C. per minute, such as about 20° C. and about 40° C. per minute, for example, approximately 30° C. per minute may be used.

The described methods and/or method steps may lead to good viability of cryopreserved cells after thawing. As used herein, the term "viability" refers to the number of living cells based on the presence of DNA and an intact cell membrane system. Viability can be measured by various tests, such as a Trypan blue internalization test or by measuring propidium iodide uptake. The viability of the thawed cells after cryopreservation, such as thawed cytotrophoblast-like cells, syncytiotrophoblast-like structures, or trophoblast stem cell-like cells can be at least 50%, at least 55%, at least 60%, at least 65%, at least 70%, at least 75%, at least 80%, at least 85%, at least 90%, or at least 95%. The cells may display a limited amount of necrosis and apoptosis after thawing. In particular embodiments, necrosis and/or apoptosis is observed in less than 25% of the cells, more particularly less than 15%, most particularly less than 10% of the cells. The methods described herein may further ensure that cytotrophoblast-like cells, syncytiotrophoblast-like structures, or trophoblast stem cell-like cells maintain their ability to differentiate. After thawing, the cryopreserved cells may be used for further culturing, differentiation, therapeutic purposes, such as regenerative medicine, or other uses.

The following examples will serve to further illustrate the present invention without, at the same time, however, constituting any limitation thereof. On the contrary, it is to be clearly understood that resort may be had to various embodiments, modifications and equivalents thereof which, after reading the description herein, may suggest themselves to those skilled in the art without departing from the spirit of the invention.

Example 1

Differentiation of Human Pluripotent Stem Cells into Trophectoderm Lineage-Like Cells Procedures for differentiation of human pluripotent stem cells into trophectoderm lineage-like cells are schematically illustrated in FIG. 1. Exemplary microscopic images of the cells generated at different time points in the differentiation procedure are also shown in FIG. 1. Human pluripotent stem cells (hPSCs) used in the procedure, including embryonic stem cells (ESCs) and induced pluripotent stem cells (iPSCs), were maintained and expanded in defined E8 medium. Human ESC and iPSC lines were purchased from WiCell (Madison, Wisconsin). hPSCs were grown as attached monolayer cultures.

At the start of the procedure ("Day −1," as illustrated in the timeline shown in FIG. 1), hPSCs cultured in chemically defined E8 medium on recombinant vitronectin-coated plates were dissociated into small clumps using ethylenediaminetetraacetic acid (EDTA) and seeded onto vitronectin-coated plates in E8 medium, in some instances supplemented with CEPT. The cells were seeded at densities ranging from approximately $30\times10^5$ to approximately $60\times10^5$ cells/cm² to achieve, about 24 hours later, the confluence of the hPSCs cultures of between 25% and 50%. When CEPT supplementation was used, a lower cell seeding density was needed to arrive within the acceptable range of starting confluence. To initiate cell differentiation at "Day 0" (as illustrated in the timeline shown in FIG. 1), CEPT-supplemented E8 medium was exchanged for TE1 medium (E6 medium supplemented with a TGF-beta inhibitor (A83-01), a Wnt signaling activator (CHIR99021), a FGF receptor inhibitor (CH5183284) and recombinant proteins BMP4 and BMP10). The cells were cultured for the for the next 3 days ("Days 1-3," as illustrated in the timeline shown in FIG. 1) in TE1 medium with daily medium changes. During the three days of culturing in TE1 medium, the cells exhibited downregulation of pluripotency-associated transcription factors, such as OCT4 (as illustrated in FIG. 2), and converted into a monolayer of cytotrophoblast-like cells upregulating specific genes, such as CDX2, GATA3, KRT7, and KRT18 (as partially illustrated in FIG. 2). The immunocytochemical analysis illustrated in FIG. 2 demonstrated pluripotency exit and induction of trophectoderm markers in the cells. As cytotrophoblast-like cells emerged in the culture, they began storing glycogen in their cytoplasm. The stored glycogen became visible as prominent dark material using phase-contrast microscopy, and was also visualized by periodic acid-Schiff (PAS) staining, as illustrated in FIG. 3. The cells were not passaged during the TE1 culturing phase. The cell monolayer became confluent as early as 48 to 72 hours after the start of TE1 culturing phase.

Figure 4A:
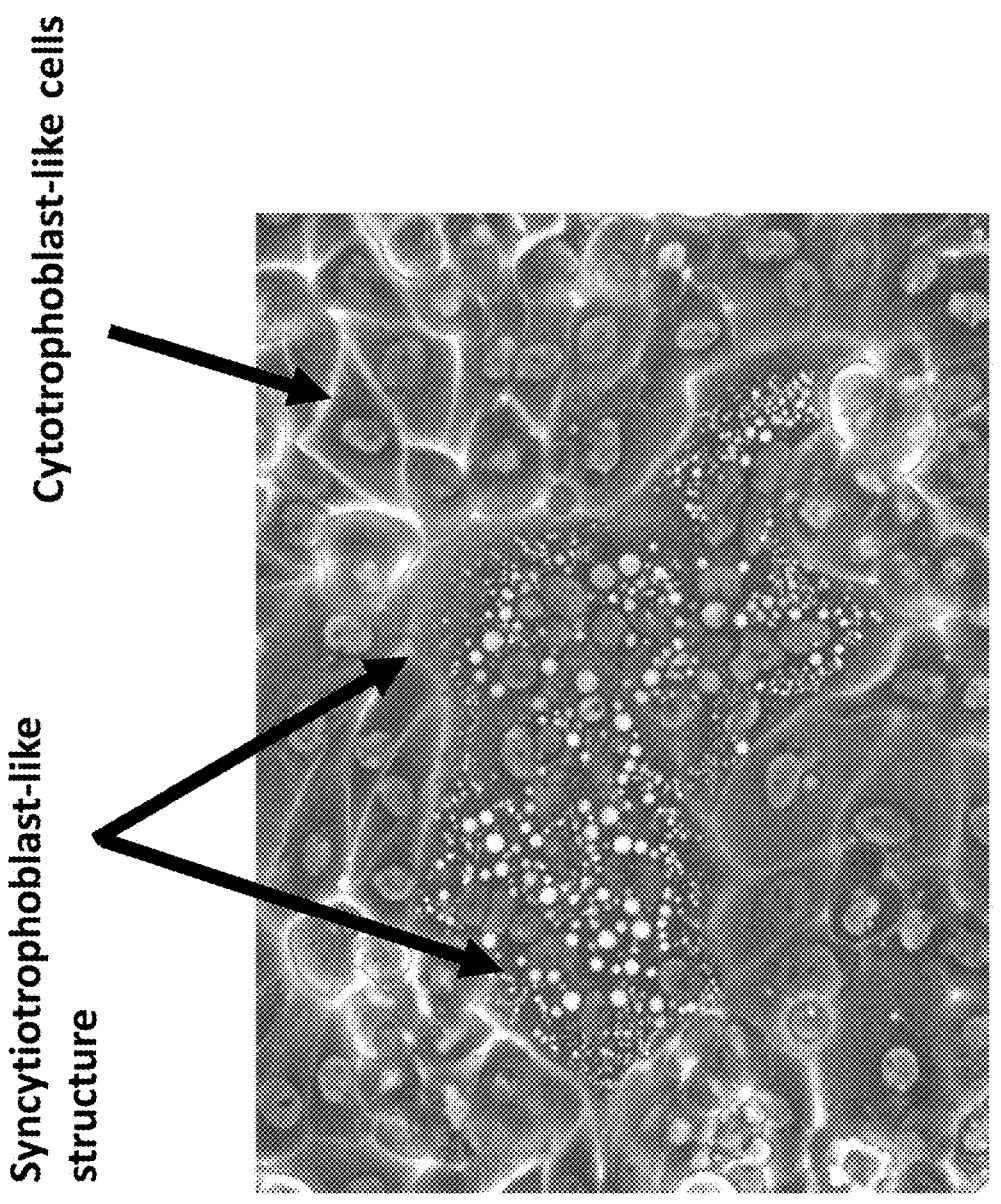
FIG. 4A shows representative phase-contrast microscopic images showing cytotrophoblast-like cells and syncytiotrophoblast-like structures.
Figure 4B:
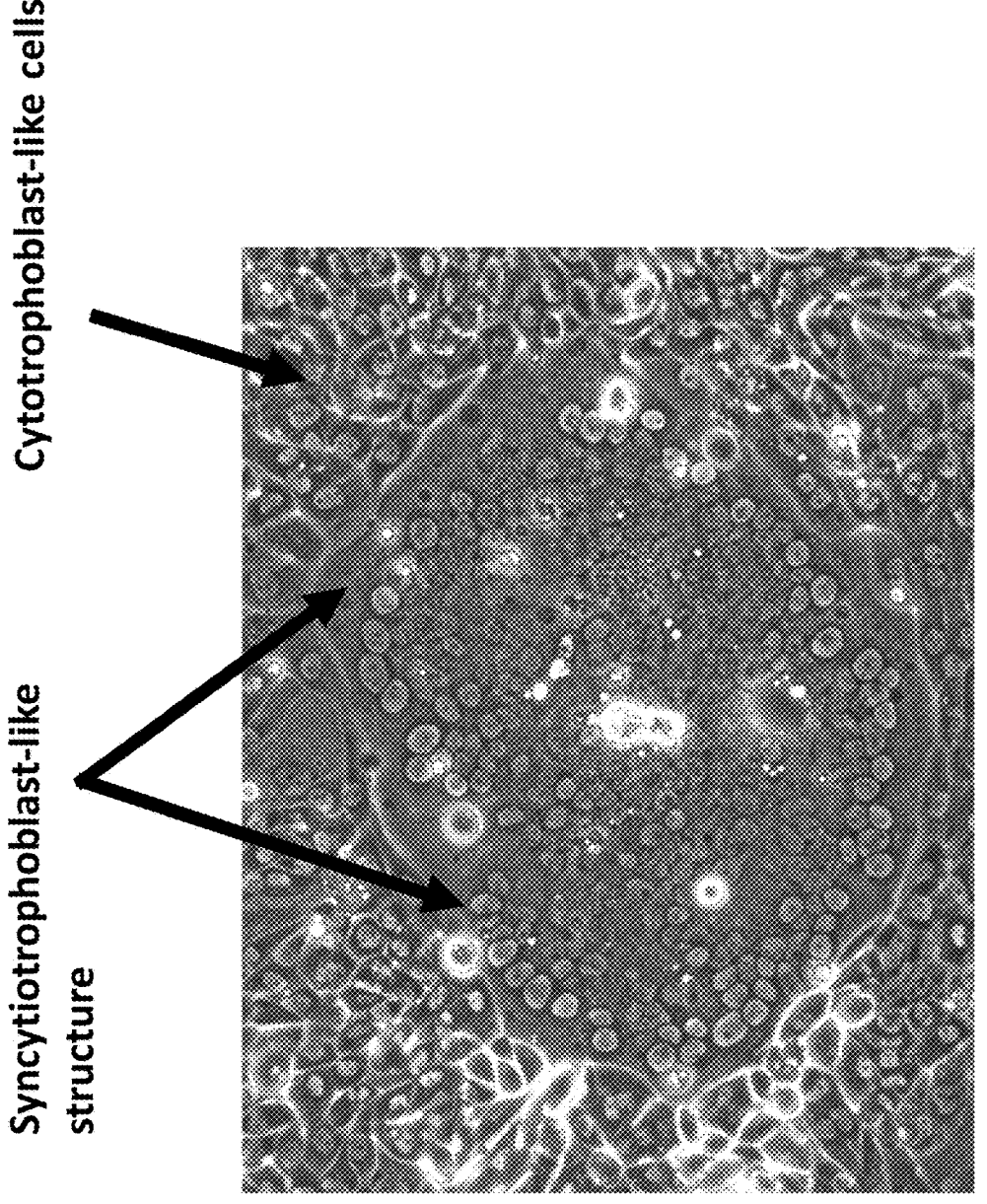
FIG. 4B shows representative phase-contrast microscopic images showing cytotrophoblast-like cells and syncytiotrophoblast-like structures.
Figure 6:
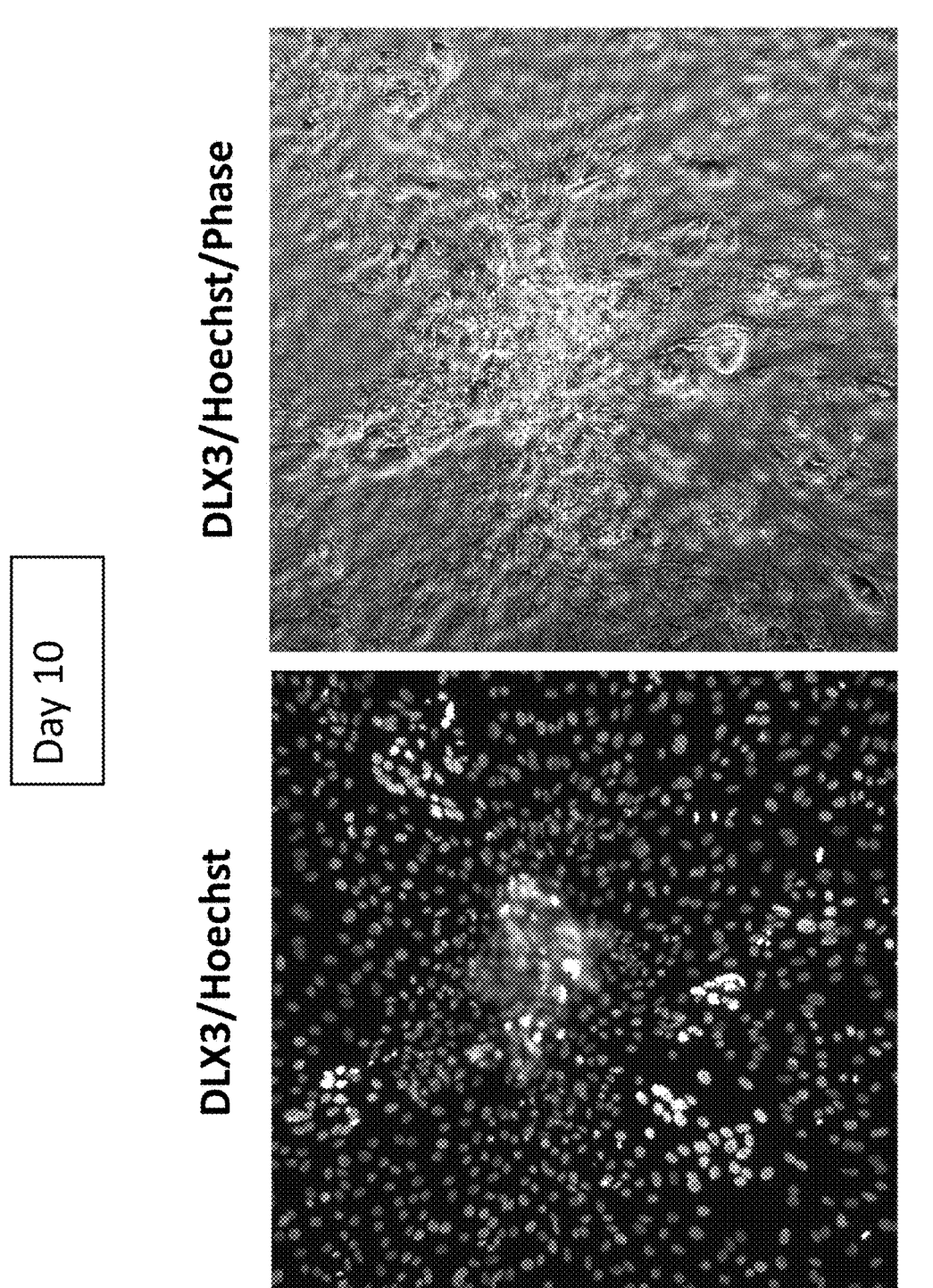
FIG. 6 shows representative microscopic images illustrating immunocytochemical analysis demonstrating expression of transcription factor DLX3 by syncytiotrophoblast-like structures, but not by the surrounding cytotrophoblast-like cells. Hoechst dye was used to stain the nuclei. In addition to DLX3/Hoechst staining shown in the image on the left, the image on the right contains the phase-contrast layer that visualizes the total morphology of the cells.

At the end of "Day 3" (as illustrated in the timeline shown in FIG. 1), the culture medium was switched to TE2 medium (E6 medium supplemented with a TGF-beta inhibitor (A83-01), a WNT signaling activator (CHIR99021)), and the cells were cultured in TE2 medium for the next 7 days ("Days 4-10," as illustrated in the timeline shown in FIG. 1), with daily medium changes. During culturing of the cells in TE2 medium, the cell monolayer remained confluent, and the cells were not passaged until the end of the TE2 culturing phase (usually from "Day 7" to "Day 13, for example, on "Day 10" based on the timeline shown in FIG. 1). During culturing of the cells in TE2 medium, further differentiation into cytotrophoblast-like cells and frequent cell fusion events where observed (as illustrated in FIGS. 4A and 4B), which generated large multinucleated syncytiotrophoblast-like structures around "Day 10" (as illustrated in the timeline shown in FIG. 1). The observed fused multinucleated structures expressed typical markers of syncytiotrophoblasts, such as DLX3, CGA, DAB2, TEAD3, and TFAP2A. Immunocytochemical analysis of the cells was performed at "Day 10," at which point about 5% of all the detectable nuclei were observed to be embedded in fused syncytiotrophoblast-like structures. The immunocytochemical analysis demonstrated, as illustrated in FIG. 5, that the cells expressed transcription factors GATA3, TFAP2A and CDX2, cytokeratin KRT7, tight junction protein ZO-1, and human chorionic gonadotropin (CGA). CGA was specifically expressed by fused syncytiotrophoblast-like structures. As illustrated in FIG. 5, the immunochemical analysis showed that mitogen-responsive phosphoprotein DAB2 was enriched in syncytiotrophoblast-like structures. As illustrated in FIG. 6, the immunochemical analysis also showed that syncytiotrophoblast-like structures, but not the surrounding cytotrophoblast-like cells, expressed transcription factor DLX3.

Figure 7A:
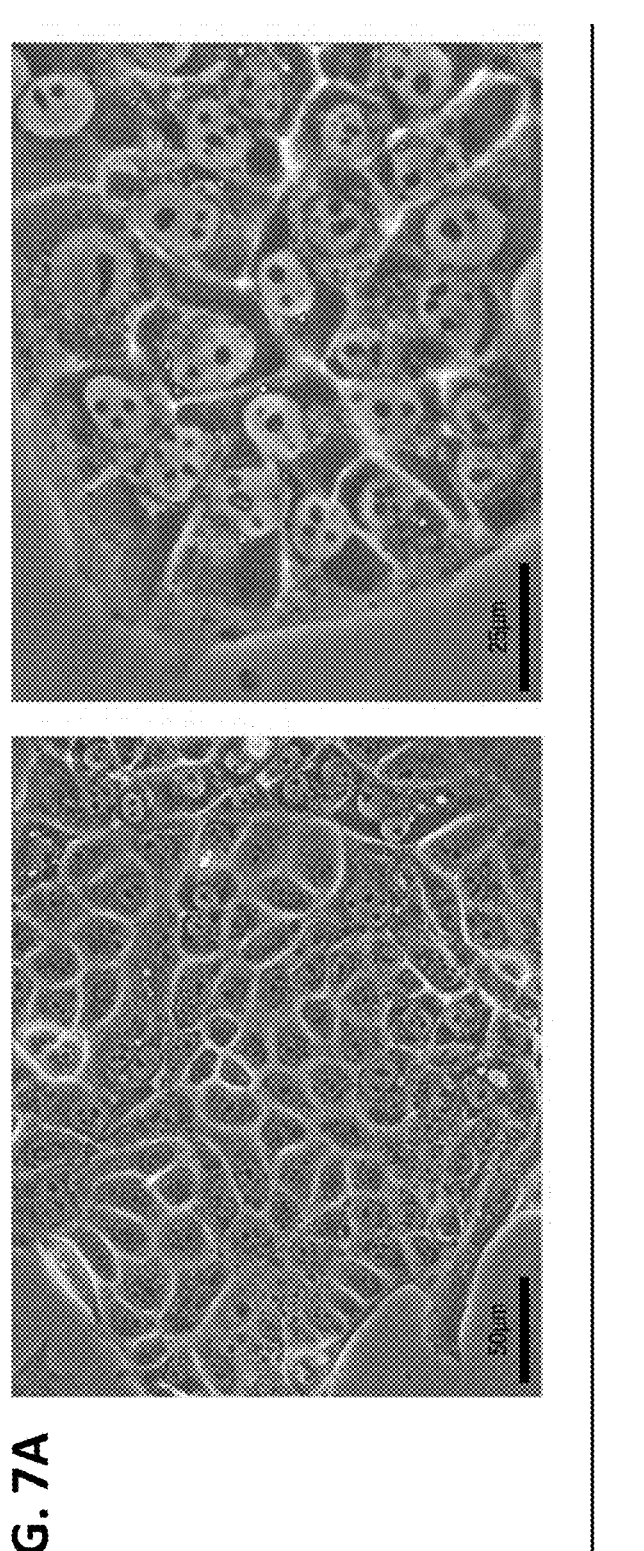
FIG. 7A shows representative microscopic images of WA09-derived trophoblast stem-like cells at passage 18 growing in densely packed colonies. The two images shown are at different magnification (illustrated by the scales in the bottom left corners of the images). The image on the right shows cellular morphology in more detail.
Figure 7B:
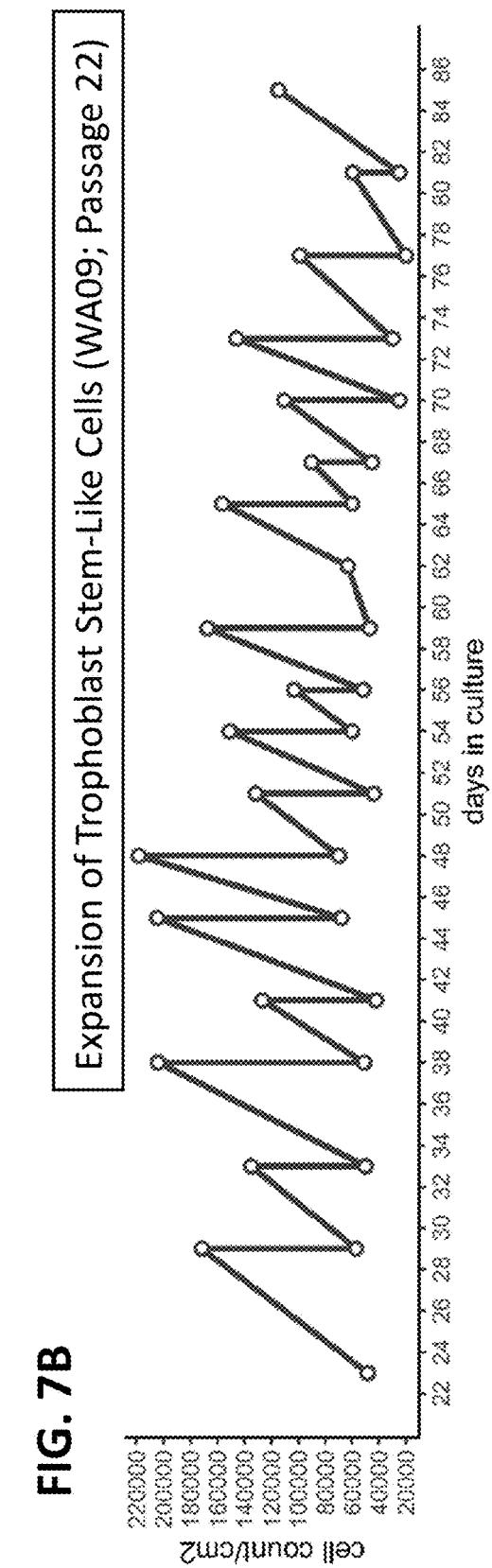
FIG. 7B shows a line plot monitoring the expansion of trophoblast stem-like cells produced from human embryonic stem cell line WA09 in TE3 medium (cell count with Trypan blue exclusion method) at every passage (with and without the use of the CEPT cocktail), which was performed every 3-6 days. Cell counts are plotted at the Y axis. Each peak of the line plot represents one passage: a point at which the cells reached high density and were therefore dissociated and seeded into a new culture vessel to prevent overcrowding and maintain cell health and proper phenotype in a monolayer of cells. 22 passages were performed after the cells reached the end of the initial induction phase in TE2 at around day 10. The number of days plotted on the Y-axis of the plot represents the number of days after the induction phase.

To generate self-renewing trophoblast stem-like cells from the syncytiotrophoblast-like structures, the syncytiotrophoblast-like structures were cultured in TE3 medium: TE2 medium supplemented with 300 nM CHIR98014, 100 ng/ml EGF, 50 ng/ml HGF, 80 ng/ml R-spondin 1, 50 ng/ml R-spondin 3, 2.5 $\mu$M prostaglandin $E_2$ and 25 nM Chroman 1. Trophoblast stem-like cells appeared in the cultures and started proliferating after a very short time following the start of the culturing into TE3 medium. The cells created compact epithelial-like colonies with cobblestone morphology and clearly defined border. The individual cells gradually became more compact. This morphological transformation was most obvious at passage 3 performed in TE3 medium. After the initial appearance, trophoblast stem-like cells were proliferated in TE3 medium for more than 20 passages, as illustrated in FIG. 7B, which illustrates the expansion of trophoblast-like cells produced from human embryonic stem cell line WA09 in TE3 medium.

Figures 8A, 8B, 8C, 8D:
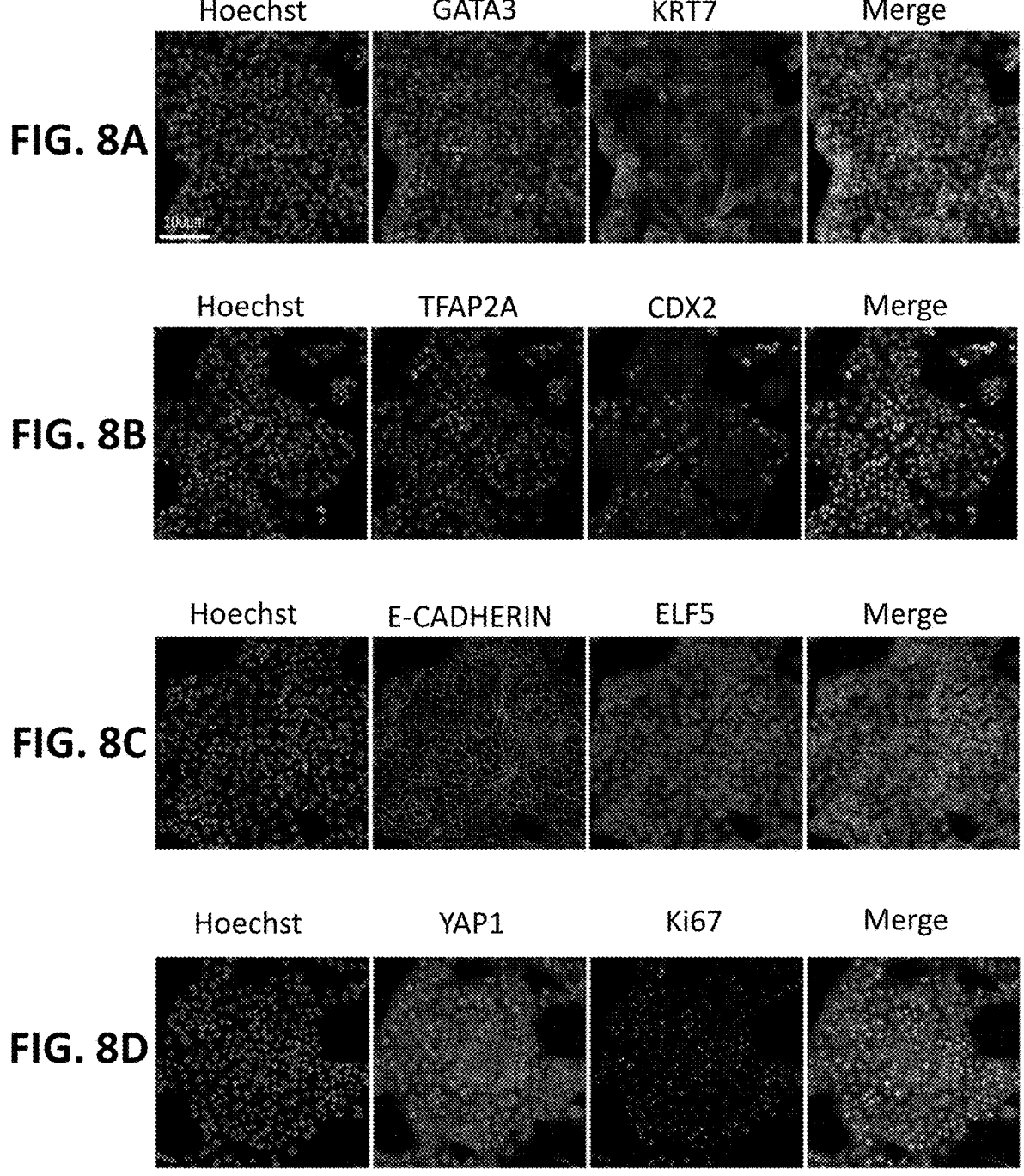
FIG. 8A shows representative microscopic images illustrating immunocytochemical analysis of trophoblast stem-like cells. Hoechst dye was used to stain nuclei (the images labelled "Hoechst") and the merged images (labeled "Merge") illustrating the detection of two markers.
FIG. 8B shows representative microscopic images illustrating immunocytochemical analysis of trophoblast stem-like cells. Hoechst dye was used to stain nuclei (the images labelled "Hoechst") and the merged images (labeled "Merge") illustrating the detection of two markers. This figure illustrates expression of markers TFAP2A and CDX2.
FIG. 8C shows representative microscopic images illustrating immunocytochemical analysis of trophoblast stem-like cells. Hoechst dye was used to stain nuclei (the images labelled "Hoechst") and the merged images (labeled "Merge") illustrating the detection of two markers. This figure illustrates expression of markers E-CADHERIN and ELF5.
FIG. 8D shows representative microscopic images illustrating immunocytochemical analysis of trophoblast stem-like cells. Hoechst dye was used to stain nuclei (the images labelled "Hoechst") and the merged images (labeled "Merge") illustrating the detection of two markers. This figure illustrates expression markers YAP1 and Ki67.

The trophoblast stem-like cells were cultured in TE3 medium with or without CEPT supplementation, and also with or without Chroman 1 supplementation. For Chroman 1 or CEPT supplementation, when the trophoblast stem-like cells were passaged, the cells were seeded into TE3 medium supplemented with either an additional 25 nM Chroman 1 (for Chroman 1 supplementation) or CEPT containing 25 nM Chroman 1 (for CEPT supplementation). Since TE3 medium already contained 25 nM Chroman 1, only another 25 nM was added either alone or as a component of CEPT, so that the total concentration of Chroman 1 in TE3 medium was 50 nM for the first 24 hours after passaging. It appeared that the trophoblast stem-like cells benefited from Chroman 1 or CEPT supplementation. The above-described experiments were reproduced, with similar results, with the trophoblast stem-like cells produced from other cell lines, such as JHU191i, JHU198i, MCW032i, and WA07. Trophoblast stem-like cells grew in colonies and showed a distinct morphology, with prominent nucleoli and dark cytoplasm, as illustrated in FIG. 7A. Immunocytochemical analysis of the trophoblast stem-like cells was performed, with some of the results illustrated in FIG. 8. The immunochemical analysis showed that the trophoblast stem-like cells expressed typical trophoblast markers, such as ELF5, GATA3, CDX2, TFAP2C, KRT7, CDX2, YAP1, and also expressed the proliferation marker Ki-67.

Example 2

Figure 9A:
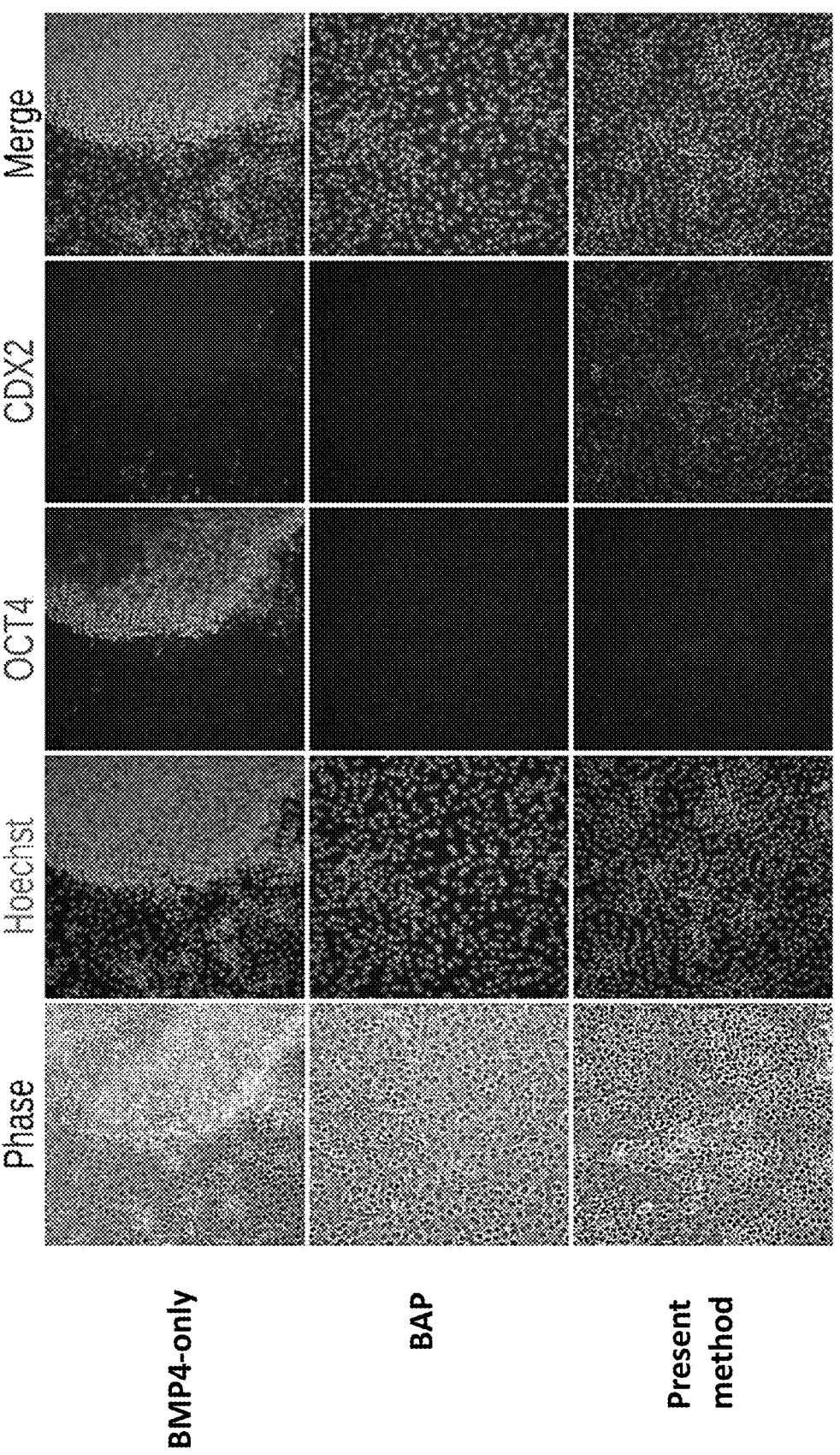
FIG. 9A shows representative microscopic images illustrating comparative analysis of the cells produced by an embodiment of a method described in the present disclosure (label "Present method") and by the previously known methods (labels "BMP4 only" and "BAP"). The other labels used are as follows: "Phase"—phase-contrast images to document the general morphology of the cells; "Hoechst"— the signal of the fluorescent dye Hoechst 33342 that labels DNA and therefore reveals the location of all cellular nuclei; "OCT4"—signal of the fluorescently labeled antibody against the pluripotency marker OCT4; "CDX2"—signal of the fluorescently labeled antibody against the trophecto-derm/trophoblast marker CDX2; "Merge" refers to the combined fluorescent signal of all markers to the left, except for "Phase"; "BRA"—signal of the fluorescently labeled antibody against the mesoderm marker Brachyury (official gene symbol TBXT; Ensembl Gene ID: ENSG00000164458).
Figure 9B:
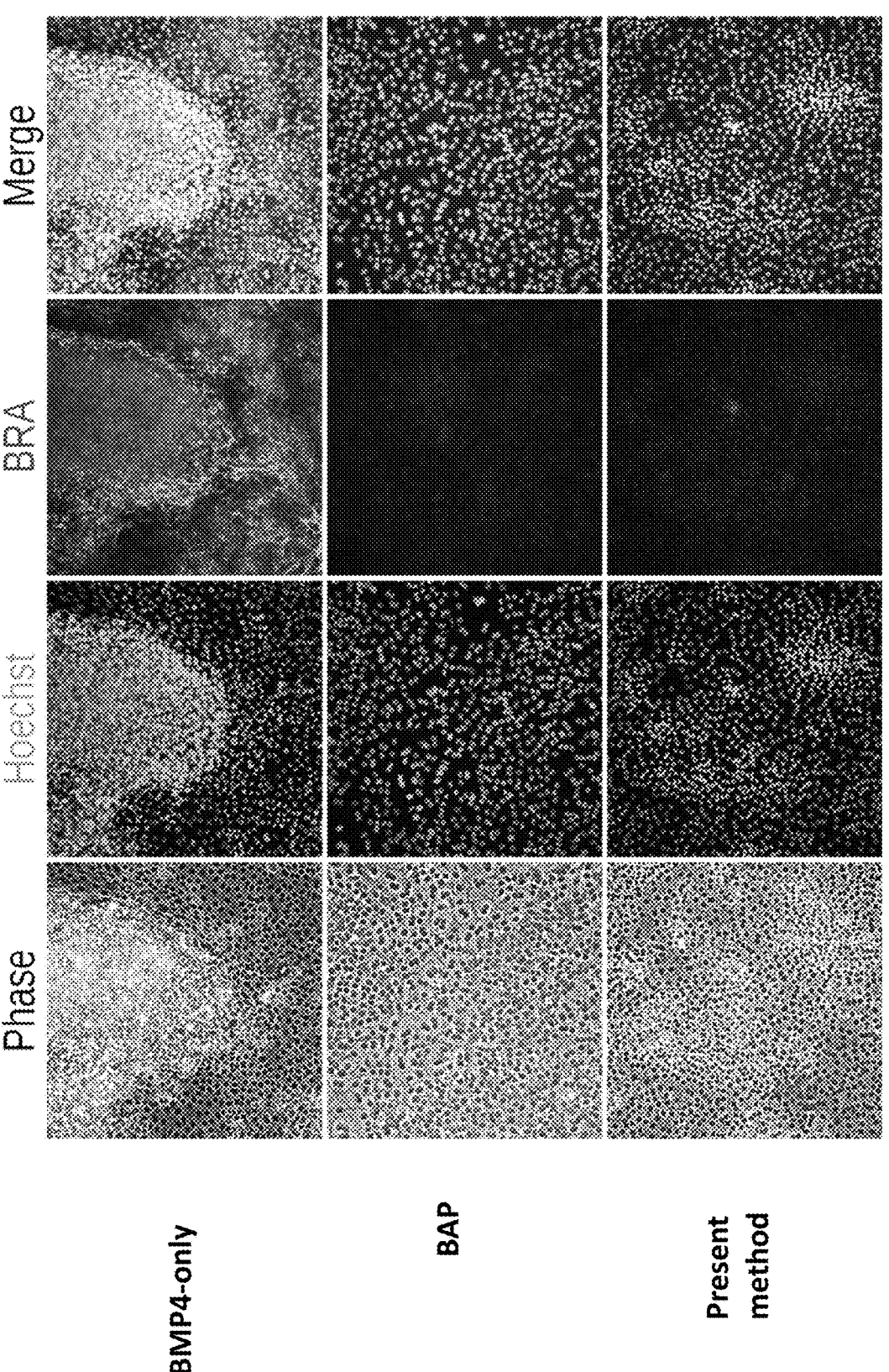
FIG. 9B shows representative microscopic images illustrating comparative analysis of the cells produced by an embodiment of a method described in the present disclosure (label "Present method") and by the previously known methods (labels "BMP4 only" and "BAP"). The other labels used are as follows: "Phase"—phase-contrast images to document the general morphology of the cells; "Hoechst"— the signal of the fluorescent dye Hoechst 33342 that labels DNA and therefore reveals the location of all cellular nuclei; "OCT4"—signal of the fluorescently labeled antibody against the pluripotency marker OCT4; "CDX2"—signal of the fluorescently labeled antibody against the trophecto-derm/trophoblast marker CDX2; "Merge" refers to the combined fluorescent signal of all markers to the left, except for "Phase"; "BRA"—signal of the fluorescently labeled antibody against the mesoderm marker Brachyury (official gene symbol TBXT; Ensembl Gene ID: ENSG00000164458).

Comparison of a Method of Differentiation of Human Pluripotent Stem Cells into Trophectoderm Lineage-Like Cells to Previously Known Approaches A method of differentiation of hPSCs into trophectoderm lineage-like cells described in Example 1 ("present method") was compared to previously known protocols for generating trophectoderm lineage-like cells. The results are illustrated in FIGS. 9A and 9B. Trophectoderm lineage-like cells were generated from WA09 hPSCs according to the method described in Example 1 (the images labeled "Present method" in FIGS. 9A and 9B) and by two previously known protocols (the images labeled "BMP4 only" and "BAP" in FIGS. 9A and 9B). Immunofluorescence analysis of WA09-derived cells was performed at "Day 5" (according to the timeline illustrated in FIG. 1). One of the previously known protocols performed ("BMP4-only") entailed using growth factor BMP4 as a sole supplement for defined E6 basal medium. Other known protocols using BMP4 as the sole supplement for undefined culture media (mouse embryonic fibroblast-conditioned medium, supplemented with Knock-Out™ Serum Replacement; see, for example, Krendl et al. "GATA2/3-TFAP2A/C transcription factor network couples human pluripotent stem cell differentiation to trophectoderm with repression of pluripotency." *Proc Natl. Acad. Sci. USA* 114:E9579-E9588 (2017)) were not selected for comparison to the present method due to high variability of the undefined media. The so-called "BAP" protocol, described, for example, in Amita et al. "Complete and unidirectional conversion of human embryonic stem cells to trophoblast by BMP4." *Proc. Natl. Acad. Sci. USA* 110:E1212-21 (2013), used undefined MEF-conditioned medium supplemented with 100 ng/ml BMP4, 1 $\mu$M A83-01 and 100 nM PD173073 (FGFR inhibitor).

As illustrated in FIG. 9A, it was demonstrated that BMP4-only protocol led to a heterogeneous population of cells, a portion of which exhibited expression of the pluripotency marker OCT4 (POU5F1). indicating that these cells failed to properly exit pluripotency. BAP protocol resulted in detectable absence of OCT4 in the resulting cells, but a marker of early trophectodermal cells CDX2 was also absent. The trophoblast identity of the cells generated using BAP protocol has previously been called to question, for example, in Lee et al. "What is trophoblast? A combination of criteria define human first-trimester trophoblast." *Stem Cell Reports* 6:257-72 (2016). In contrast, the present method ensured expression of CDX2 in the cells, while simultaneously silencing the expression of OCT4. As illustrated in FIG. 9B, the present method did not generate mesodermal cell type, in contrast to BMP4-only and BAP protocols. For example, mesodermal marker Brachyury (BRA) was not induced in the cells generated by the present method, but BMP4-only protocol resulted in strong induction of Brachyury.

Example 3

Time-Course Gene Expression Analysis

Figure 10A:
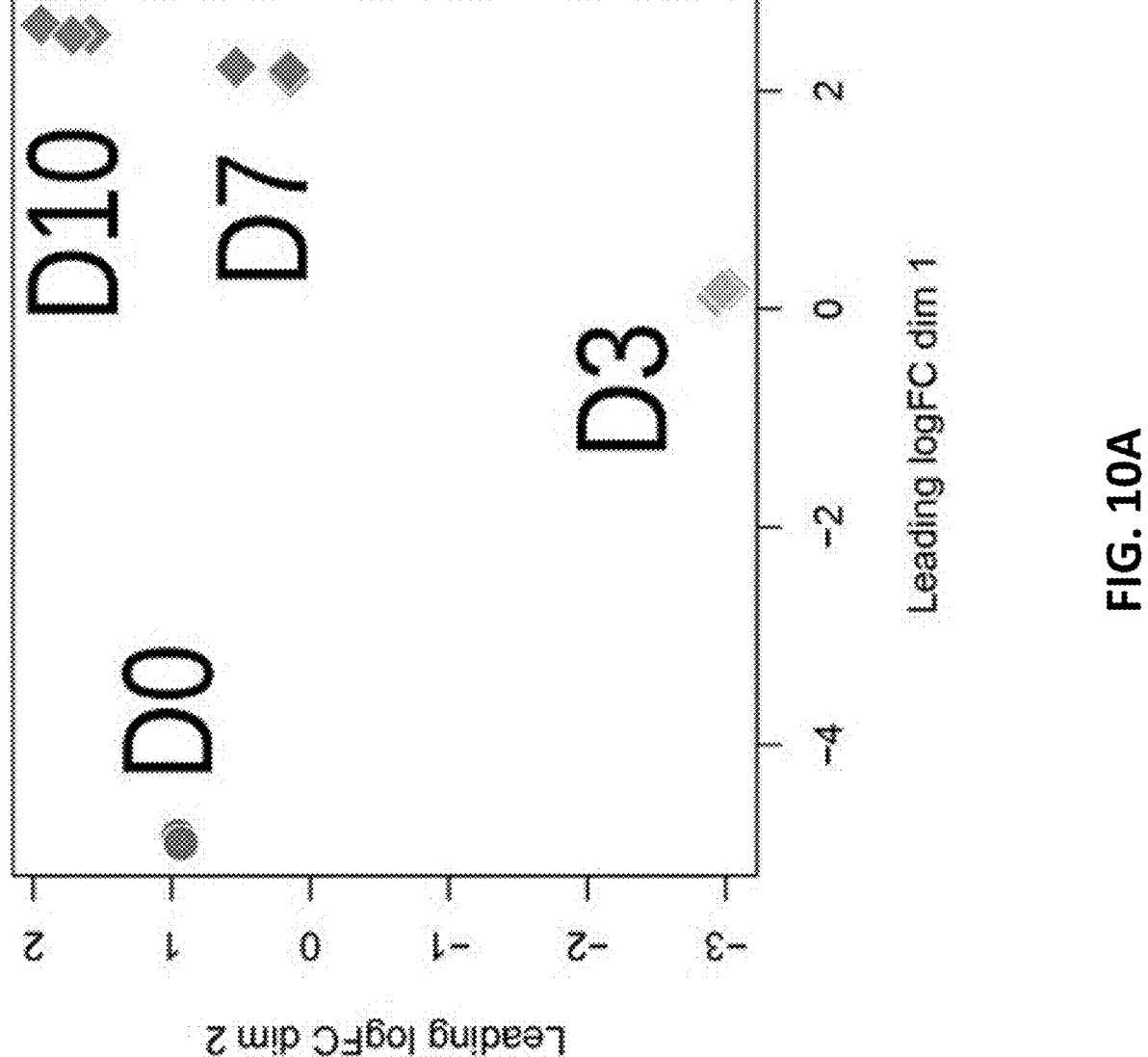
FIG. 10A illustrates the results of the comparison of the time-course gene expression profiling by RNA-seq of the cells produced by an embodiment of a method described in the present disclosure at "Day 0" (DO), "Day 3" (D3), "Day 7" (D7) and "Day 10" (D10).
Figure 10B:
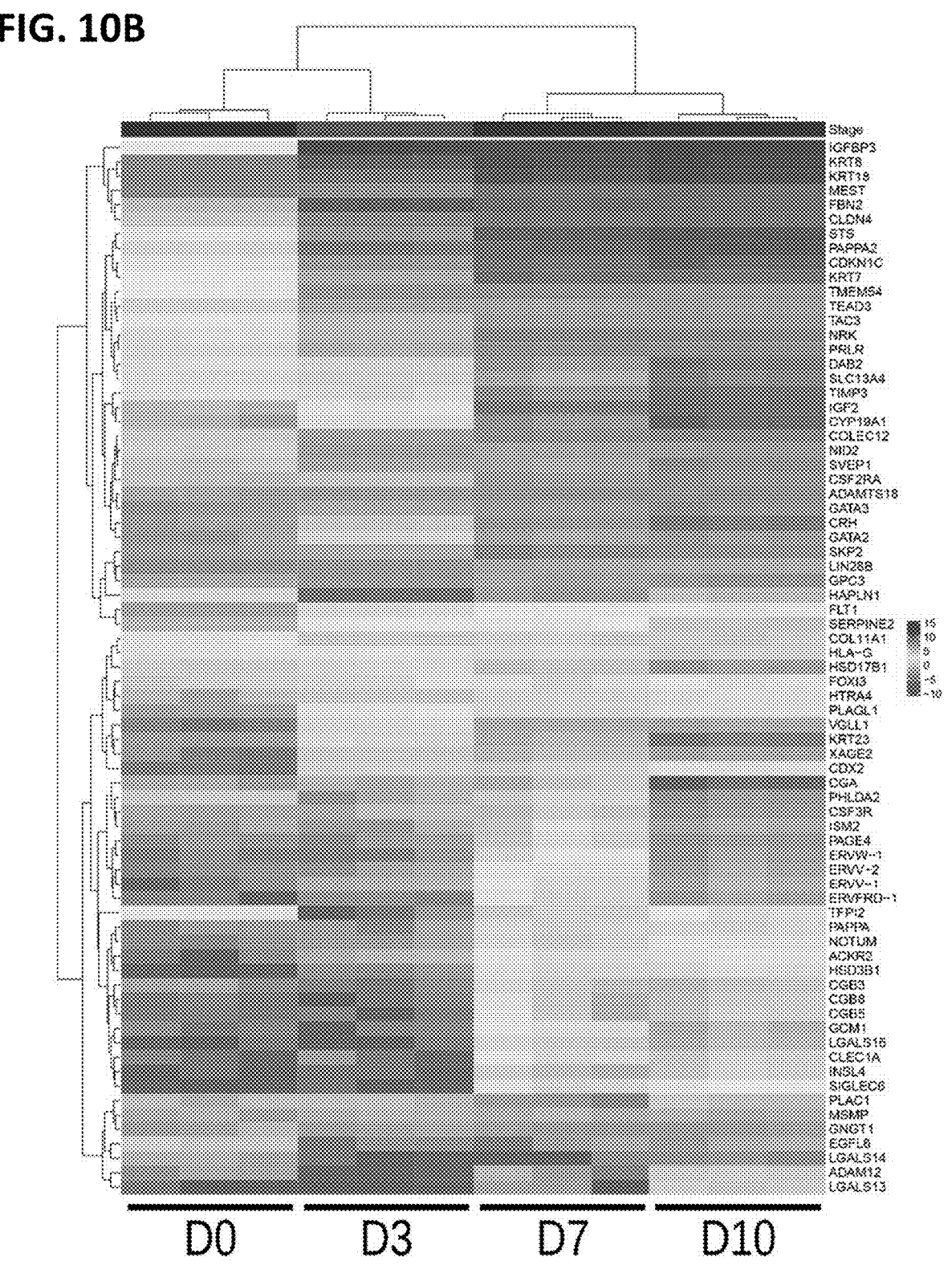
FIG. 10B illustrates the results of the comparison of the time-course gene expression profiling by RNA-seq of the cells produced by an embodiment of a method described in the present disclosure at "Day 0" (D0), "Day 3" (D3), "Day 7" (D7) and "Day 10" (D10).

The cells produced according to the procedures described in Example 1 were characterized by time-course gene expression accomplished by RNA-sequencing ("RNA-seq") analysis. The results of the time-course gene expression analysis are illustrated in FIGS. 10A and 10B. As illustrated in FIG. 10A, differentiation of hPSCs into trophectoderm lineage-like cells resulted in extensive changes of the gene expression profiles. The multidimensional scaling plot of FIG. 10A shows distinct clustering of replicate samples collected on "Days 0, 3, 7 and 10" (according to the timeline illustrated in FIG. 1), which are labeled, respectively, D0, D3, D7 and D10 in FIGS. 10A and 10B. As illustrated in FIG. 10B, among the most differentially expressed genes were the genes known to specify trophectoderm and a majority of the 78 placenta-enriched genes identified by the Protein Atlas, such as IGFBP3, KRT18, PAPPA2, TEAD3, DAB2, Insulin Like Growth Factor 2 (IGF2; Ensembl Gene ID: ENSG00000167244), GATA Binding Protein 2 (GATA2; Ensembl Gene ID: ENSG00000179348), GATA3, TFAP2A, Transcription Factor AP-2 Beta (TFAP2B; Ensembl Gene ID: ENSG00000008196), TFAP2C, CGA, Chorionic Gonadotropin Subunit Beta (CGB), and several endogenous retroviral genes, including Endogenous Retrovirus Group W Member 1, Envelope (ERVW-1; Ensembl Gene ID: ENSG00000242950) and Endogenous Retrovirus Group FRD Member 1, Envelope (ERVFRD-1; Ensembl Gene ID: ENSG00000244476) also known as syncytin-1 and 2, respectively, which are responsible for cellular fusion into syncytiotrophoblast). Multiple genes with solute carrier or steroid hormone synthesis functions were also enriched (for example, Solute Carrier Family 40 Member 1 (SLC40A1; Ensembl Gene ID: ENSG00000138449), Solute Carrier Family 6 Member 4 (SLC6A4; Ensembl Gene ID: ENSG00000108576), Solute Carrier Family 30 Member 2 (SLC30A2; Ensembl Gene ID: ENSG00000158014), Solute Carrier Family 9 Member A2 (SLC9A2; Ensembl Gene ID: ENSG00000115616), Steroid Sulfatase (STS; Ensembl Gene ID: ENSG00000101846), Cytochrome P450 Family 11 Subfamily A Member 1 (CYP11A1; Ensembl Gene ID: ENSG00000140459), etc.).

Example 4

Comparative Gene Expression Analysis

Figure 11A:
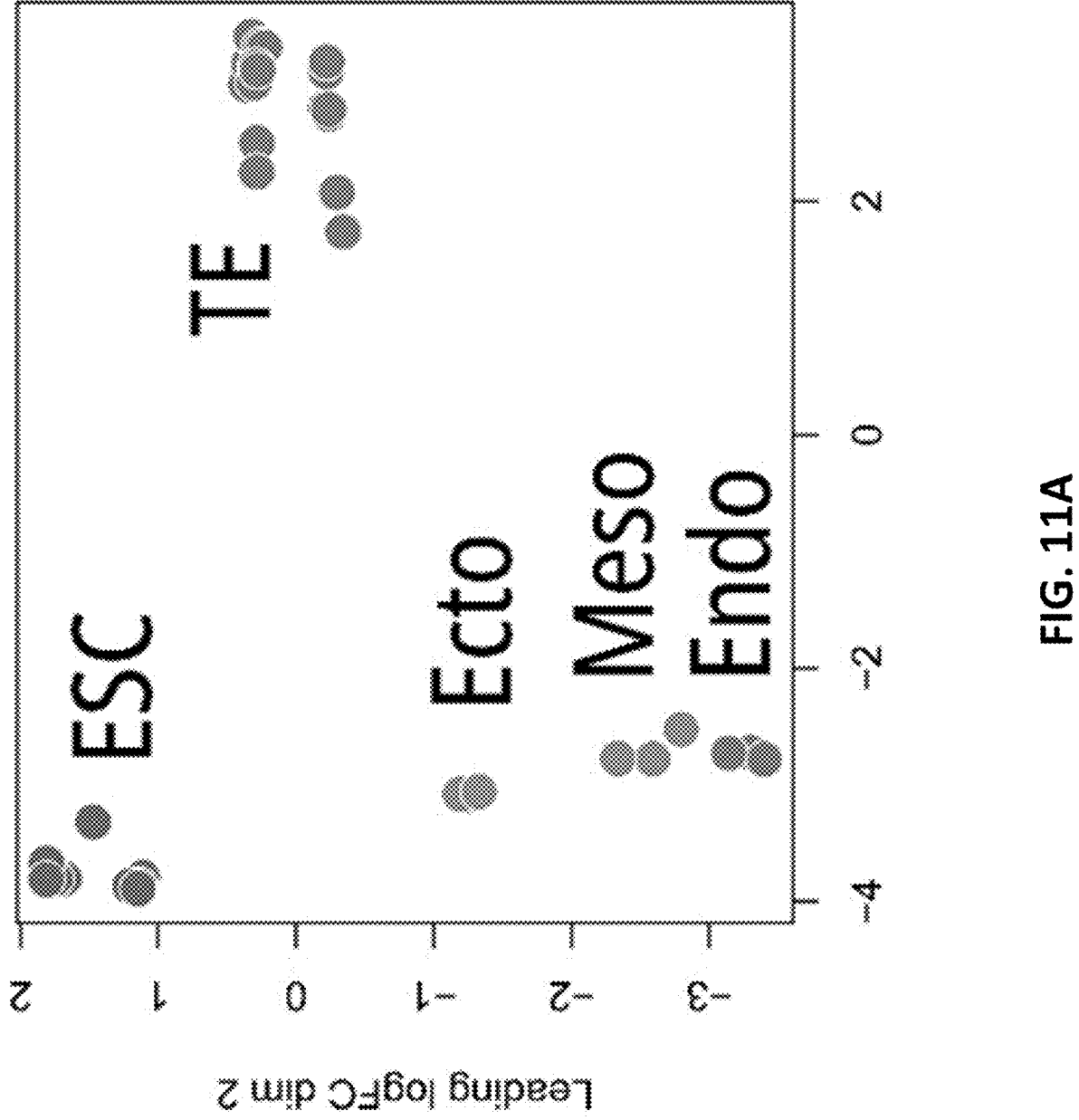
FIG. 11A illustrates the results of the comparative gene expression analysis by RNA-seq of the trophectoderm lineage-like cells produced by an embodiment of a method described in the present disclosure ("TE"), and the cells resembling the cells of other developmental lineages ("Endo," "Meso" and "Ecto," and ESCs).
Figure 11B:
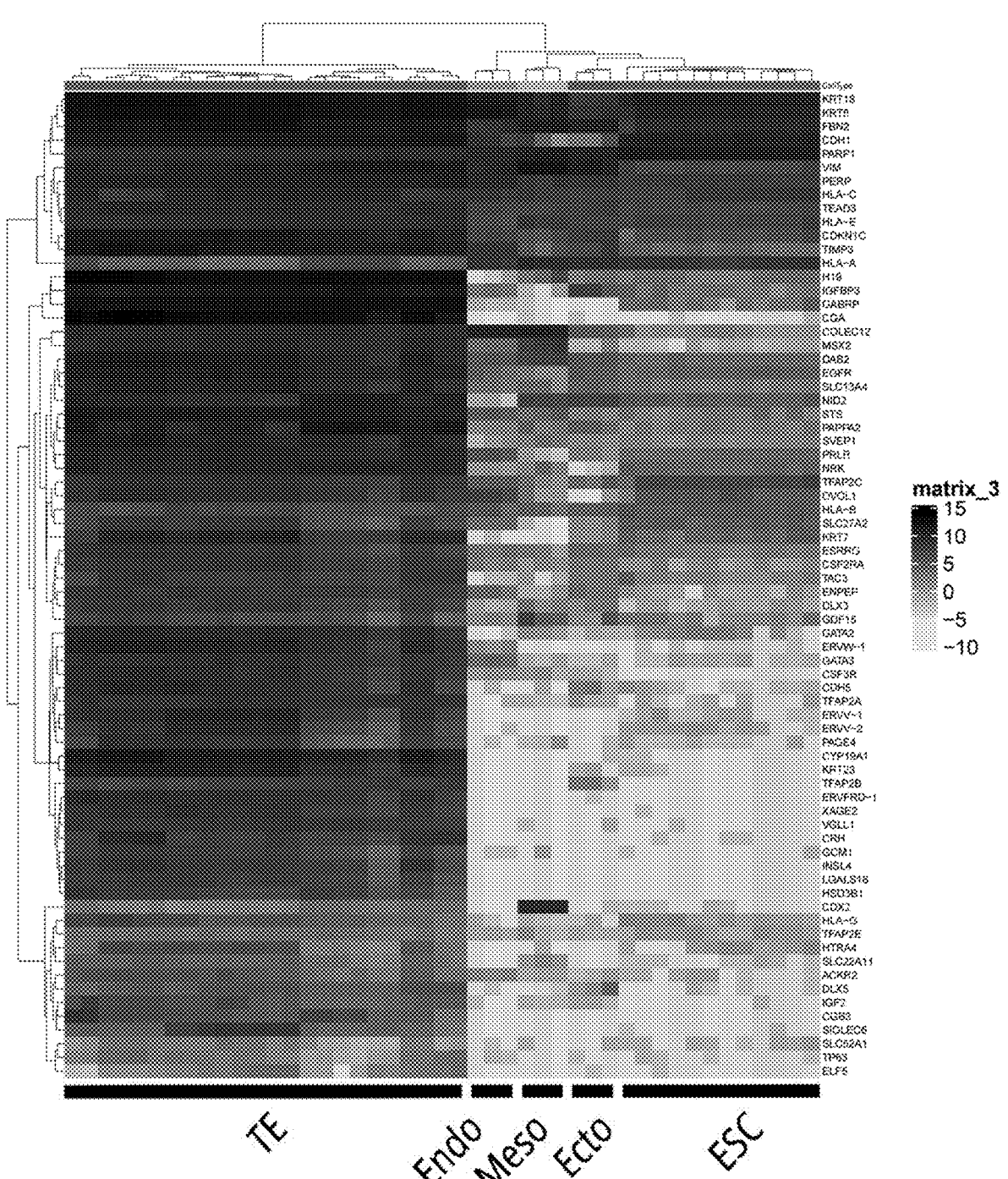
FIG. 11B illustrates the results of the comparative gene expression analysis by RNA-seq of the trophectoderm lineage-like cells produced by an embodiment of a method described in the present disclosure ("TE"), and the cells resembling the cells of other developmental lineages ("Endo," "Meso" and "Ecto," and ESCs).

The cells produced according to the procedures described in Example 1, the cells resembling those of other developmental lineages, and pluripotent stem cells were characterized by gene expression accomplished by RNA-sequencing ("RNA-seq") analysis, with the results illustrated in FIGS. 11A and 11B. As illustrated in FIG. 11A, comparison of gene expression profiles of the analyzed cells demonstrated that the molecular signature of trophectoderm lineage-like cells produced by the present methods (labelled "TE" in FIGS. 11A and 11B; the samples were collected at "Day 9" to "Day 11" according to the timeline illustrated in FIG. 1) was distinct from the molecular signature of the pluripotent stem cells (labelled "ESC" in FIGS. 11A and 11B; the samples were collected at "Day 0" according to the timeline illustrated in FIG. 1). The samples of the trophectoderm lineage-like cells and the samples of the pluripotent stem cells were derived from three cell lines (WA09, WA14 and WA17), in multiple replicates. The samples of the differentiated cells resembling those corresponding to primary somatic germ layers, which are endoderm (labelled "Endo" in FIGS. 11A and 11B), mesoderm (labelled "Meso" in FIGS. 11A and 11B), and ectoderm (labelled "Ecto" in FIGS. 11A and 11B), were derived from WA09 cell line, in triplicates. Ectoderm-like cells were produced as follows: WA09 cells were differentiated for 7 days in E6 medium supplemented with 100 nM LDN 193189 (Tocris, catalog number 6053) and 2 μM A83-01; the samples were collected at day 7 after the start of the protocol. Mesoderm-like cells were produced as follows: WA09 cells were differentiated in STEMdiff™ Mesoderm Induction Medium (05220, STEMCELL Technologies), which was used according to manufacturer's instructions; the samples were collected at day 4 or 5 after the start of the protocol. Endoderm-like cells were produced as follows: WA09 cells were differentiated using STEMdiff™ Definitive Endoderm Kit (TeSR™-E8™ Optimized, 05115, STEMCELL Technologies), which was used according to manufacturer's instructions; the samples were collected at day 4 or 5 after the start of the protocol. Replicate samples consistently clustered in the appropriate space for each developmental phenotype.

The gene set identical to the one analyzed in the experiments illustrated in FIG. 10B was plotted on the heat map shown in FIG. 11B. All the samples of the trophectoderm lineage-like cells produced by the present methods showed strong upregulation of trophectodermal/placental genes, as compared with the pluripotent stem cell samples. Several genes, such as IGFBP3, CGA, MSX2, DAB2, Pappalysin 2 (PAPPA2; Ensembl Gene ID: ENSG00000116183), GATA3, CADHERIN 5 (CDHS; Ensembl Gne ID: ENSG00000179776), and KRT7, were expressed at a similar or lower level in the samples of the pluripotent stem cells, in which they are known to perform important biological functions. To identify the differentially expressed genes, the samples of the pluripotent stem cells were compared to trophectoderm lineage-like cell samples by individual cell line (WA09, WA14, WA17), and the combined gene list was ordered by the strength of the evidence (adjusted P value). Among the most highly differentially expressed genes were the genes previously identified as specific for or enriched in trophectoderm and placental tissues. Since genes have different functions in different contexts, it is considered normal for them to be expressed in multiple cell types at varying levels, such as PARP1 or CDX2. In the present experiments, expression of CDX2 was observed at a moderate level in trophectoderm lineage-like cells, but at a high level in mesoderm-like cells, as illustrated in FIG. 11B.

Example 5

Functional Characterization

Figure 12:
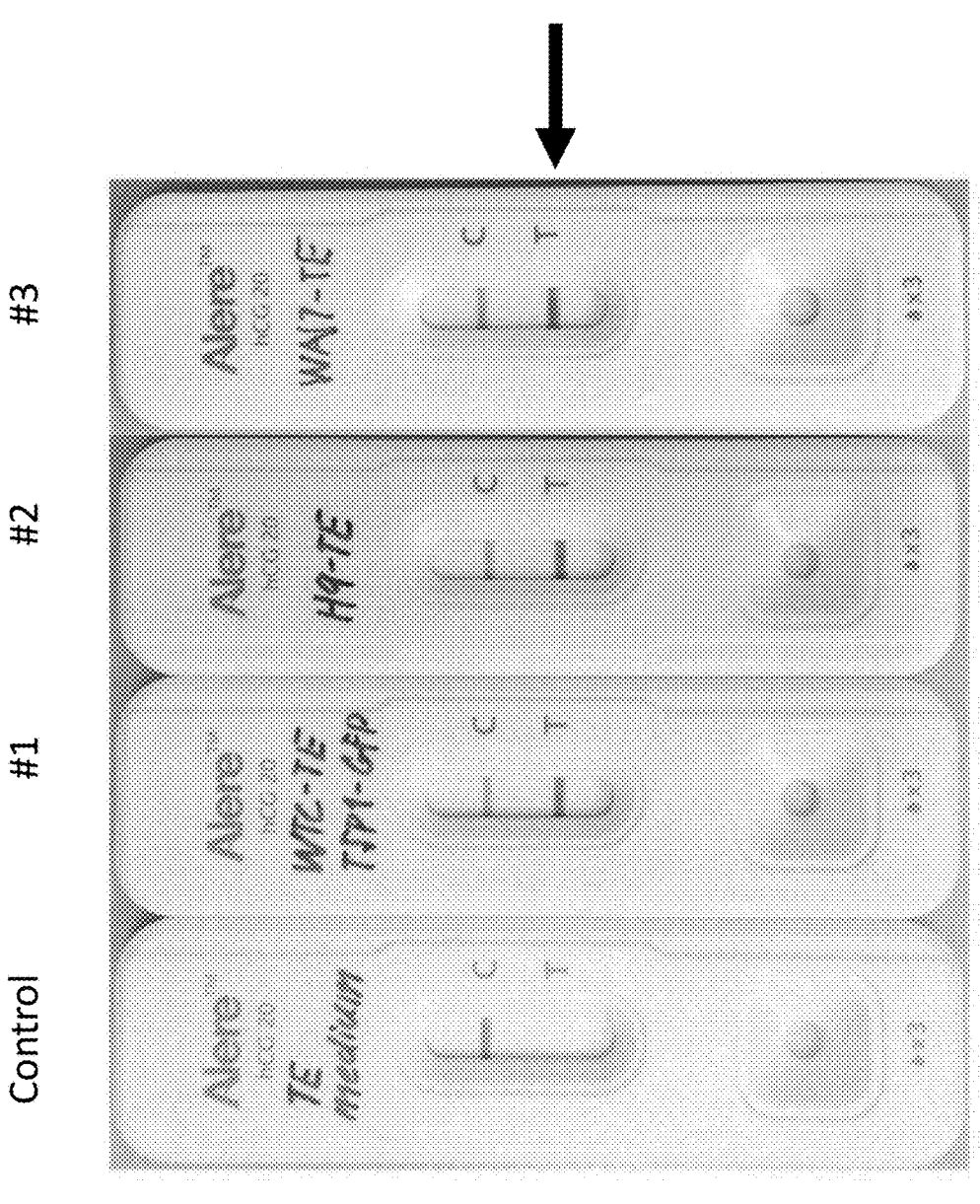
FIG. 12 shows photographic images illustrating human chorionic gonadotropin hormone secretion by syncytiotrophoblast-like structures produced by embodiments of a methods described in the present disclosure. Hormone secretion (indicated by an arrow) was demonstrated by using an over-the-counter pregnancy test. TE medium (medium only) was used as control.
Figure 13:
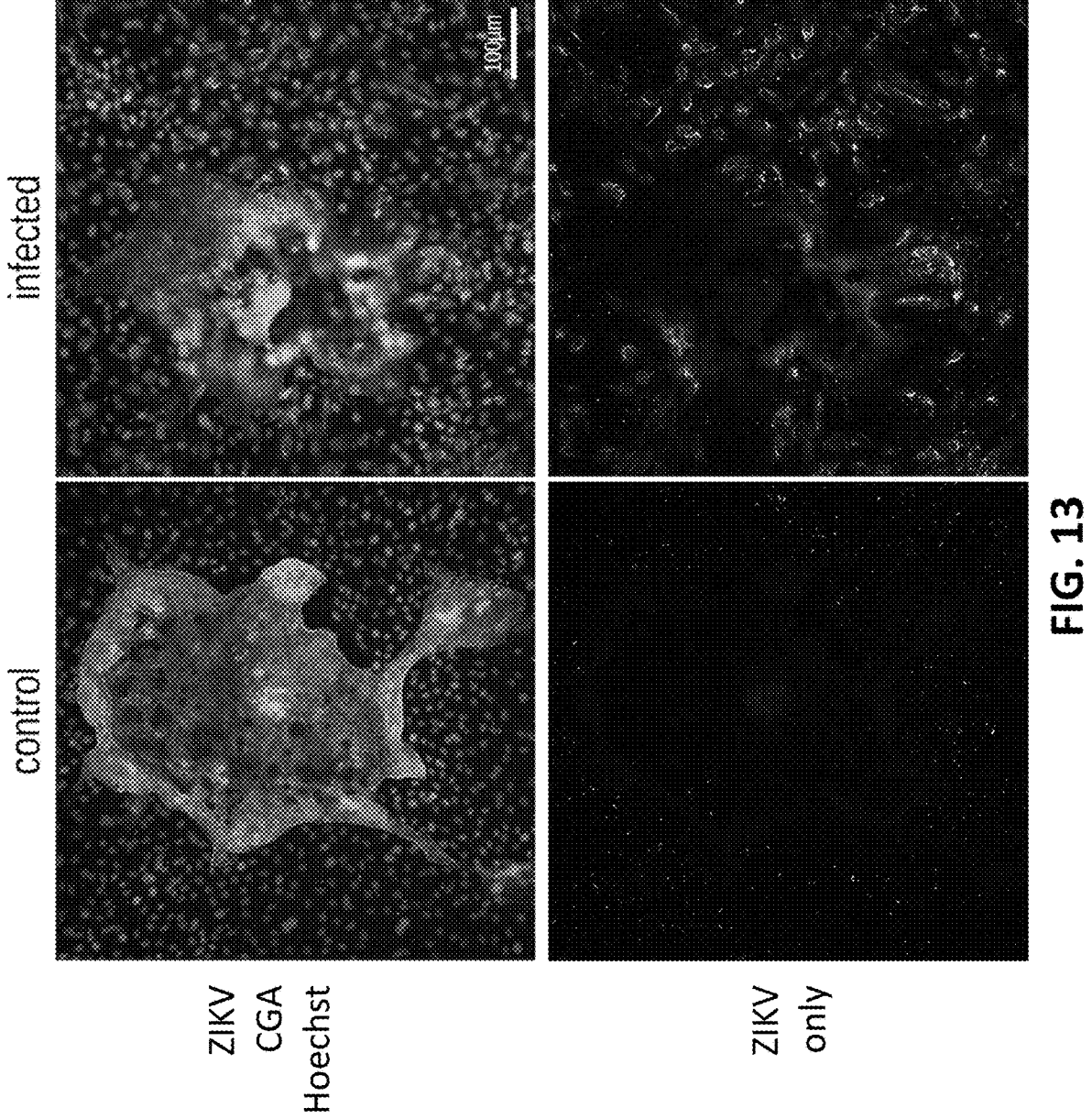
FIG. 13 shows representative photographic images illustrating susceptibility of trophectoderm lineage-like cells produced by the methods described in the present disclosure to Zika virus infection.

Functional analysis of the cells produced according to the procedures described in Example 1 was performed, with the results illustrated in FIGS. 12 and 13 and discussed below. One type of experiments tested human chorionic gonadotropin hormone secretion by syncytiotrophoblast-like structures produced by methods described in Example 1. FIG. 12 illustrates the results of the above experiments, in which an over-the-counter pregnancy test was used to test, at "Day 10" (according to the timeline illustrated in FIG. 1), the supernatant of the cells produced by the methods described in Example 1. The labels #1, #2, #3 denote the tests performed on the trophectoderm lineage-like cells derived from three different pluripotent cells: WTC iPSC line, WA09 and WA17, respectively. The label "Control" denotes the test performed on medium only, with no cells. The arrow indicates a positive test in three different pluripotent stem cell lines, confirming human chorionic gonadotropin secretion in the culture medium by syncytiotrophoblast-like structures.

Another type of experiments tested susceptibility of trophectoderm-like cells produced by the methods described in Example 1 to Zika virus infection. FIG. 13 illustrates the results of an exemplary experiment, in which trophectoderm-like cells were produced according to the method described in Example 1 from human pluripotent stem cells, and, on "Day 11" (according to the timeline illustrated in FIG. 1), infected and incubated with Zika virus (Ugandan M766 strain; viral titer $1.6 \times 10^8$ PFU/mL) for 24 hours. Immunocytochemical analysis using a specific antibody showed that viral envelope protein ZIKV Envelope protein (Q91KX7_ZIKV) was abundant in the cytoplasm of infected cells. In some experiments (the results illustrated in the top two images of FIG. 13), hPSC-derived cultures—uninfected ("control") and infected with ZIKV for 24 h ("infected")—were stained with antibodies against ZIKV Envelope protein ("ZIKV") and against syncytiotrophoblast marker CGA ("CGA"). Cell nuclei were visualized with Hoechst dye ("Hoechst"). In other experiments (the results illustrated in the bottom two images of FIG. 13), hPSC-derived cultures—uninfected ("control") and infected with ZIKV for 24 h ("infected")—were stained with antibodies against ZIKV Envelope protein only ("ZIKV only").

Example 6

Differentiation of Trophoblast Stem Cells (TSCs) into Extravillous Trophoblast (EVT) and Syncytiotrophoblast (STB)

For the purpose of EVT differentiation, TSC were cultured in TE3 medium in hypoxia (2% $O_2$) for at least 1 passage (3 days). Then the cultures were dissociated with Accutase for 15-20 min and seeded at a density of $6 \times 10^5/$ cm² in EVT medium on vitronectin-coated culture plates. After 6 days of culture, the cells were dissociated with Accutase, replated at a density of $2 \times 10^5/cm²$ in EVT medium and cultured for another 6 days. Passaging and culture for 6 days was repeated as necessary until proliferation slowed down and spindle-shaped cells emerged (2-3 passages total). The EVT medium was changed every other day and the cells were incubated at 37° C., 5% $CO_2$ and 2% $O_2$.

For STB differentiation, TSC cultures were dissociated with Accutase for 10-15 min, seeded at a density of $1 \times 10^5/$ cm² in STB medium and cultured for 3-4 days at 37° C., 5% $CO_2$ and 21% $O_2$.

Components for EVT differentiation conditions included a base medium, a cell culture surface coating, chroman 1, Recombinant Human Epidermal Growth Factor (EGF), Recombinant Human Neuregulin 1/Heregulin 1 Protein (NRG1/HRG1), and Recombinant Human TGF-beta 1 Protein, as described herein below. Base medium: Essential 6 catalog number, company: A1516401, Thermo-Fisher Scientific. Cell Culture Surface Coating: Recombinant Human Vitronectin catalog number, company: A14700, Thermo-Fisher Scientific; Concentration used: 0.5 µg/cm²; Concentration range: 0.1 µg/cm²-10 µg/cm². Chroman 1 catalog number, company: HY-15392, MedChemExpress; Concentration used: 50 nM; Concentration range: 1 nM-1 µM. Recombinant Human Epidermal Growth Factor (EGF) catalog number, company: 236-EG-200, R&D Systems; Concentration used: 50 ng/ml; Concentration range: 1 ng/ml-500 ng/ml. Recombinant Human Neuregulin 1/Heregulin 1 Protein (NRG1/HRG1) catalog number, company: 5898-NR-050, R&D Systems; Concentration used: 100 ng/ml; Concentration range: 1 ng/ml-500 ng/ml. Recombinant Human TGF-beta 1 Protein catalog number, company: 7754-BH-100, R&D Systems; Concentration used: 100 ng/ml; Concentration range: 1 ng/ml-500 ng/ml.

Components for STB differentiation conditions included a base medium, a cell culture surface coating, chroman 1, and forskolin, as described herein below. Base medium: Essential 6, catalog number, company: A1516401, Thermo-Fisher Scientific. Cell Culture Surface Coating: Recombinant Human Vitronectin, catalog number, company: A14700, Thermo-Fisher Scientific; Concentration used: 0.5 µg/cm²; Concentration range: 0.1 µg/cm²-10 µg/cm². Chroman 1 catalog number, company: HY-15392, MedChemExpress; Concentration used: 50 nM; Concentration range: 1 nM-1 µM. Forskolin catalog number, company: 1099, Tocris Biosciences (R&D Systems); Concentration used: 10 µM; Concentration range: 100 nM-50 µM.

Figure 14:
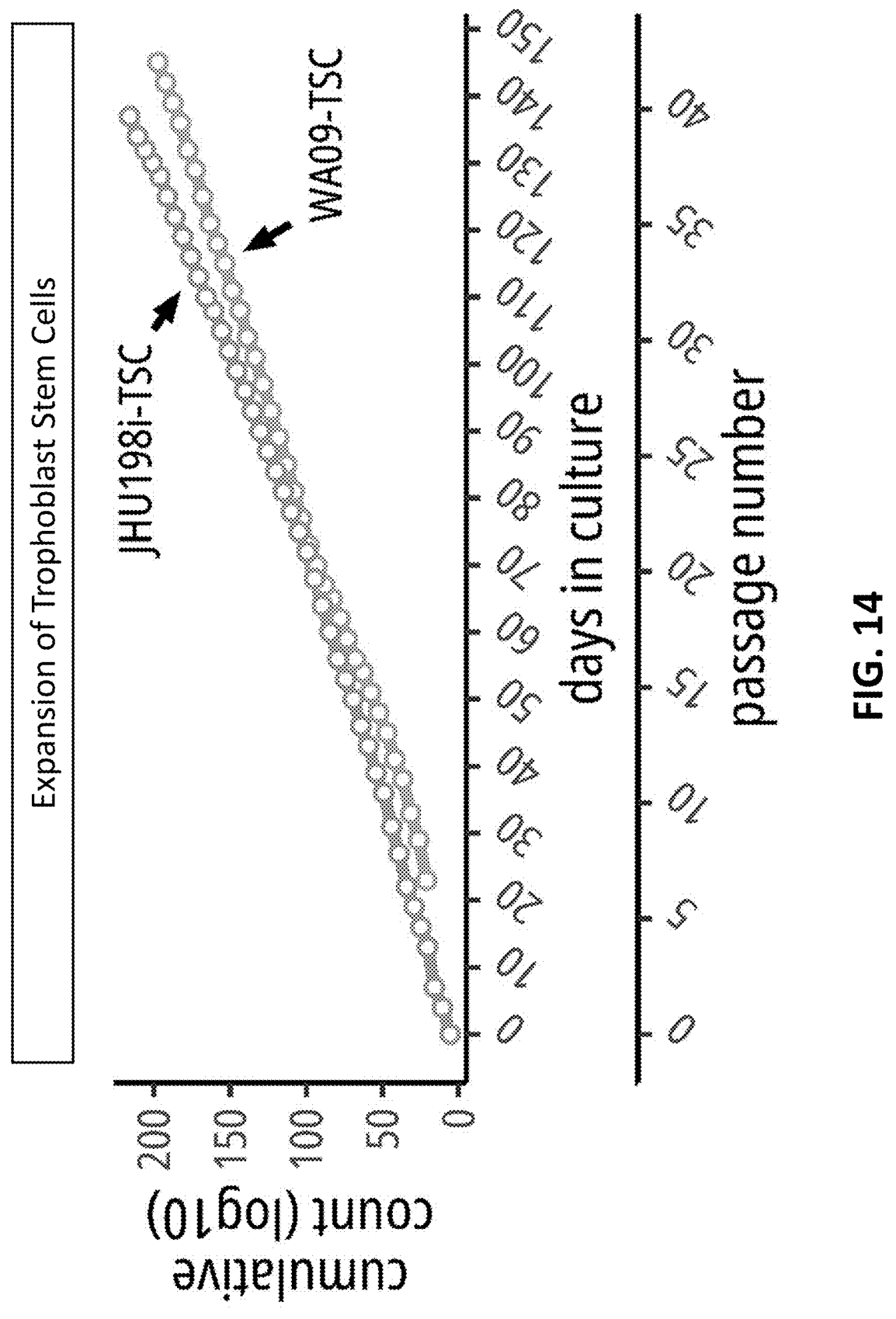
FIG. 14 shows a graphical depiction of long-term cell passaging and expansion of two representative TSC lines derived from human pluripotent stem cells as described in the present disclosure.
Figure 15A:
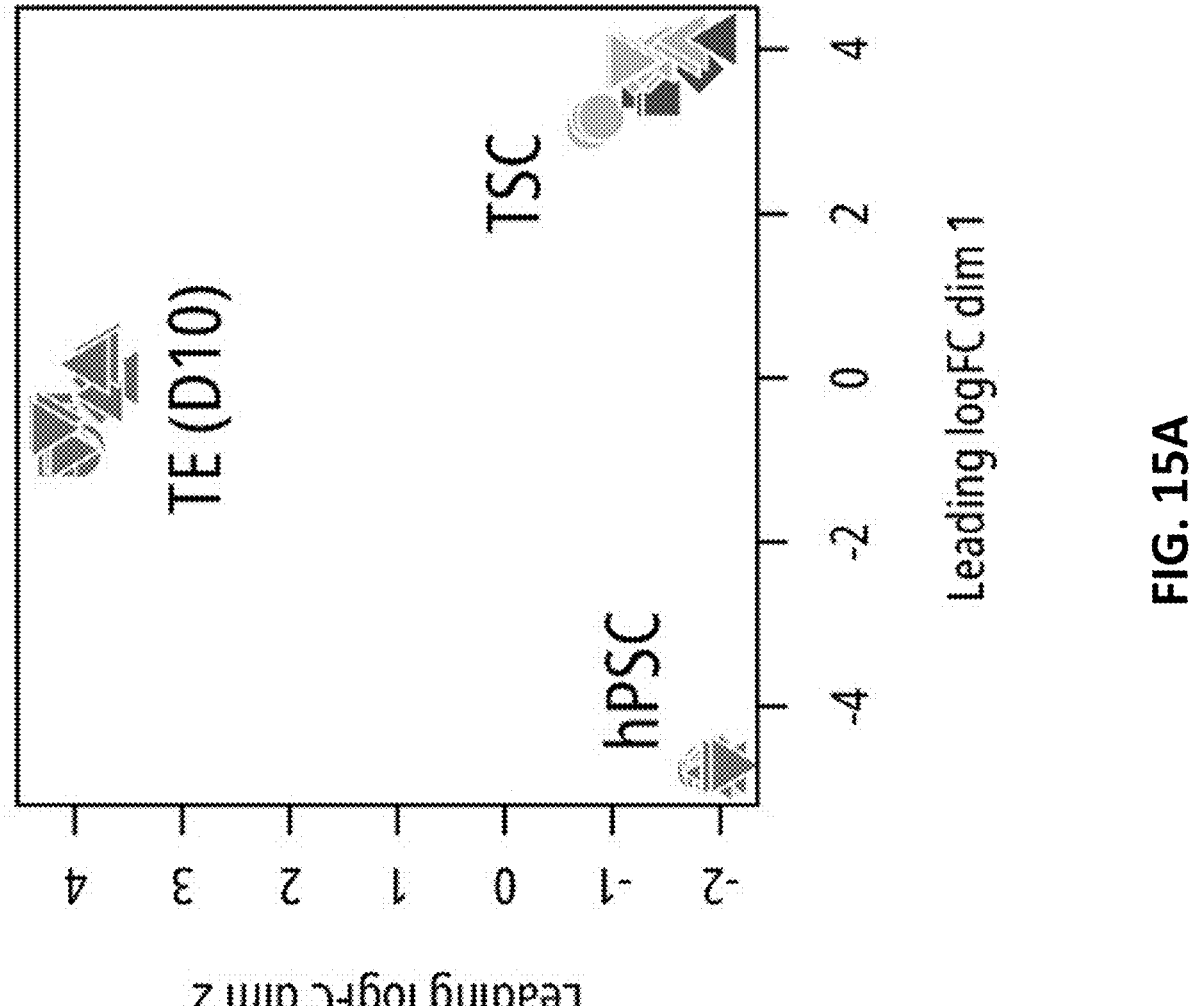
FIG. 15A illustrates an MDS plot showing distinct clustering of hPSC, TE (Day 10) and TSC samples, regardless of their genetic background. The cell type groups were derived from 2 hESC (WA07 and WA09) lines and 3 human iPSC lines (JHU191i, JHU198i, MCW032i). Early-passage (7-10) and late-passage samples were included (16-21) and 15B illustrate the results of representative RNA sequencing of hPSC-derived trophectoderm (Day10) and expanded trophoblast stem cells as described in the present disclosure.
Figure 15B:
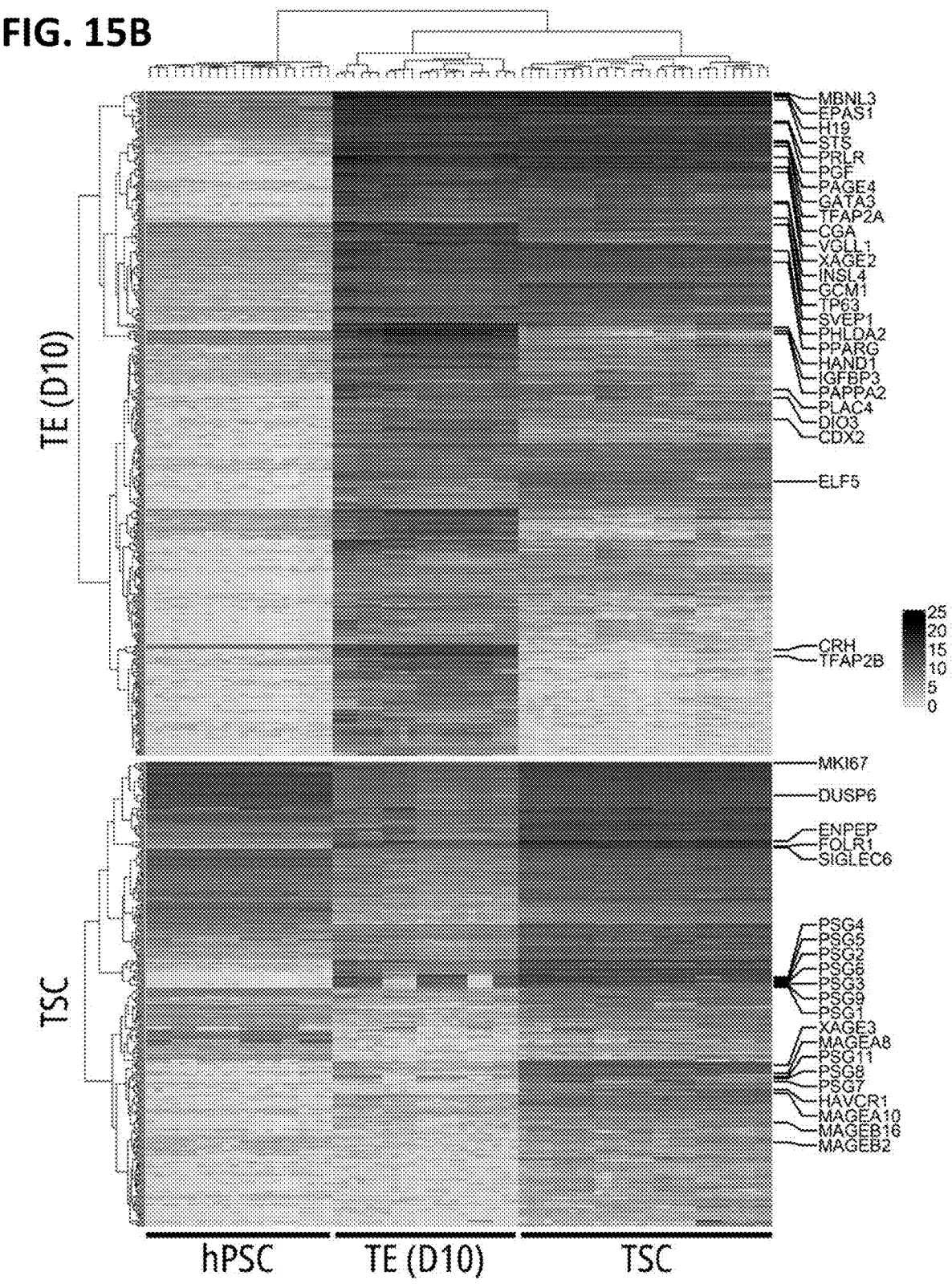
FIG. 15B illustrates a heatmap of top differentially expressed genes (nearly 700) in TE D10 compared with hPSC (top, log 2 fold change>6, FDR-adjusted P value<1× 10−4) and in TSC compared with TE D10 (bottom, log 2 fold change>3, FDR-adjusted P value<1×10−4). The expression of important trophectodermal or trophoblast markers was maintained in TSC while others were downregulated (such as CRH and TFAP2B). Among the genes uniquely upregulated in TSC were known markers associated with trophoblast, such as ENPEP, SIGLEC6, XAGE3, HAVCR1 and a number of pregnancy-specific beta-1-glycoproteins (PSG) genes.

The stepwise and controlled differentiation of human pluripotent stem cells (hPSCs), which include human embryonic stem cells (hESCs) and induced pluripotent stem cells (iPSCs), enables the generation of cytotrophoblast (CTB), syncytiotrophoblast (STB), and self-renewing trophoblast stem cells (TSCs) that can be expanded for more than 5 months under chemically defined conditions. As shown in FIG. 14, cumulative cell counts across serial passaging show stable proliferation and expansion of two TSC lines derived from one ESC line (WA09) and one iPSC line (JHU198i) using the TE3 medium. The MDS plot shown in FIG. 15A of representative RNA sequencing of hPSC-derived trophectoderm and trophoblast stem cells illustrates distinct clustering of hPSC, TE (Day 10) and TSC samples, regardless of their genetic background. The cell type groups were derived from 2 hESC (WA07 and WA09) lines and 3 human iPSC lines (JHU191i, JHU198i, MCW032i). Early-passage (7-10) and late-passage samples were included (16-21). FIG. 15B illustrates the heatmap of top differentially expressed genes (nearly 700) in TE D10 compared with hPSC (top, log 2 fold change>6, FDR-adjusted P value<1×10-4) and in TSC compared with TE D10 (bottom, log 2 fold change>3, FDR-adjusted P value<1×10-4). The expression of important trophectodermal or trophoblast markers was maintained in TSC while others were downregulated (such as CRH and TFAP2B). Among the genes uniquely upregulated in TSC were known markers associated with trophoblast, such as ENPEP, SIGLEC6, XAGE3, HAVCR1 and a number of pregnancy-specific beta-1-glycoproteins (PSG) genes.

Figure 16:
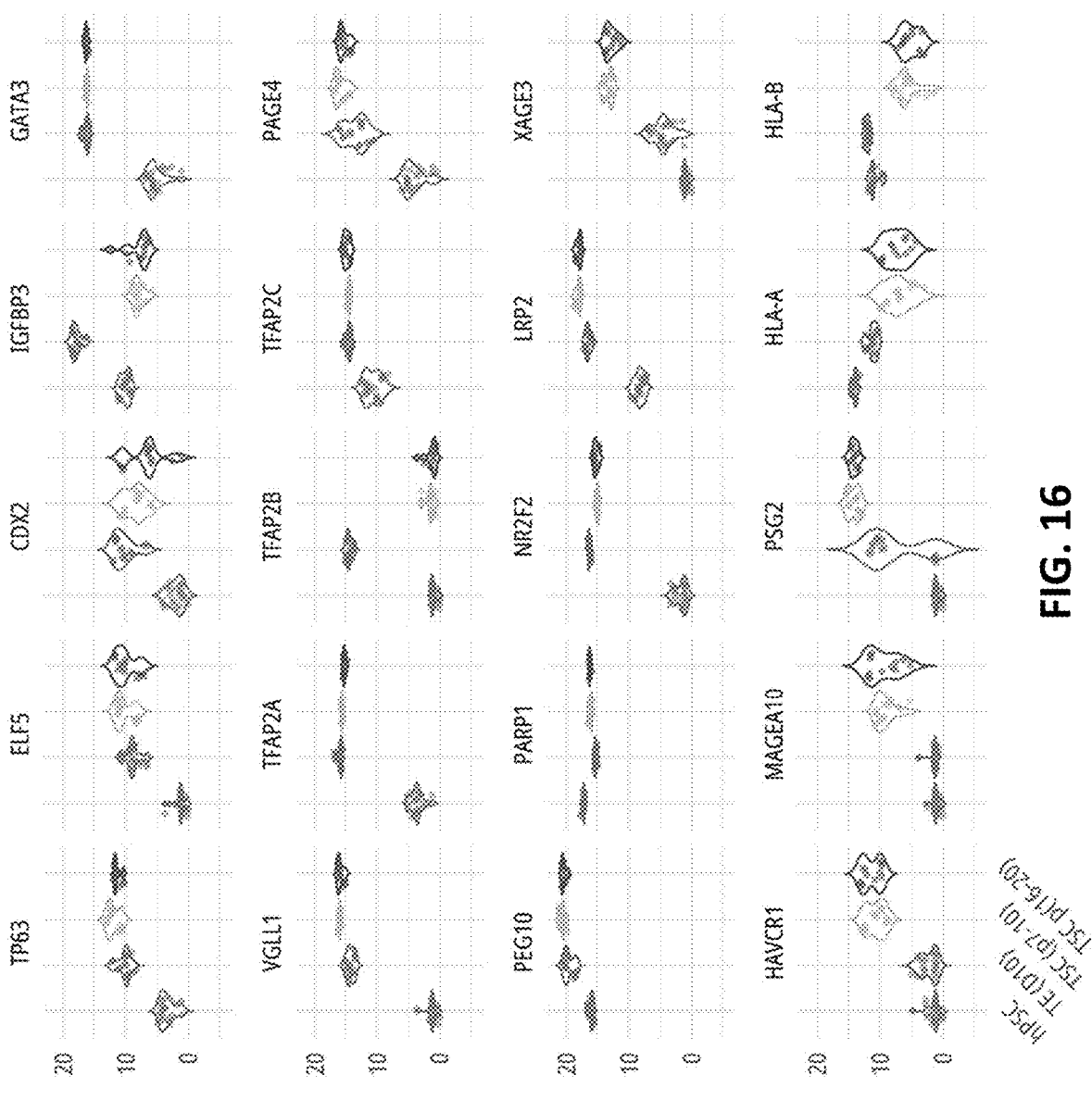
FIG. 16 illustrates the results of representative trophoblast marker expression measured by RNA sequencing of hPSC-derived trophectoderm (Day 10) and trophoblast stem cells at different passages (p7-10 and p16-20) as described in the present disclosure.
Figure 17A:
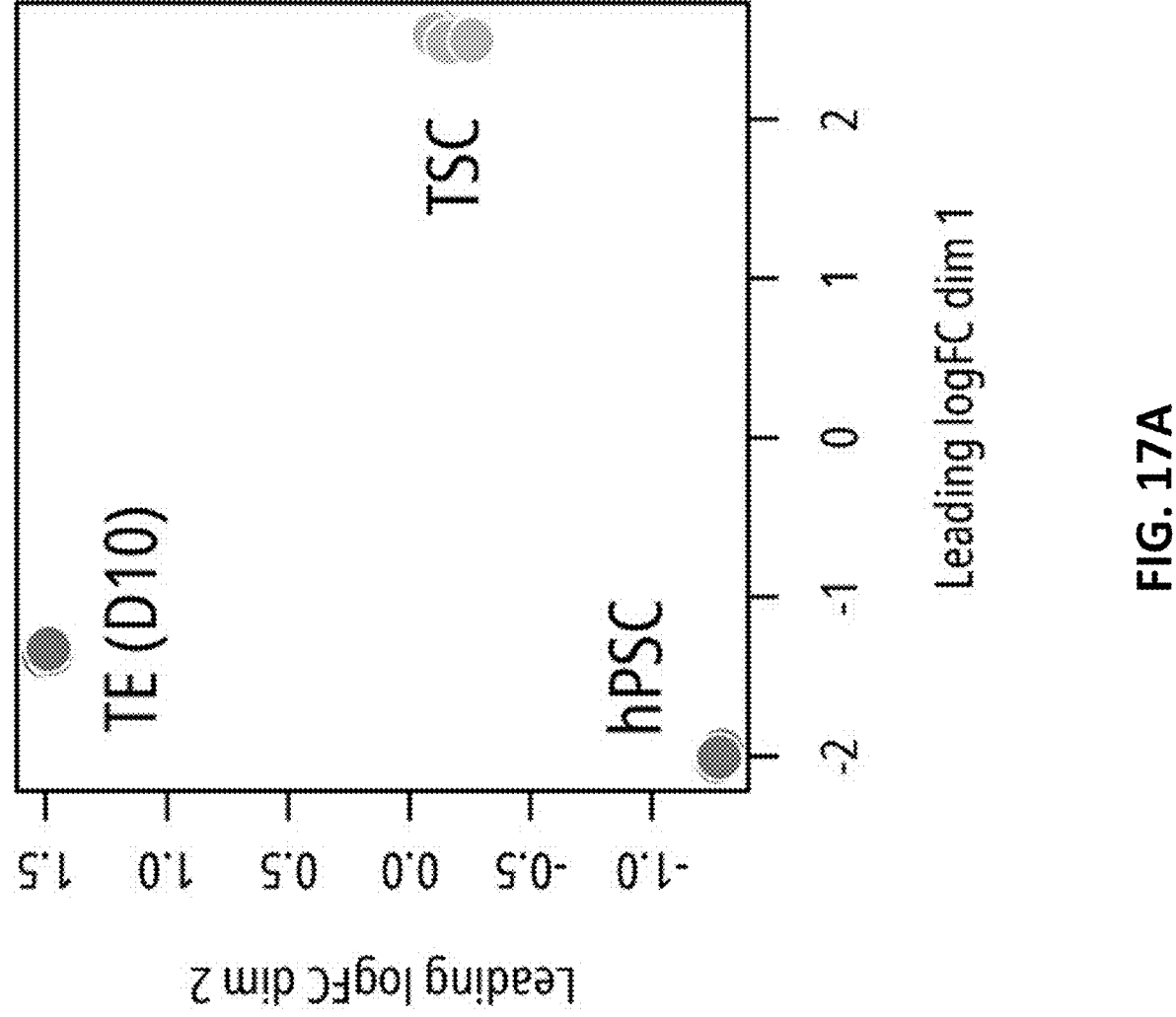
FIG. 17A illustrates an MDS plot revealed distinct clustering of hPSC, TE D10 and TSC (JHU198i line) based on their miRNA-seq transcriptional profiles.
Figure 17B:
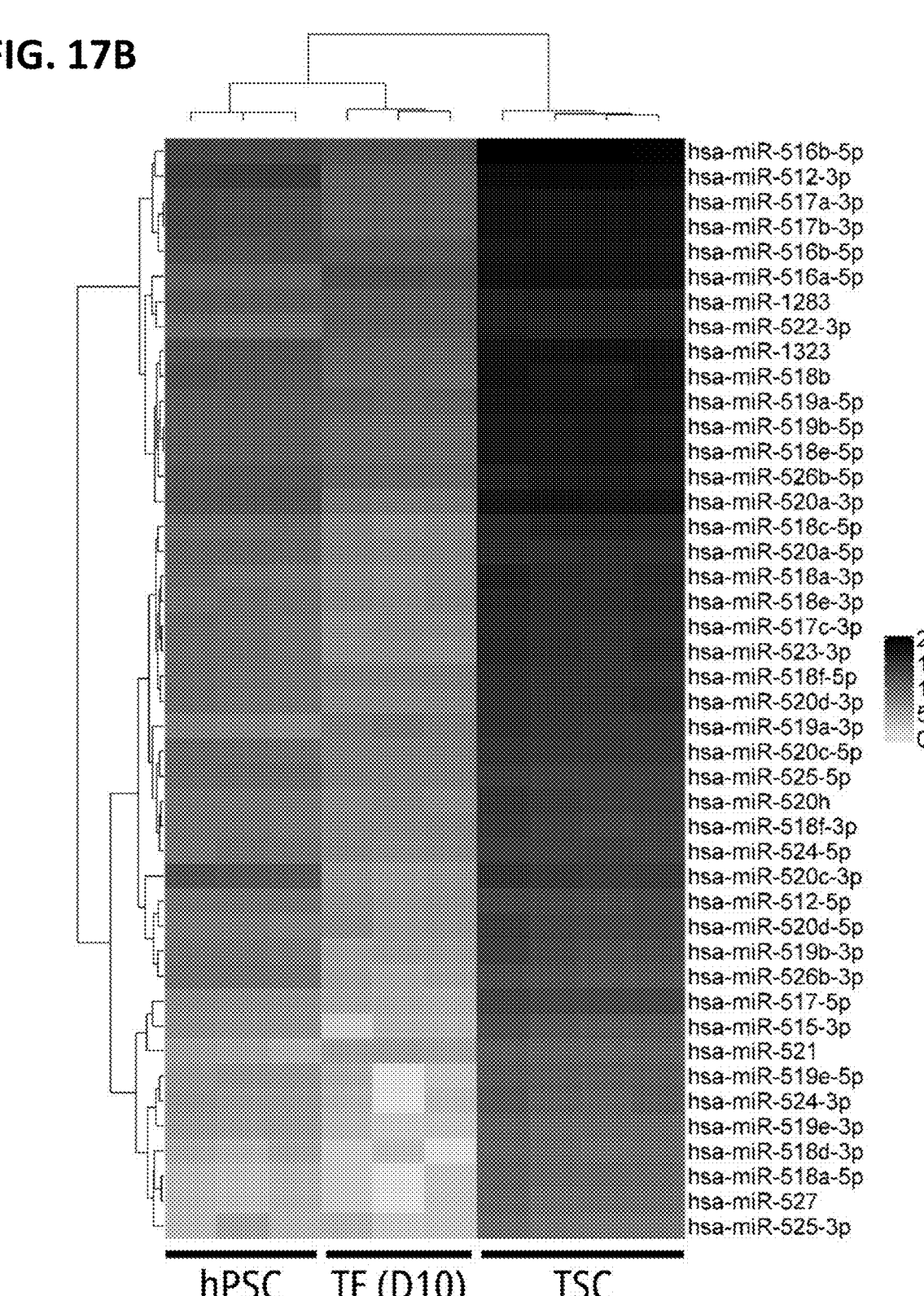
FIG. 17B is a heatmap of the expression of microRNAs of the C19MC cluster showed their marked upregulation in TSC, a criterion of bona-fide trophoblast, in TSC compared with hPSC and TE D10 and 17B illustrate the results of representative micro-RNA sequencing of hPSC-derived trophectoderm (Day 10) and expanded trophoblast stem cells as described in the present disclosure.
Figure 18:
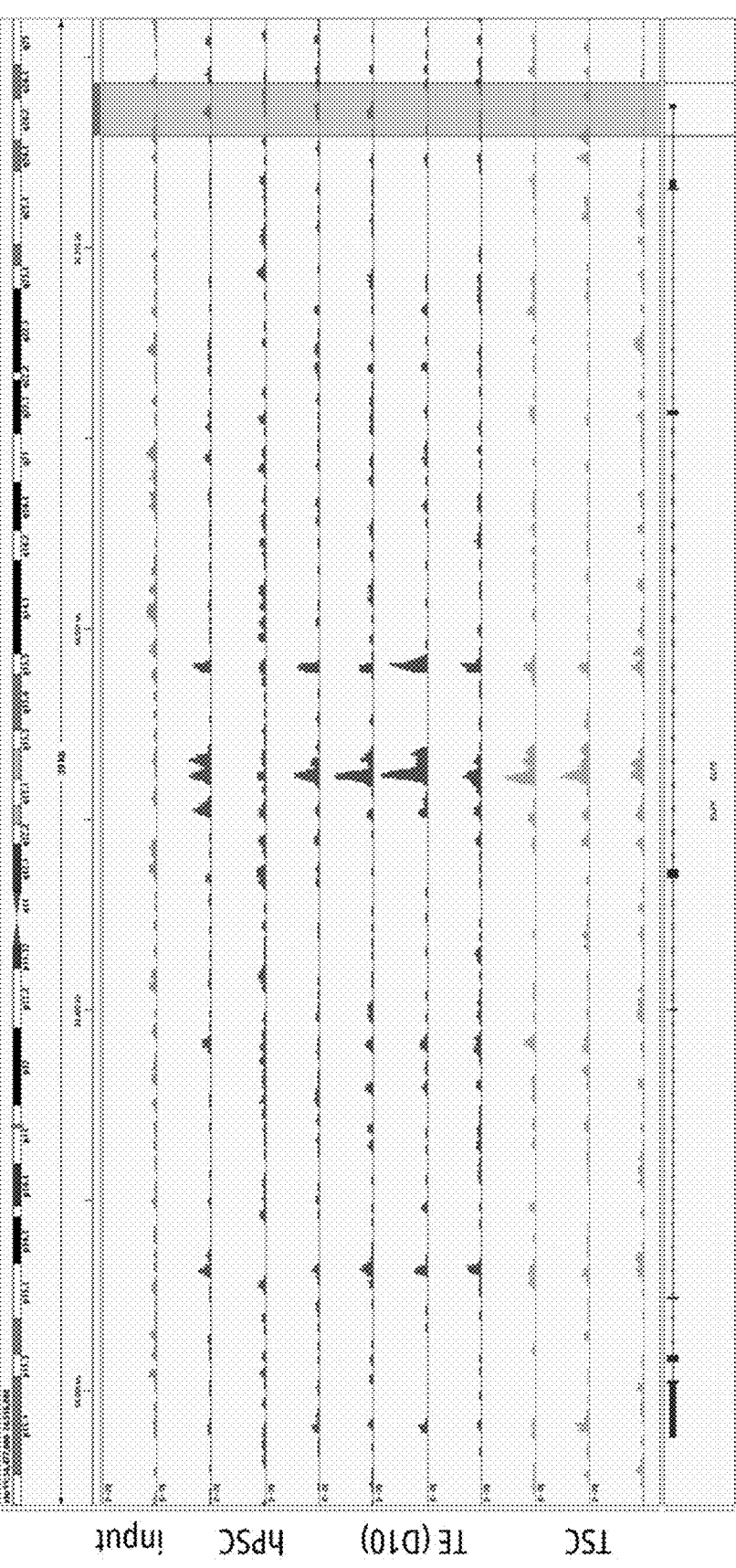
FIG. 18 shows representative methylation status of the promoter of ELF5, an important gene for trophectoderm lineage specification as described in the present disclosure.

According to FIG. 16, all markers shown are characteristic of trophectoderm or cytotrophoblast (trophoblast stem cell) population in the placenta villi. TSC at early passages (p7-10) and later passages (p16-20) were included. IGFBP3 and TFAP2B were activated only in TE (D10) while markers such as XAGE3, HAVCR1 or multiple PSG genes were activated only in proliferative TSC. HLA-A and -B were downregulated in TSC compared with TE p0 and hPSC control. This downregulation represents one of the molecular trophoblast criteria. Markers PEG10 and PARP1 were expressed in hPSC as well. The MDS plot shown in FIG. 17A of representative micro-RNA sequencing of hPSC-derived trophectoderm and trophoblast stem cells revealed distinct clustering of hPSC, TE D10 and TSC (JHU198i line) based on their miRNA-seq transcriptional profiles. Correspondingly, the heatmap shown in FIG. 17B of the expression of microRNAs of the C19MC cluster showed their marked upregulation in TSC, a criterion of bona-fide trophoblast, in TSC compared with hPSC and TE D10. FIG. 18 illustrates the ELF5 promoter region hypomethylation was previously identified as one of the key trophoblast criteria (Lee et al., 2016; PMD: 26862703). In agreement, ELF5 promoter was unmethylated across all samples. In addition to providing in-depth characterizations of the three placental cell types mentioned above, the present disclosure confirms that expanded TSCs are able to be differentiated into terminal cell types, including STB and extra-villous cytotrophoblast (EVT), as described herein below.

Figure 19:
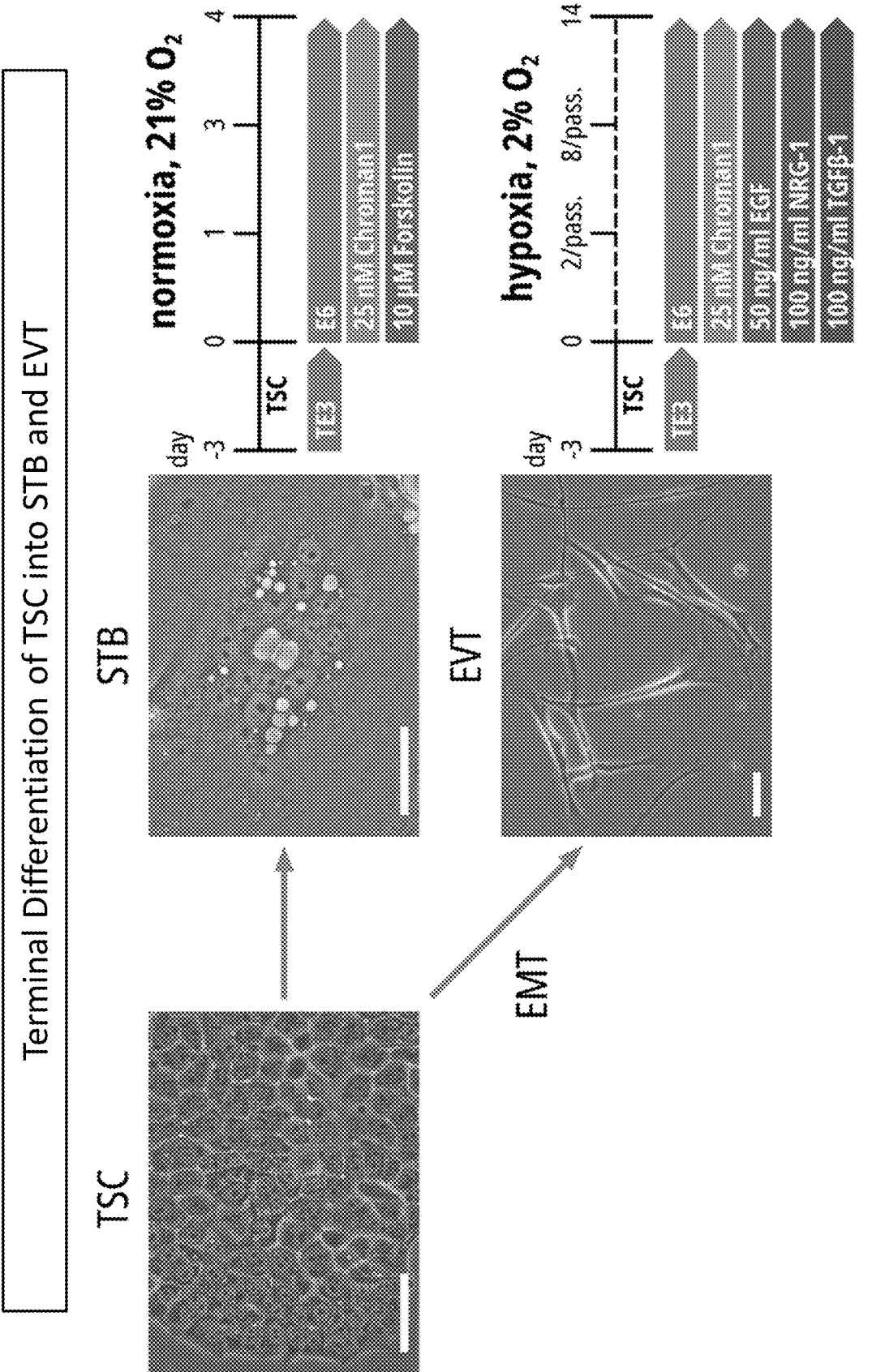
FIG. 19 shows exemplary protocol embodiments for terminal differentiation of hPSC-derived TSC into extravillous trophoblast (EVT) and syncytiotrophoblast (STB) as described in the present disclosure.
Figure 20A:
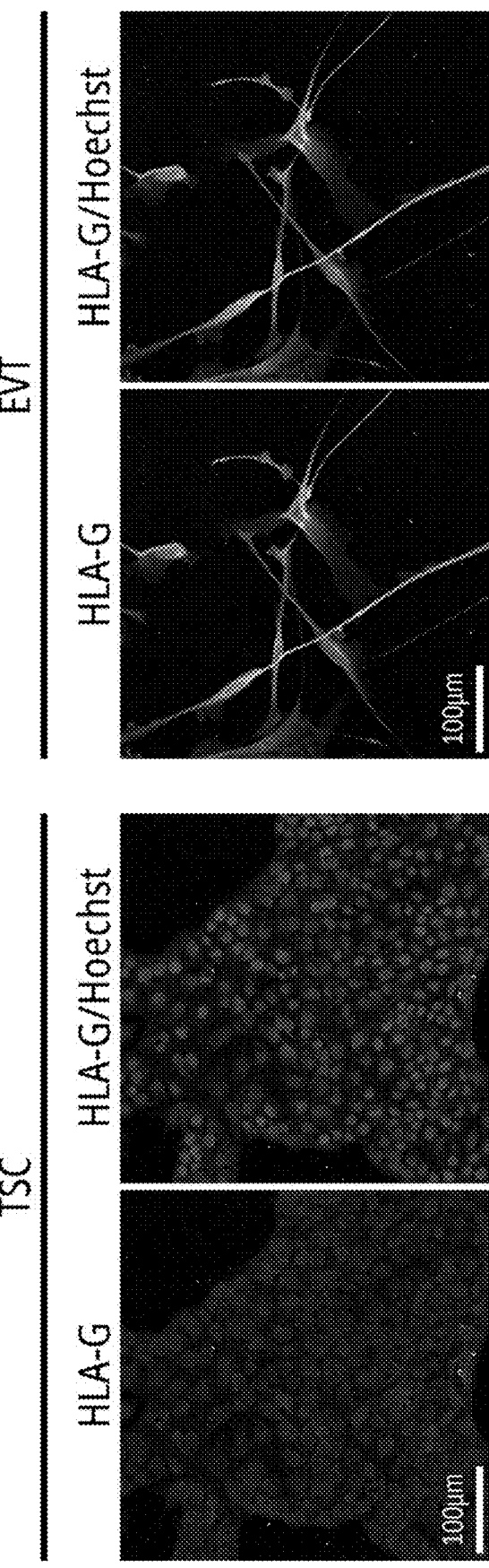
FIG. 20A is a photographic image illustrating immunocytochemical analysis of TSC before and after differentiation into EVT using the EVT marker HLA-G.
Figure 20B:
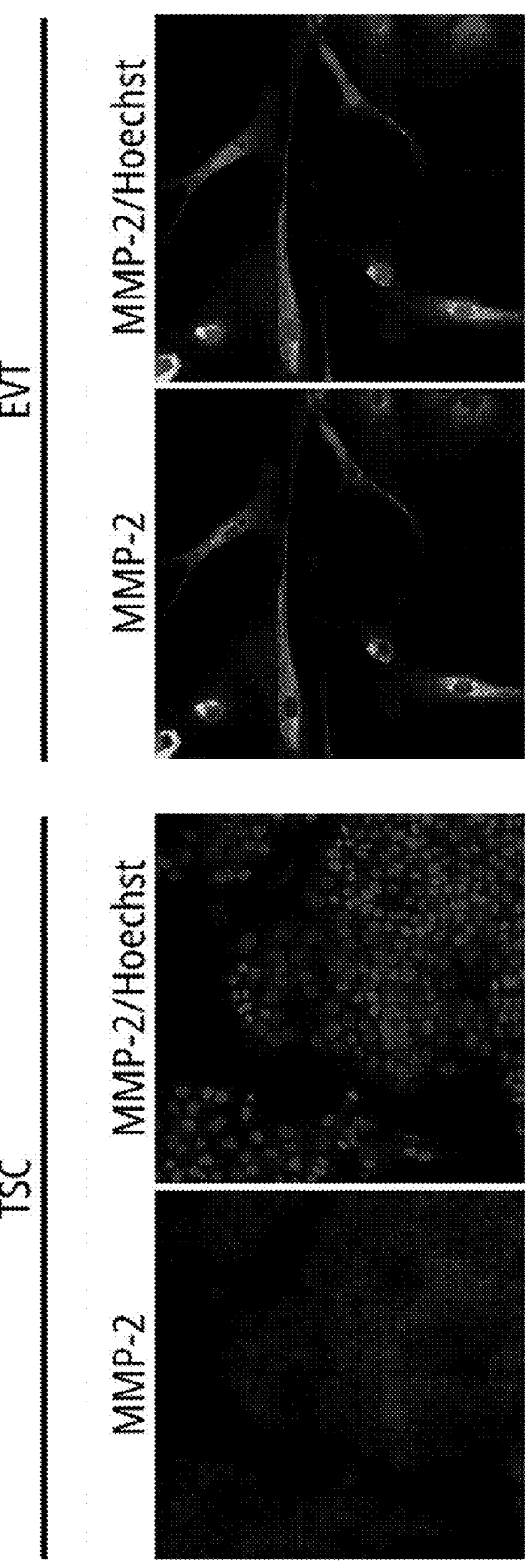
FIG. 20B is a photographic image illustrating immunocytochemical analysis of TSC before and after differentiation into EVT using the EVT marker MMP2.
Figure 20C:
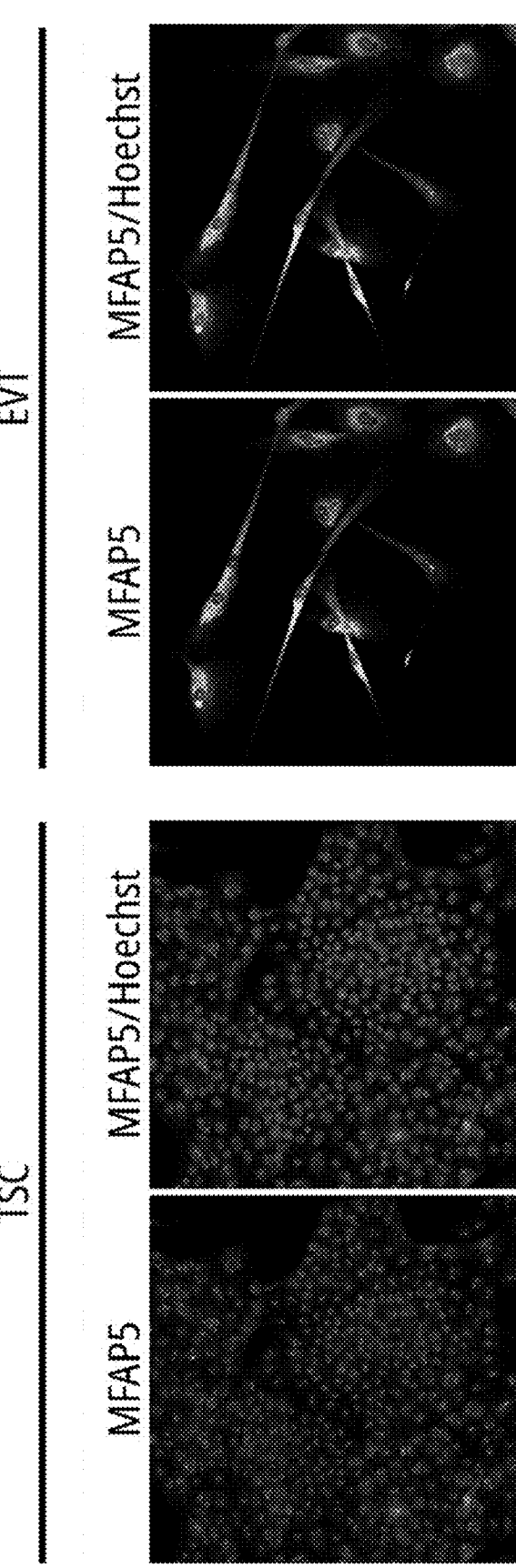
FIG. 20C is a photographic image illustrating immunocytochemical analysis of TSC before and after differentiation into EVT using the EVT marker MFAP5.
Figure 20D:
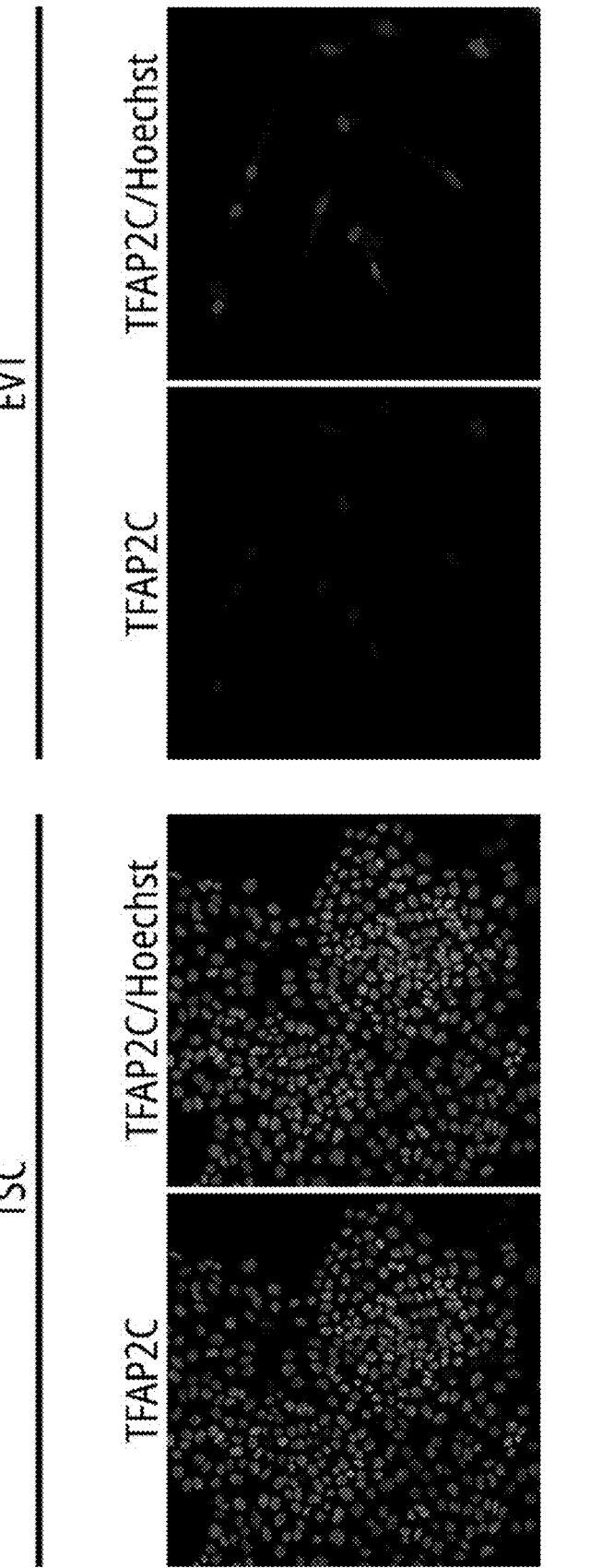
FIG. 20D is a photographic image illustrating immunocytochemical analysis of TSC before and after differentiation into EVT using the EVT marker TFAP2C, which was no longer expressed after differentiation into EVT.

Differentiation of TSC into EVT depends on a biological process called epithelial-to-mesenchymal transition (EMT), such that protocols were developed to ensure efficient differentiation. FIG. 19 illustrates exemplary protocols for differentiation of TSC into EVT lasting 14 days and passaging ("pass.") at day 2 and 8. The cells acquire spindle-shaped morphology, indicating epithelial-to-mesenchymal transition, which is typical for EVT cells. Protocol for differentiation of TSC into STB over 4 days, leading to the formation of multinucleated cells. Typical EVT markers HLA-G (FIG. 20A), MMP2 (FIG. 20B) and MFAP5 (FIG. 20C) are expressed by TSC-derived EVT (WA09 ESC line). The markers were strongly induced in EVT and absent in TSC controls (left panel of FIGS. 20A-C). Note that the TSC marker TFAP2C was no longer expressed after differentiation into EVT (FIG. 20D).

Figure 20E:
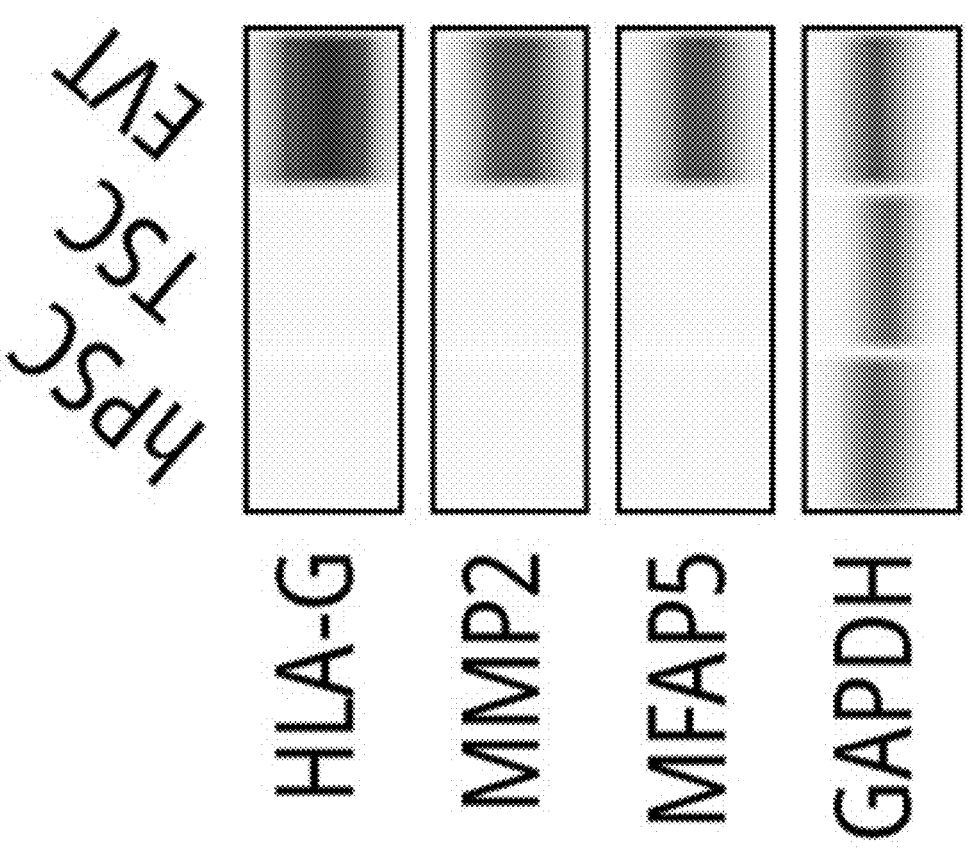
FIG. 20E shows protein expression (Western blot analysis) in hPSCs, TSC, and TSC-derived EVT.
Figures 21C, 21D:
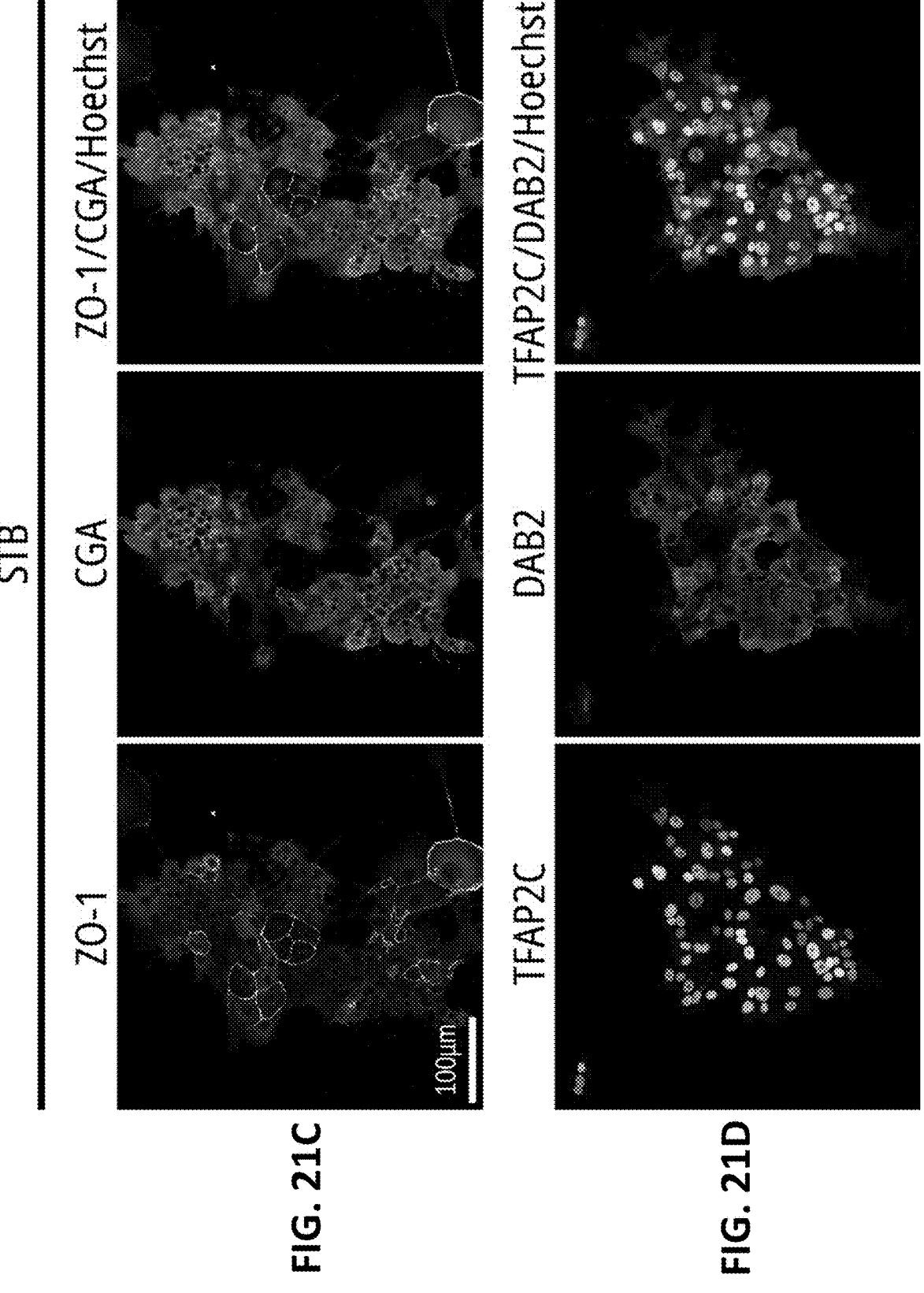
FIG. 21C is a photographic image illustrating immunocytochemical analysis of TSC before and after differentiation into STB as described in the present disclosure.
FIG. 21D is a photographic image illustrating immunocytochemical analysis of TSC before and after differentiation into STB as described in the present disclosure.

FIG. 20E shows that Western blot analysis confirms strong expression of typical markers (HLA-G, MMP2, MFAP5) in EVT but absence in hPSC and TSC (all cells derived from WA09 ESC line), which served as controls. Turning now to FIGS. 21A-D, immunofluorescence images showed induction of STB markers CGA and DAB2, which were absent in TSC controls. TFAP2C was maintained in both cell types and as expected, ZO-1 disintegrated upon cell fusion and formation of STB.

Figure 22:
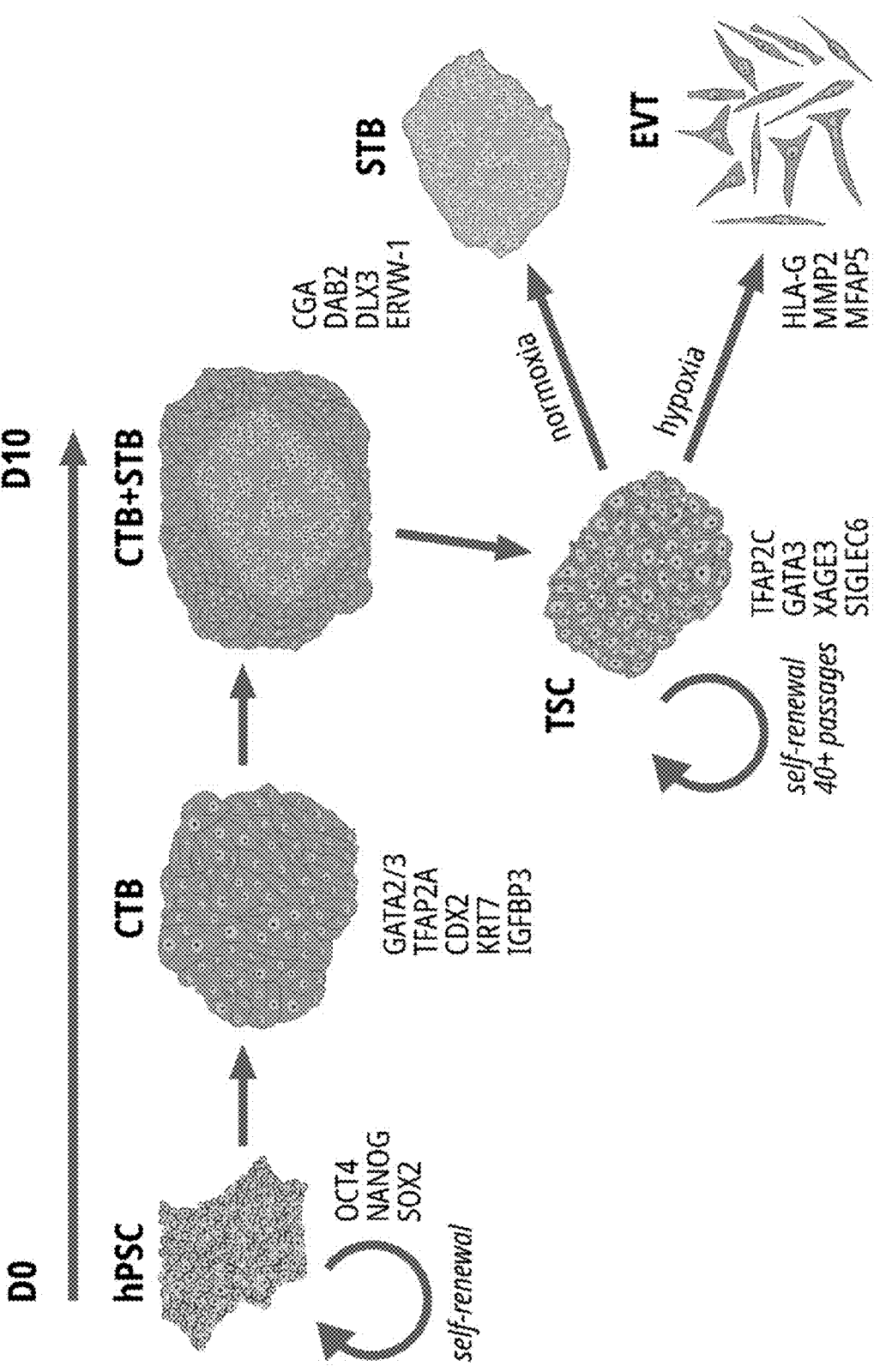
FIG. 22 shows an exemplary summary embodiment capturing the controlled differentiation and characterization of distinct trophectoderm lineage cells derived from human pluripotent stem cells as described in the present disclosure.

FIG. 22 summarizes the exemplary methods and protocols disclosed herein that provide a robust and comprehensive roadmap enabling the production of human placental cells for basic and translation research. In some embodiments, the CEPT cocktail is used for stress-free passaging of self-renewing TSCs. Altogether, the embodiments and methods described herein allow study and development of new diagnostic and therapeutic approaches for infertility, placental dysfunction, miscarriage, pre-eclampsia, fetal growth restriction, birth defects and intoxication by environmental substances.

The invention claimed is:

1. A method of producing a cytotrophoblast-like cell, the method comprising:
   plating a mammalian pluripotent stem cell onto a substrate-coated surface;
   culturing the plated mammalian pluripotent stem cell for at least 12 hours in a first culture medium, thereby producing a plurality of adherent cells; and
   culturing the plurality of adherent cells in a second culture medium for approximately 24-96 hours,
   wherein the plurality of adherent cells is approximately 25-50% confluent before the culturing in the second culture medium; and
   wherein the second culture medium comprises:
      i) an effective concentration of at least one inhibitor of transforming growth factor beta (TGF-beta) signaling;
      ii) an effective concentration of at least one activator of Wnt signaling;
      iii) an effective concentration of at least one inhibitor of fibroblast growth factor (FGF) receptor signaling;
      iv) an effective concentration of bone morphogenic protein 4 (BMP4); and
      v) an effective concentration of bone morphogenic protein 10 (BMP10).

2. The method of claim 1, wherein the substrate comprises at least one of vitronectin, laminin, and basement membrane matrix.

3. The method of claim 2, wherein the first culture medium comprises feeder-free medium or mouse embryonic fibroblast (MEF)-conditioned medium.

4. The method of claim 1, wherein the first culture medium further comprises an effective concentration of (3S)—N-{2-[2-(Dimethylamino)ethoxy]-4-(1H-pyrazol-4-yl)phenyl}-6-methoxy-3,4-dihydro-2H-1-benzopyran-3-carboxamide, an effective concentration of 3-(2-(2-tert-butylphenylaminooxalyl)aminopropionylamino)-4-oxo-5-(2,3,5,6-tetrafluorophenoxy)pentanoic acid, an effective concentration of N,N'-((1r,4r)-cyclohexane-1,4-diyl)bis(2-(4-chlorophenoxy)acetamide), or an effective concentration of a polyamine.

5. The method of claim 1, wherein the at least one inhibitor of TGF-beta signaling comprises at least one of 3-(6-Methyl-2-pyridinyl)-N-phenyl-4-(4-quinolinyl)-1H- pyrazole-1-carbothioamide and 4-[4-(1,3-benzodioxol-5-yl)-5-(2-pyridinyl)-1H-imidazol-2-yl]benzamide.

6. The method of claim 1, wherein the at least one activator of Wnt signaling comprises at least one of 6-[[2-[[4-(2,4-Dichlorophenyl)-5-(5-methyl-1H-imidazol-2-yl)-2-pyrimidinyl]amino]ethyl]amino]-3-pyridinecarbonitrile and N2-(2-(4-(2,4-dichlorophenyl)-5-(1H-imidazol-1-yl)pyrimidin-2-ylamino)ethyl)-5-nitropyridine-2,6-diamine.

7. The method of claim 1, wherein the at least one inhibitor of FGF receptor signaling comprises at least one of (5-amino-1-(2-methyl-3H-benzo[d]imidazol-5-yl)-1H-pyrazol-4-yl)(1H-indol-2-yl)methanone, 1-[2-amino-6-(3,5-dimethoxyphenyl)-pyrido[2,3-d]pyrimidin-7-yl]-3-tert-butyl urea, and N-[2-[[4-(Diethylamino)butyl]amino-6-(3,5-dimethoxyphenyl)pyrido[2,3-d]pyrimidin-7-yl]-N'-(1,1-dimethylethyl)urea.

8. The method of claim 4, wherein the polyamine comprises putrescine, spermine, or spermidine.

9. A method of producing a syncytiotrophoblast-like structure, the method comprising culturing a cytotrophoblast-like cell in a culture medium for approximately 168-312 hours, wherein the culture medium comprises an effective concentration of at least one inhibitor of transforming growth factor beta (TGF-beta) signaling and an effective concentration of at least one inhibitor of Wnt signaling.

10. The method of claim 9, wherein the at least one inhibitor of TGF-beta signaling comprises at least one of 3-(6-Methyl-2-pyridinyl)-N-phenyl-4-(4-quinolinyl)-1H-pyrazole-1-carbothioamide and 4-[4-(1,3-benzodioxol-5-yl)-5-(2-pyridinyl)-1H-imidazol-2-yl]benzamide.

11. The method of claim 9, wherein the at least one activator of Wnt signaling comprises at least one of 6-[[2-[[4-(2,4-Dichlorophenyl)-5-(5-methyl-1H-imidazol-2-yl)-2-pyrimidinyl]amino]ethyl]amino]-3-pyridinecarbonitrile and N2-(2-(4-(2,4-dichlorophenyl)-5-(1H-imidazol-1-yl)pyrimidin-2-ylamino)ethyl)-5-nitropyridine-2,6-diamine.

12. A method of producing a syncytiotrophoblast-like structure, the method comprising:
   plating a mammalian pluripotent stem cell onto a substrate-coated surface;
   culturing the plated mammalian pluripotent stem cell for at least 12 hours in a first culture medium, thereby producing a plurality of adherent cells; and
   culturing the plurality of adherent cells in a second culture medium for approximately 24-96 hours, thereby producing a cytotrophoblast-like cell; and
   culturing the cytotrophoblast-like cell in a third culture medium,
   wherein:
   the plurality of adherent cells is approximately 25-50% confluent before the culturing in the second culture medium;
   the second culture medium comprises:
      i) an effective concentration of at least one first inhibitor of transforming growth factor beta (TGF-beta) signaling;
      ii) an effective concentration of at least one first activator of Wnt signaling;
      iii) an effective concentration of at least one inhibitor of fibroblast growth factor (FGF) receptor signaling;
      iv) an effective concentration of bone morphogenic protein 4 (BMP4); and
      V) an effective concentration of bone morphogenic protein 10 (BMP 10);
   and
   the third culture medium comprises an effective concentration of at least one second inhibitor of TGF-beta signaling and an effective concentration of at least one second inhibitor of Wnt signaling.

13. The method of claim 12, wherein the at least one second inhibitor of TGF-beta signaling comprises at least one of 3-(6-Methyl-2-pyridinyl)-N-phenyl-4-(4-quinolinyl)-1H-pyrazole-1-carbothioamide and 4-[4-(1,3-benzodioxol-5-yl)-5-(2-pyridinyl)-1H-imidazol-2-yl]benzamide.

14. The method of claim 12, wherein the at least one second activator of Wnt signaling comprises at least one of 6-[[2-[[4-(2,4-Dichlorophenyl)-5-(5-methyl-1H-imidazol-2-yl)-2-pyrimidinyl]amino]ethyl]amino]-3-pyridinecarbonitrile and N2-(2-(4-(2,4-dichlorophenyl)-5-(1H-imidazol-1-yl)pyrimidin-2-ylamino)ethyl)-5-nitropyridine-2,6-diamine.

* * * * *